(12) United States Patent
Steinbach et al.

(10) Patent No.: US 7,637,892 B2
(45) Date of Patent: Dec. 29, 2009

(54) VARIABLE FLOW INFUSION PUMP SYSTEM

(75) Inventors: Bernd Steinbach, Friedberg (DE);
Frank Wallmann, Pfungstadt (DE);
Klaus G. Lederer, Naples, FL (US);
David Saar, Titusville, NJ (US); Sidney David, Livingston, NJ (US)

(73) Assignee: Palyon Medical (BVI) Limited, Tortola (VG)

( * ) Notice: Subject to any disclaimer, the term of this patent is extended or adjusted under 35 U.S.C. 154(b) by 441 days.

(21) Appl. No.: 11/601,586

(22) Filed: Nov. 17, 2006

(65) Prior Publication Data
US 2007/0112328 A1 May 17, 2007

Related U.S. Application Data

(63) Continuation-in-part of application No. 11/125,586, filed on May 10, 2005, and a continuation-in-part of application No. 11/126,101, filed on May 10, 2005, and a continuation-in-part of application No. 11/157,437, filed on Jun. 21, 2005.

(51) Int. Cl.
*A61M 1/00* (2006.01)
*A61M 37/00* (2006.01)

(52) U.S. Cl. .................... 604/153; 604/141

(58) Field of Classification Search .............. 604/93.01, 604/118, 131–133, 140, 141, 145, 146, 153, 604/167.03, 246–250, 890.1, 891.1; 128/DIG. 12; 251/4, 7, 8, 129.06
See application file for complete search history.

(56) References Cited

U.S. PATENT DOCUMENTS

| | | |
|---|---|---|
| 3,951,147 A | 4/1976 | Tucker et al. |
| 4,077,405 A | 3/1978 | Haerten et al. |
| 4,187,870 A | 2/1980 | Akkerman |

(Continued)

FOREIGN PATENT DOCUMENTS

DE 9107030 6/1991

(Continued)

OTHER PUBLICATIONS

Website printout: www.medtronic.com/neuro/paintherapies/pain <http://www.medtronic.com/neuro/paintherapies/pain>; N'Vision Programmer Discussion.

(Continued)

*Primary Examiner*—Nicholas D Lucchesi
*Assistant Examiner*—Nathan R Price
(74) *Attorney, Agent, or Firm*—Lerner, David, Littenberg, Krumholz & Mentlik, LLP

(57) ABSTRACT

An implantable infusion pump system is disclosed. The pump system preferably includes an implantable pump and a removable module. The module may provide for varying flow rates of fluid being dispensed from the pump or may provide for a constant flow rate of such fluid. In the case of varying flow rate capabilities, the module preferably includes one or more sensors to determine information relating to the flow rate, electronics for analyzing the flow rate information, and a mechanism for physically altering the flow rate. Methods of dispensing a medicament to a patient are also disclosed, as are variations of the pump system.

28 Claims, 44 Drawing Sheets

U.S. PATENT DOCUMENTS

| | | |
|---|---|---|
| 4,193,397 A | 3/1980 | Tucker et al. |
| 4,270,532 A | 6/1981 | Franetzki et al. |
| 4,299,220 A | 11/1981 | Dorman |
| 4,373,527 A | 2/1983 | Fischell |
| 4,411,651 A | 10/1983 | Schulman |
| 4,443,218 A | 4/1984 | DeCant, Jr. et al. |
| 4,447,224 A | 5/1984 | DeCant, Jr. et al. |
| 4,486,190 A | 12/1984 | Reinicke |
| 4,496,343 A | 1/1985 | Prosl et al. |
| 4,511,163 A | 4/1985 | Harris et al. |
| 4,557,726 A | 12/1985 | Reinicke |
| 4,573,994 A | 3/1986 | Fischell et al. |
| 4,626,244 A | 12/1986 | Reinicke |
| 4,627,840 A | 12/1986 | Cuadra et al. |
| 4,639,244 A | 1/1987 | Rizk et al. |
| 4,661,097 A | 4/1987 | Fischell et al. |
| 4,671,320 A | 6/1987 | Grifols Lucas |
| 4,685,902 A | 8/1987 | Edwards et al. |
| 4,714,462 A | 12/1987 | DiDomenico |
| 4,718,893 A | 1/1988 | Dorman et al. |
| 4,738,665 A | 4/1988 | Shepard |
| 4,772,263 A | 9/1988 | Dorman et al. |
| 4,772,270 A | 9/1988 | Wiita et al. |
| 4,838,887 A | 6/1989 | Idriss |
| 4,915,690 A | 4/1990 | Cone et al. |
| 4,931,050 A | 6/1990 | Idriss |
| 4,955,861 A | 9/1990 | Enegren et al. |
| 4,969,873 A | 11/1990 | Steinbach et al. |
| 4,978,338 A | 12/1990 | Melsky et al. |
| 5,015,374 A | 5/1991 | Mathieu et al. |
| 5,045,060 A | 9/1991 | Melsky et al. |
| 5,061,242 A | 10/1991 | Sampson |
| 5,067,943 A | 11/1991 | Burke |
| 5,085,656 A | 2/1992 | Polaschegg |
| 5,088,983 A | 2/1992 | Burke |
| 5,135,498 A | 8/1992 | Kam et al. |
| 5,147,483 A | 9/1992 | Melsky et al. |
| 5,163,920 A | 11/1992 | Olive |
| 5,205,819 A | 4/1993 | Ross et al. |
| 5,207,666 A | 5/1993 | Idriss et al. |
| 5,217,442 A | 6/1993 | Davis |
| 5,242,406 A | 9/1993 | Gross et al. |
| 5,336,194 A | 8/1994 | Polaschegg et al. |
| 5,395,324 A | 3/1995 | Hinrichs et al. |
| 5,405,339 A | 4/1995 | Kohnen et al. |
| 5,445,616 A | 8/1995 | Kratoska et al. |
| 5,462,525 A | 10/1995 | Srisathapat et al. |
| 5,474,552 A | 12/1995 | Palti |
| 5,549,866 A | 8/1996 | Grifols Lucas |
| 5,569,186 A | 10/1996 | Lord et al. |
| 5,575,770 A | 11/1996 | Melsky et al. |
| 5,637,102 A | 6/1997 | Tolkoff et al. |
| 5,665,070 A | 9/1997 | McPhee |
| 5,667,504 A | 9/1997 | Baumann et al. |
| 5,704,915 A | 1/1998 | Melsky et al. |
| 5,722,957 A | 3/1998 | Steinbach |
| 5,766,150 A | 6/1998 | Langkau |
| 5,769,823 A | 6/1998 | Otto et al. |
| 5,785,681 A | 7/1998 | Indravudh |
| 5,785,688 A | 7/1998 | Joshi et al. |
| 5,792,104 A | 8/1998 | Speckman et al. |
| 5,814,019 A | 9/1998 | Steinbach et al. |
| 5,836,915 A | 11/1998 | Steinbach et al. |
| 5,840,063 A | 11/1998 | Flaherty |
| 5,904,666 A | 5/1999 | DeDecker et al. |
| 5,931,829 A | 8/1999 | Burbank et al. |
| 5,949,632 A | 9/1999 | Barreras, Sr. et al. |
| 5,957,891 A | 9/1999 | Kriesel et al. |
| 5,980,508 A | 11/1999 | Cardamone et al. |
| 6,048,328 A | 4/2000 | Haller et al. |
| 6,166,518 A | 12/2000 | Echarri et al. |
| 6,181,105 B1 | 1/2001 | Cutolo et al. |
| 6,203,523 B1 | 3/2001 | Haller et al. |
| 6,213,972 B1 | 4/2001 | Butterfield et al. |
| 6,238,369 B1 | 5/2001 | Burbank et al. |
| 6,278,258 B1 | 8/2001 | Echarri et al. |
| 6,280,416 B1 | 8/2001 | Van Antwerp et al. |
| 6,283,944 B1 | 9/2001 | McMullen et al. |
| 6,349,740 B1 | 2/2002 | Cho et al. |
| 6,416,291 B1 | 7/2002 | Butterfield et al. |
| 6,416,495 B1 | 7/2002 | Kriesel et al. |
| 6,423,029 B1 | 7/2002 | Elsberry |
| 6,464,671 B1 | 10/2002 | Elver et al. |
| 6,471,645 B1 | 10/2002 | Warkentin |
| 6,471,675 B1 | 10/2002 | Rogers et al. |
| 6,488,652 B1 | 12/2002 | Weijand et al. |
| 6,558,320 B1 | 5/2003 | Causey, III et al. |
| 6,562,001 B2 | 5/2003 | Lebel et al. |
| 6,577,899 B2 | 6/2003 | Lebel et al. |
| 6,589,205 B1 | 7/2003 | Meadows |
| 6,620,151 B2 | 9/2003 | Blischak et al. |
| 6,638,263 B1 | 10/2003 | Theeuwes et al. |
| 6,641,533 B2 | 11/2003 | Causey, III et al. |
| 6,648,821 B2 | 11/2003 | Lebel et al. |
| 6,652,510 B2 | 11/2003 | Lord et al. |
| 6,664,763 B2 | 12/2003 | Echarri et al. |
| 6,676,104 B2 | 1/2004 | Tillander |
| 6,687,546 B2 | 2/2004 | Lebel et al. |
| 6,702,779 B2 | 3/2004 | Connelly et al. |
| 6,719,739 B2 | 4/2004 | Verbeek et al. |
| 6,749,587 B2 | 6/2004 | Flaherty |
| 6,764,472 B1 | 7/2004 | Burke et al. |
| 6,805,687 B2 | 10/2004 | Dextradeur et al. |
| 6,814,547 B2 | 11/2004 | Childers et al. |
| 6,869,275 B2 | 3/2005 | Dante et al. |
| 6,878,135 B1 | 4/2005 | Haller et al. |
| 6,895,419 B1 | 5/2005 | Cargin, Jr. et al. |
| 6,902,544 B2 | 6/2005 | Ludin et al. |
| 6,932,114 B2 | 8/2005 | Sparks |
| 6,997,919 B2 | 2/2006 | Olsen et al. |
| 7,018,384 B2 | 3/2006 | Skakoon |
| 7,083,593 B2 | 8/2006 | Stultz |
| 7,108,686 B2 | 9/2006 | Burke et al. |
| 7,150,741 B2 | 12/2006 | Erickson et al. |
| 7,214,221 B2 | 5/2007 | Fentress et al. |
| 7,367,968 B2 | 5/2008 | Rosenberg et al. |
| 2002/0022759 A1 | 2/2002 | Forsell |
| 2002/0072721 A1 | 6/2002 | Verbeek et al. |
| 2002/0120186 A1 | 8/2002 | Keimel |
| 2002/0156463 A1 | 10/2002 | Berrigan |
| 2002/0193751 A1 | 12/2002 | Theeuwes et al. |
| 2003/0214199 A1 | 11/2003 | Heim et al. |
| 2003/0216683 A1 | 11/2003 | Shekalim |
| 2004/0005433 A1 | 1/2004 | Iguchi et al. |
| 2004/0005931 A1 | 1/2004 | Wang et al. |
| 2004/0054333 A1 | 3/2004 | Theeuwes |
| 2004/0055648 A1 | 3/2004 | Erickson |
| 2004/0059315 A1 | 3/2004 | Erickson et al. |
| 2004/0068224 A1 | 4/2004 | Couvillon et al. |
| 2004/0143242 A1 | 7/2004 | Ludin et al. |
| 2004/0153029 A1 | 8/2004 | Blischak et al. |
| 2004/0202691 A1 | 10/2004 | Richard |
| 2004/0204673 A1 | 10/2004 | Flaherty |
| 2004/0254565 A1 | 12/2004 | Russell |
| 2005/0011374 A1 | 1/2005 | Dejakum et al. |
| 2005/0024175 A1 | 2/2005 | Gray et al. |
| 2005/0037078 A1 | 2/2005 | Kuo et al. |
| 2005/0038396 A1 | 2/2005 | Claude et al. |
| 2005/0054988 A1 | 3/2005 | Rosenberg et al. |
| 2005/0065500 A1 | 3/2005 | Couvillon et al. |
| 2005/0070883 A1 | 3/2005 | Brown et al. |
| 2005/0075624 A1 | 4/2005 | Miesel |
| 2005/0101942 A1 | 5/2005 | Gillis et al. |
| 2005/0113745 A1 | 5/2005 | Stultz |

| | | | | | | |
|---|---|---|---|---|---|---|
| 2005/0113892 | A1 | 5/2005 | Sproul | 2007/0112328 A1 | 5/2007 | Steinbach et al. |
| 2005/0187515 | A1 | 8/2005 | Varrichio et al. | | | |
| 2005/0197652 | A1 | 9/2005 | Nat | | | |
| 2005/0273081 | A1 | 12/2005 | Olsen | | | |
| 2005/0273082 | A1 | 12/2005 | Olsen | | | |
| 2005/0273083 | A1 | 12/2005 | Lebel et al. | | | |
| 2006/0089619 | A1 | 4/2006 | Ginggen | | | |
| 2006/0253135 | A1 | 11/2006 | Ortiz | | | |
| 2006/0259015 | A1 | 11/2006 | Steinbach | | | |
| 2006/0259016 | A1 | 11/2006 | Steinbach | | | |
| 2006/0271021 | A1 | 11/2006 | Steinbach | | | |
| 2006/0271022 | A1 | 11/2006 | Steinbach et al. | | | |
| 2007/0005044 | A1 | 1/2007 | Steinbach et al. | | | |

FOREIGN PATENT DOCUMENTS

| | | |
|---|---|---|
| EP | 0045668 | 2/1982 |
| FR | 2628639 | 9/1989 |
| JP | 2002-292683 | 10/2002 |
| WO | 03/068049 | 8/2003 |
| WO | 2005007223 | 1/2005 |
| WO | 2005044343 | 5/2005 |
| WO | 2005079885 | 9/2005 |
| WO | 2006/122330 | 11/2006 |

OTHER PUBLICATIONS

Elliptec Resonant Actuator, X15G Preliminary Datasheet, Oct. 2004.

International Search Report, PCT/US2007/024026.

FIG. 10A
FIG. 10B
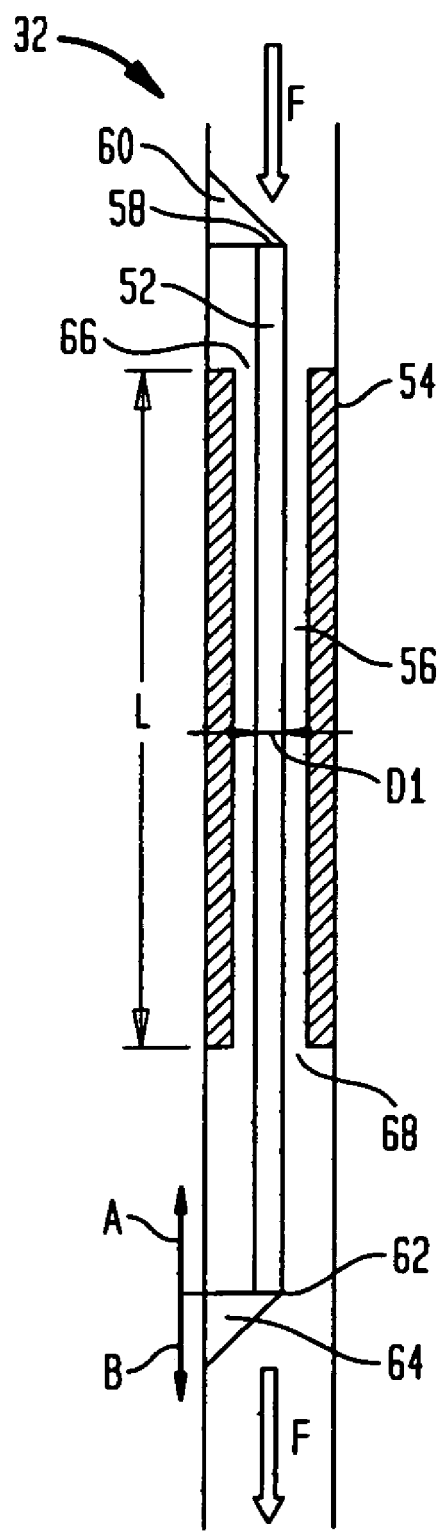
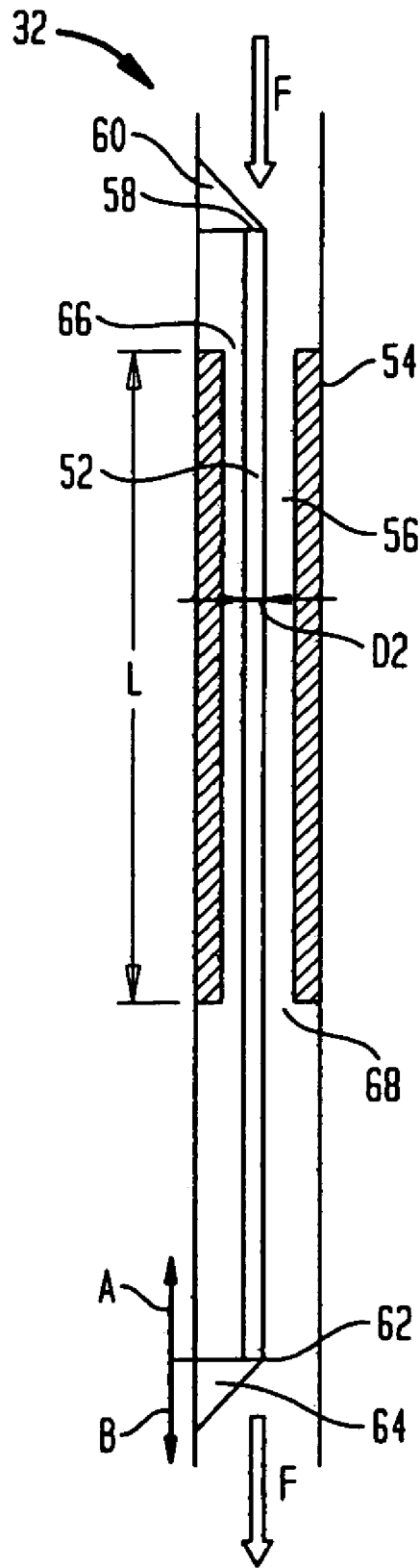

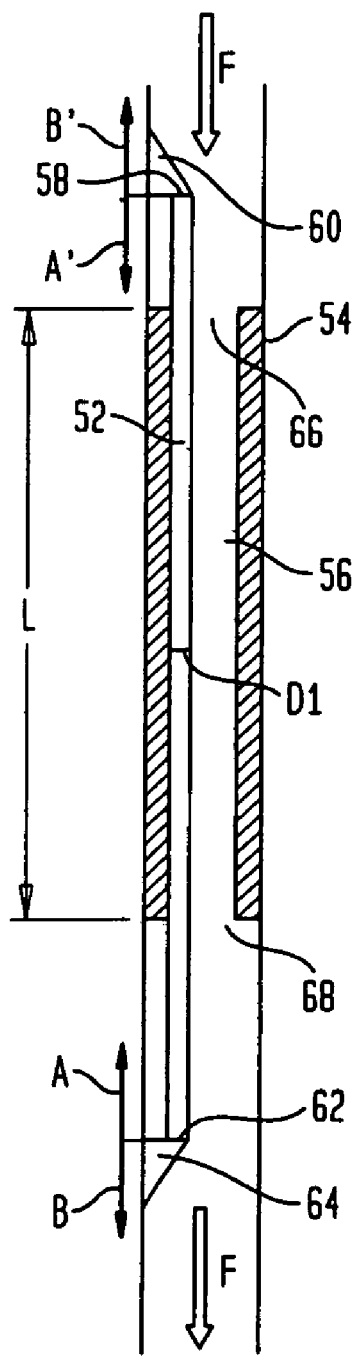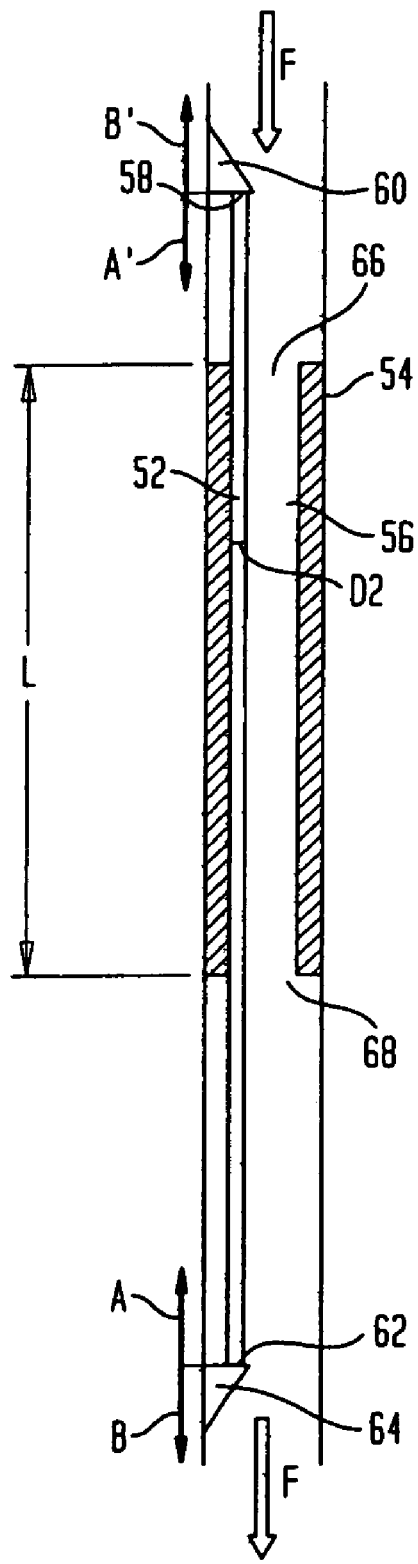

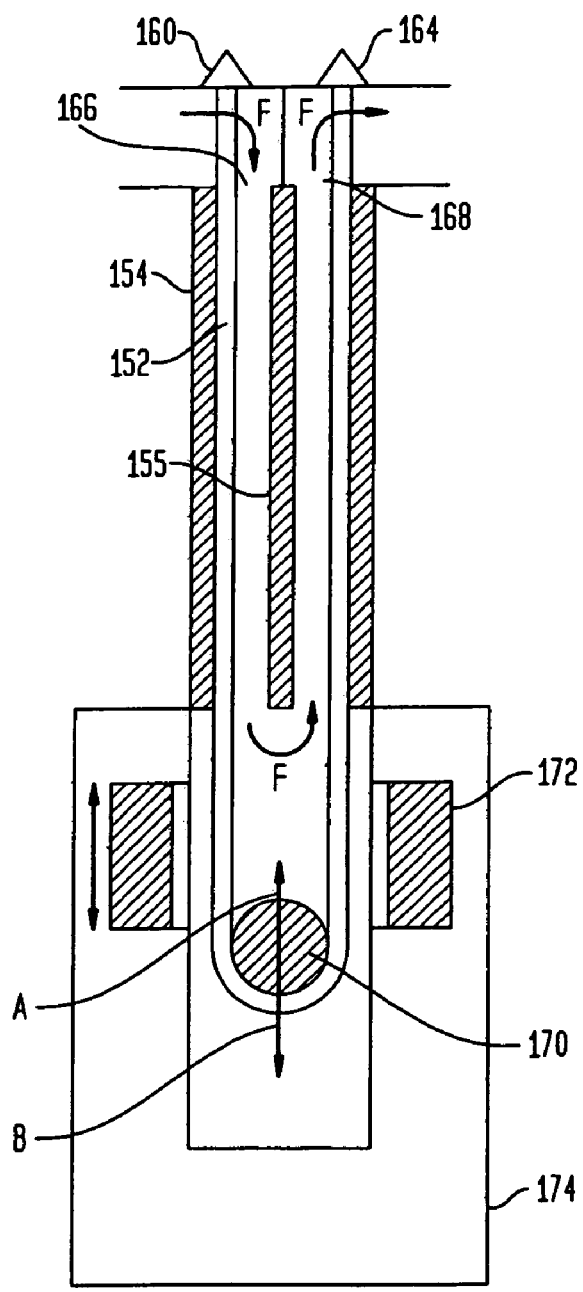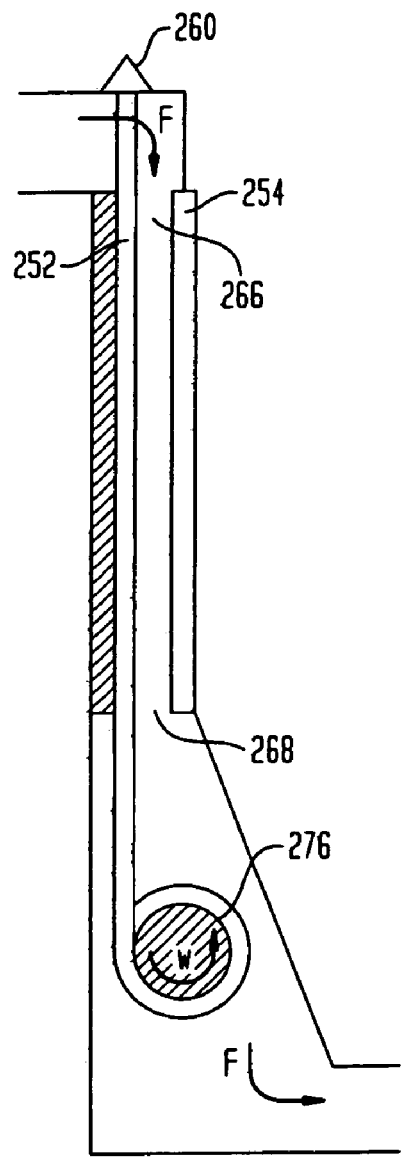
FIG. 13
FIG. 14

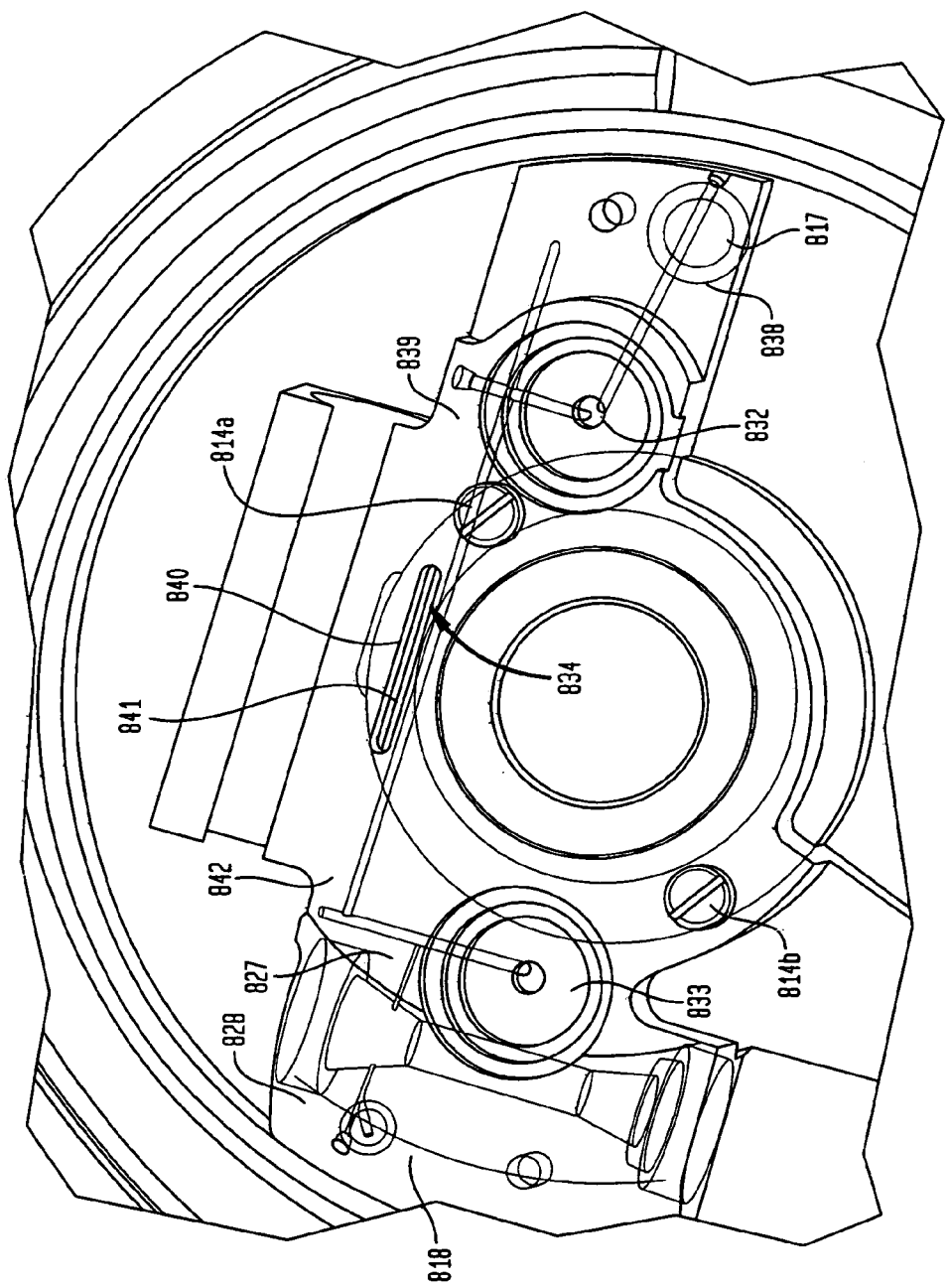

VARIABLE FLOW INFUSION PUMP SYSTEM

CROSS REFERENCE TO RELATED APPLICATIONS

This application is a continuation-in-part of U.S. application Ser. No. 11/125,586, filed on May 10, 2005, U.S. application Ser. No. 11/126,101, filed on May 10, 2005 and U.S. application Ser. No. 11/157,437, filed on Jun. 21, 2005, the disclosures of which are incorporated herein by reference.

BACKGROUND OF THE INVENTION

The present invention relates to implantable devices, and more particularly to reduced size implantable pumps and programmable implantable pumps allowing for variable flow rates in delivering medication or other fluid to a selected site in the human body.

Implantable pumps have been well known and widely utilized for many years. Typically, pumps of this type are implanted into patients who require the delivery of active substances or medication fluids to specific areas of their body. For example, patients that are experiencing severe pain may require painkillers daily or multiple times per day. Absent the use of an implantable pump or the like, a patient of this type would be subjected to one or more painful injections of such medication fluids. In the case of pain associated with more remote areas of the body, such as the spine, these injections may be extremely difficult to administer and particularly painful for the patient. Furthermore, attempting to treat conditions such as this through oral or intravascular administration of medication often requires higher doses of medication and may cause severe side effects. Therefore, it is widely recognized that utilizing an implantable pump may be beneficial to both a patient and the treating physician.

Many implantable pump designs have been proposed. For example, commonly invented U.S. Pat. No. 4,969,873 ("the '873 patent"), the disclosure of which is hereby incorporated by reference herein, teaches one such design. The '873 is an example of a constant flow pump, which typically include a housing having two chambers, a first chamber for holding the specific medication fluid to be administered and a second chamber for holding a propellant. A flexible membrane may separate the two chambers such that expansion of the propellant in the second chamber pushes the medication fluid out of the first chamber. This type of pump also typically includes an outlet opening connected to a catheter for directing the medication fluid to the desired area of the body, a replenishment opening for allowing for refilling of medication fluid into the first chamber and a bolus opening for allowing the direct introduction of a substance through the catheter without introduction into the first chamber. Both the replenishment opening and the bolus opening are typically covered by a septum that allows a needle or similar device to be passed through it, but properly seals the openings upon removal of the needle. As pumps of this type provide a constant flow of medication fluid to the specific area of the body, they must be refilled periodically with a proper concentration of medication fluid suited for extended release.

Although clearly beneficial to patients and doctors that utilize them, one area in which such constant flow implantable pumps can be improved, is in their overall size. Typically, such pumps require rather bulky outer housings, or casings, for accommodating the aforementioned medication and propellant chambers, and septa associated therewith. Often times, implantable pumps are limited to rather small areas within the body. Depending upon the size of the patient for which the pump is implanted, this limited area may be even further limited. For example, a person having smaller body features, or those containing abnormal anatomy, may present a doctor implanting a constant flow pump with some added difficulty. Further, patients may be uncomfortable having standard sized constant flow pumps implanted in them. Such pumps are often times capable of being felt from the exterior of the patient.

Implantable pumps may also be of the programmable type. Pumps of this type provide variable flow rates, typically through the use of a solenoid pump or a peristaltic pump. In the solenoid pump, the flow rate of medication fluid can be controlled by changing the stroke rate of the pump. In the peristaltic pump, the flow rate can be controlled by changing the roller velocity of the pump. However, both of these types of programmable pumps require intricate designs and complicated controlling mechanisms. As such, it would be more desirable to utilize pumps having designs similar to the aforementioned constant flow pumps.

However, the benefit of providing a variable flow rate pump cannot be forgotten. While a constant flow of a medication such as a painkiller may indeed be useful in dulling chronic pain, it is very common for patients to experience more intense pain. At times of this heightened pain, it would be advantageous to be able to vary the flow rate of pain killer to provide for more relief. However, constant flow rate pumps typically may only provide such relief by allowing for direct injections of painkillers or the like through the aforementioned bolus port, which provides direct access to the affirmed area. While indeed useful, this method amounts to nothing more than additional painful injections, something the pump is designed to circumvent.

Therefore, there exists a need for an implantable constant flow pump, which allows for a reduced overall size, as well as an implantable pump that combines the simplistic design of a constant flow rate type pump and means for varying its flow rate, without requiring the use of the complex solutions provided by known programmable pumps.

SUMMARY OF THE INVENTION

A first aspect of the present invention is a reduced size implantable device for dispensing an active substance to a patient. The implantable device of a first embodiment of this first aspect includes a housing defining an active substance chamber in fluid communication with an outlet for delivering the active substance to a target site within the patient and a propellant chamber adjacent the active substance chamber. The implantable device further includes an undulating flexible membrane separating the active substance and propellant chambers, wherein the active substance chamber has an undulating surface including a central convex portion flanked by at least two concave portions, the undulating surface cooperating with the undulating flexible membrane.

In accordance with this first embodiment of the first aspect of the present invention, the propellant chamber may contain a propellant capable of expanding isobarically where the propellant cooperates with the flexible membrane to reduce the volume of the active substance chamber upon expansion of the propellant. The cooperating undulating surface of the active substance chamber and the undulating flexible membrane preferably meet upon complete expansion of the propellant. The implantable device may further include a replenishment opening in the housing in fluid communication with the active substance chamber, and a first septum sealing the opening. The replenishment opening may be located within the central convex portion of the undulating surface of the active substance chamber so as to lower the overall height of the housing of the implantable device. Additionally, the housing may include two portions being constructed so as to screw together. The two portions may be constructed of PEEK. The two portions may be configured so as to capture the membrane therebetween. Finally, the housing may also include a locking portion and/or a septum retaining member.

A second embodiment of this first aspect of the present invention is yet another implantable device for dispensing an active substance to a patient. The implantable device according to this second embodiment includes a housing defining a chamber and an outlet in fluid communication with the chamber for delivering the active substance to a target site within the patient, the housing having a first portion and a second portion, where the first and second portions are constructed of PEEK and screwed together.

A third embodiment of this first aspect of the present invention is yet another implantable device for dispensing an active substance to a patient. The implantable device according to this third embodiment includes a housing including a top portion, a bottom portion and a locking portion. The housing defines a propellant chamber and an active substance chamber in fluid communication with an outlet. The implantable device preferably also includes a membrane retained between the top and bottom portions, the membrane separating the active substance and propellant chambers. In a fully assembled stated, the top and bottom portions are preferably placed together and the locking portion engages one of the top or bottom portions to retain the top and bottom portions together.

A fourth embodiment of this first aspect of the present invention relates to a method of assembling a reduced size implantable pump. The method of this embodiment includes the steps of placing together a top portion and a bottom portion to retain a membrane therebetween, and screwing a locking portion into the top portion or the bottom portion to retain the top and bottom portions together.

A second aspect of the present invention includes an implantable device for dispensing an active substance to a patient including a housing defining a chamber, said housing having an outlet for delivering the active substance to a target site within the patient, the outlet in fluid communication with the chamber and means for varying the flow rate of the active substance between the chamber and the outlet. The chamber, in accordance with this second aspect of the present invention, may include an active substance chamber in fluid communication with the outlet and a propellant chamber, the active substance and propellant chambers being separated by a flexible membrane. The propellant chamber may contain a propellant capable of expanding isobarically and cooperating with the flexible membrane to reduce the volume of the active substance chamber upon expansion of the propellant. The housing of the implantable device may include an opening in fluid communication with the active substance chamber and a first septum sealing the opening. The housing may further include an annular opening in communication with the outlet and a second septum sealing the annular opening.

In a first embodiment of this second aspect, the means for varying the flow rate of the active substance between the chamber and the outlet may include an elongated polymer filament having a cross sectional dimension. The filament, in accordance with this embodiment, is preferably located in a capillary and is preferably capable of being elongated to reduce the cross sectional dimension. In certain examples, the filament is located centrally within the capillary, in others, it is located eccentrically. The filament may have a uniform cross section, a substantially circular cross section, non-uniform cross section and the like along its length. Further, this first embodiment may further include means for elongating the filament.

In a second embodiment of this second aspect, the means for varying the flow rate of the active substance between the chamber and the outlet may include a first hollow cylinder having a threaded exterior surface and a second hollow cylinder having a threaded interior surface. The first hollow cylinder is axially received within the second hollow cylinder, such that the threaded exterior surface of the first cylinder engages the threaded interior surface of the second cylinder. In this embodiment, the axial movement of the first cylinder with respect to the second cylinder varies the flow rate of the active substance.

In a third embodiment of this second aspect, the means for varying the flow rate of the active substance between the chamber and the outlet may include a hollow tubular element having a cross section that is capable of being varied. This third embodiment may also include a capillary in fluid communication between the chamber and the outlet, where the tubular element is located therein. The hollow tubular element in accordance with this embodiment may be centrally or eccentrically located within the capillary.

In a fourth embodiment of this second aspect, the means for varying the flow rate of the active substance between the chamber and the outlet may include an elongate insert having a longitudinally varying cross section along its length. Movement of this elongate insert may increase or decrease the flow rate of the active substance.

A third aspect of the present invention includes an implantable device for dispensing an active substance to a patient including a housing defining a chamber, said housing having an outlet for delivering the active substance to a target site within the patient, the outlet in fluid communication with the chamber. The implantable device also includes a capillary in fluid communication between the chamber and the outlet, the capillary having an inner surface and a flow control element received within the capillary. The element has an outer surface opposing the inner surface of the capillary defining therebetween a passageway for the flow of the active substance therethrough. The outer surface of the element is preferably movable relative to the inner surface of the capillary to alter the flow of the active substance therethrough. The movement of the outer surface of the element may alter the shape and/or size of the passageway.

In a first embodiment of this third aspect, the means for varying the flow rate of the active substance between the chamber and the outlet may include an elongated polymer filament having a cross sectional dimension. The filament, in accordance with this embodiment, is preferably located in a capillary and is preferably capable of being elongated to reduce the cross sectional dimension. In certain examples, the filament is located centrally within the capillary, in others, it is located eccentrically. The filament may have a uniform cross section, a substantially circular cross section, non-uniform cross section and the like along its length. Further, this first embodiment may further include means for elongating the filament.

In a second embodiment of this third aspect, the means for varying the flow rate of the active substance between the chamber and the outlet may include a first hollow cylinder having a threaded exterior surface and a second hollow cylinder having a threaded interior surface. The first hollow cylinder is axially received within the second hollow cylinder, such that the threaded exterior surface of the first cylinder engages the threaded interior surface of the second cylinder.

In this embodiment, the axial movement of the first cylinder with respect to the second cylinder varies the flow rate of the active substance.

In a third embodiment of this third aspect, the means for varying the flow rate of the active substance between the chamber and the outlet may include a hollow tubular element having a cross section that is capable of being varied. This third embodiment may also include a capillary in fluid communication between the chamber and the outlet, where the tubular element is located therein. The hollow tubular element in accordance with this embodiment may be centrally or eccentrically located within the capillary.

In a fourth embodiment of this third aspect, the means for varying the flow rate of the active substance between the chamber and the outlet may include an elongate insert having a longitudinally varying cross section along its length. Movement of this elongate insert may increase or decrease the flow rate of the active substance.

A fourth aspect of the present invention includes a resistor for varying the flow rate of a fluid from a first point to a second point including a capillary having an inner surface and a flow control element received with the capillary. The element has an outer surface opposing the inner surface of the capillary such that a passageway is defined for the flow of fluid therethrough. The outer surface of the element is preferably moveable relative to the inner surface of the capillary to alter the flow of the fluid therethrough. The movement of the outer surface of the element may alter the shape and/or size of the passageway. It is noted that this aspect may be utilized in conjunction with an implantable device such as an implantable pump for delivering a medicament to a site within a patient. Embodiments in accordance with the third aspect may be similar to those discussed above in relation to the first and second aspects of the present invention.

A fifth aspect of the present invention includes a method of varying the flow rate of an active substance being dispensed to a patient. This method includes the steps of providing an implantable device including a capillary having an inner surface and a flow control element received within the capillary. The element preferably has an outer surface opposing the inner surface of the capillary such that a passageway for the flow of the active substance therethrough is defined therebetween for dispensing the active substance to a target site within a patient. Further the method includes the step of moving the element relative to the inner surface of the capillary to alter the flow rate of the active substance therethrough. This moving step may alter the size and/or shape of the passageway.

Yet another aspect of the present invention is an implantable infusion pump system for dispensing an active substance at one or varying flow rates to a patient. The system may include a constant flow pump having a housing defining an active substance chamber, an outlet duct, and an upper surface; and a removable module having a bottom surface contacting the upper surface of the constant flow pump, such that the module facilitates fluid communication between the active substance chamber and the outlet duct.

Yet another aspect of the present invention is a method of implanting an infusion pump. The method may include the steps of determining the need for a variable or constant flow infusion pump, selecting, based upon the determining step, a pump housing and a module, the module selected from a variable flow module and a constant flow module, engaging a bottom surface of the module with an upper surface of the housing to construct the infusion pump, such that the restrictor module is in fluid communication with the housing, and implanting the infusion pump in the body of a patient.

Yet another aspect of the present invention is an implantable infusion pump for dispensing an active substance at varying flow rates to a patient. The pump may include a constant flow pump having a housing defining an upper surface, an active substance chamber, a propellant chamber separated from the active substance chamber by a first flexible membrane, an outlet duct having a catheter attached thereto, an exit opening in fluid communication with the active substance chamber and a entrance opening in fluid communication with the outlet duct. The pump may also include a removable module including a bottom surface contacting the upper surface of the constant flow pump, an entry formed in the bottom surface in fluid communication with the exit opening of the housing, an exit in fluid communication with the entrance opening of the housing, a needle portion having a longitudinally varying cross section along its length disposed within a valve body, means for longitudinally moving the needle portion within the valve body, a fixed flow restrictor in fluid communication between the entry of the module and the valve body of the module, and first and second pressure sensors located on either side of the fixed flow restrictor. Preferably, during operation of the pump system, a fluid dispelled from the active substance chamber by a force from the propellant chamber passes through the exit opening of the housing, through the entry of the module, into contact with the first pressure sensor, through the fixed flow restrictor, into contact with the second pressure sensor, through the valve body of the module, through the exit of the module, through the entrance opening of the housing, through the outlet duct, and through the catheter.

Yet another aspect of the present invention is a method of monitoring the amount of medicament dispensed from an implantable infusion pump. In accordance with one embodiment of this aspect, the method includes the steps of providing a pump having the medicament disposed housed therein, dispensing at least some of the medicament from the pump at varying actual flow rates, measuring the actual flow rate of the medicament from the pump at least two different times, storing information relating to the actual flow rate and calculating the overall amount of medicament dispensed based upon the information relating to the flow rate.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 10a is a longitudinal cross sectional view of the variable flow resistor of FIG. 9, in an initial position.

FIG. 10b is a longitudinal cross sectional view of the variable flow resistor of FIG. 10a, in an extended position.

FIG. 12a is a longitudinal cross sectional view of the variable flow resistor of FIG. 11a, in an initial position.

FIG. 12b is a longitudinal cross sectional view of the variable flow resistor of FIG. 12a, in an extended position.

FIG. 13 is a longitudinal cross sectional view of another variable flow resistor in accordance with the present invention.

FIG. 14 is a longitudinal cross sectional view of another variable flow resistor in accordance with the present invention.

FIG. 40 is a top perspective view of the pump and module of FIG. 35, with certain portions of the module being transparent or removed for illustrative purposes.

DETAILED DESCRIPTION

In describing the preferred embodiments of the subject matter illustrated and to be described with respect to the drawings, specific terminology will be used for the sake of clarity. However, the invention is not intended to be limited to any specific terms used herein, and it is to be understood that each specific term includes all technical equivalents which operate in a similar manner to accomplish a similar purpose.

Figure 1:
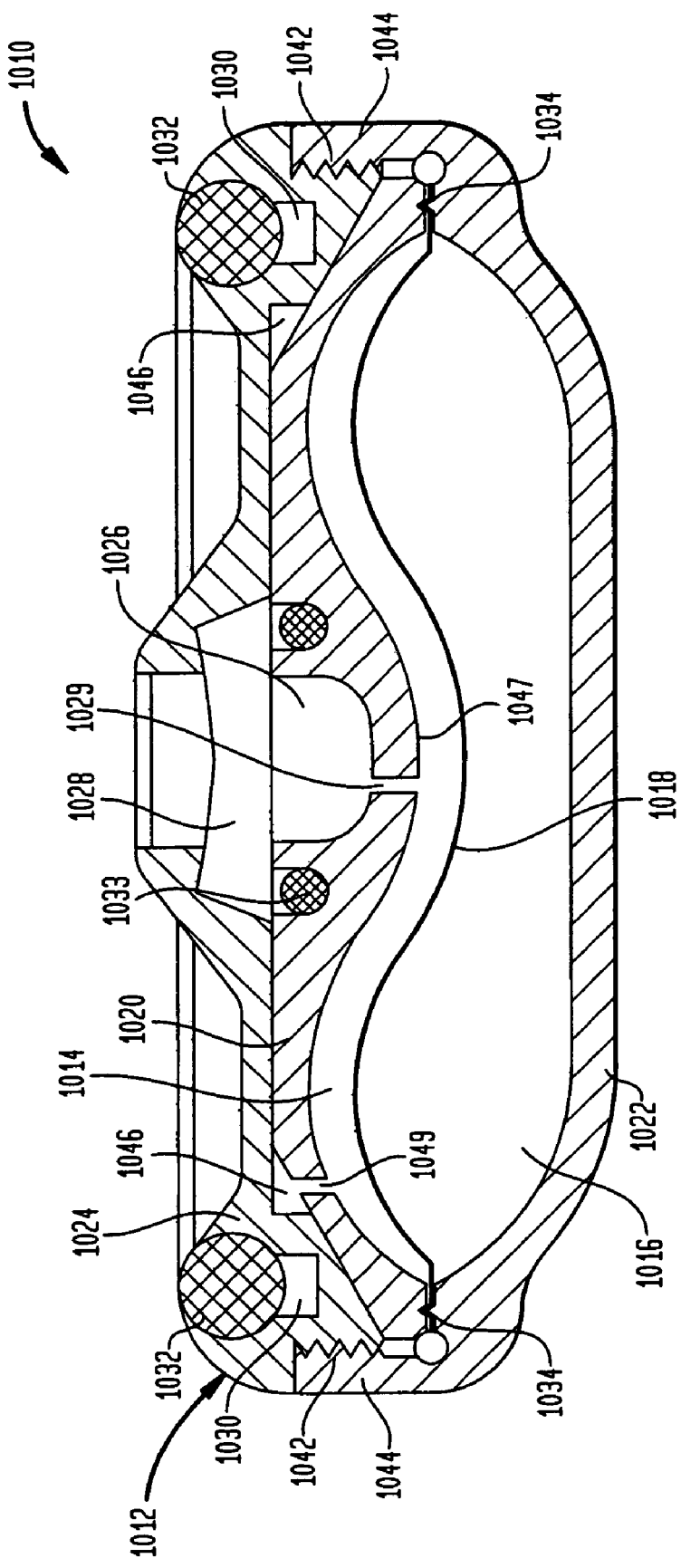
FIG. 1 is a cross sectional front view of a reduced size implantable pump in accordance with one embodiment of the present invention.
Figure 2:
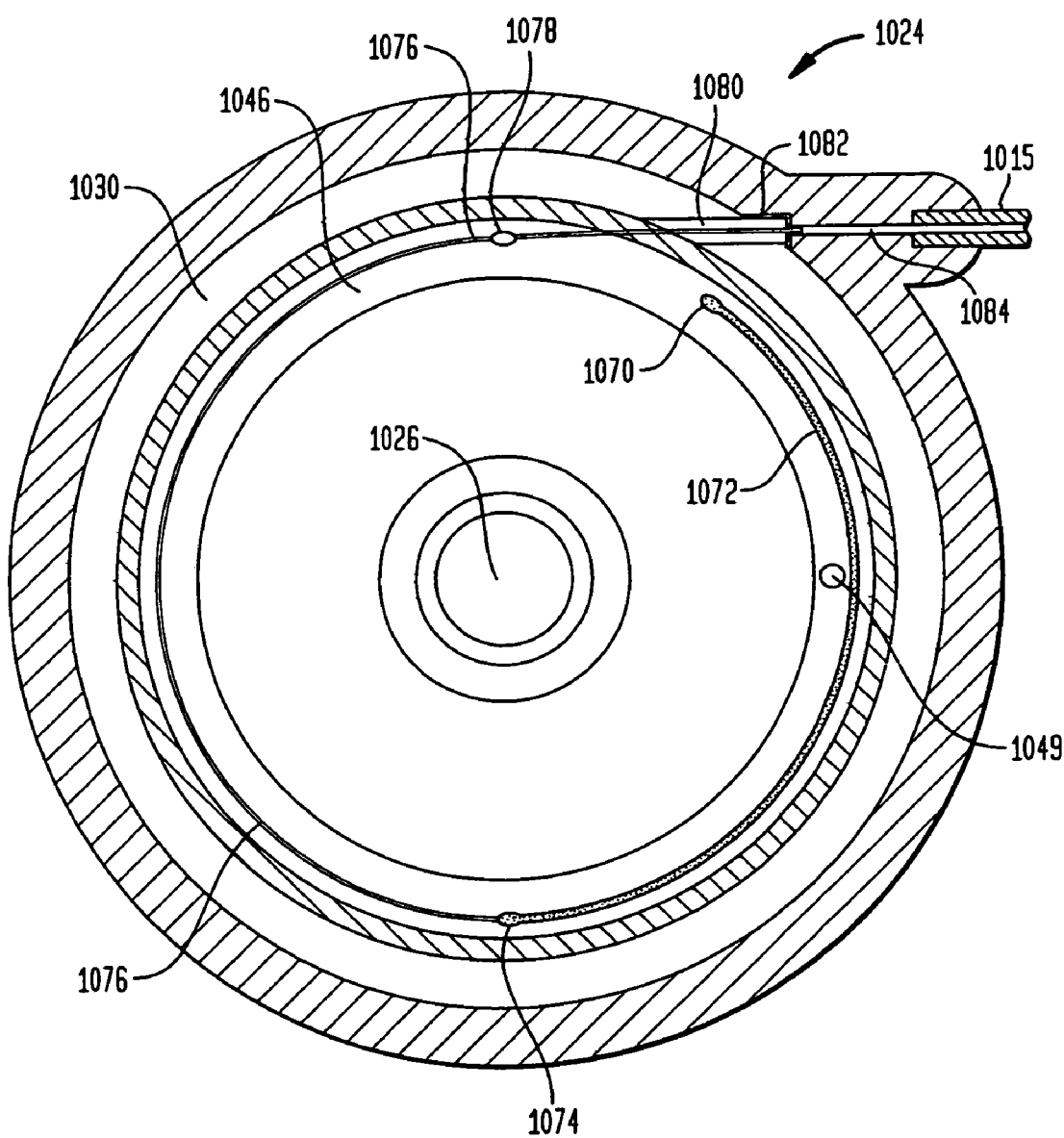
FIG. 2 is a cross sectional bottom view of a portion of the reduced sized implantable pump shown in FIG. 1.

Referring to the drawings, wherein like reference numerals refer to like elements, there is shown in FIGS. 1 and 2, in accordance with various embodiments of the present invention, a reduced size implantable pump designated generally by reference numeral 1010. In a preferred embodiment, pump 1010 is a constant flow pump including a housing 1012, which further defines an interior having two chambers 1014 and 1016. Chambers 1014 and 1016 are preferably separated by a flexible membrane 1018. It is noted that membrane 1018 may be of any design known in the art, for example, a membrane like that disclosed in commonly owned U.S. Pat. No. 5,814,019, the disclosure of which is hereby incorporated by reference herein. In a preferred embodiment, chamber 1014 is designed and configured to receive and house an active substance such as a medication fluid for the relief of pain, treatment of spasticity and neuro-mechanical deficiencies and the administration of chemotherapy, while chamber 1016 may contain a propellant that expands isobarically under constant body heat. This expansion displaces member 1018 such that the medication fluid housed in chamber 1014 is dispensed into the body of the patient through an outlet catheter 1015 (best shown in FIG. 2).

The design and configuration of housing 1012 is such that manufacturing and assembly of pump 1010 is relatively easy. Housing 1012 further includes separately manufactured top portion 1020, bottom portion 1022 and locking portion 1024. It is noted that in certain preferred embodiments, housing 1012 defines a substantially circular pump 1010. However, the housing may ultimately be a pump of any shape. In addition to the above described elements, pump 1010 also preferably includes replenishment port 1026 covered by a first septum 1028 that is in fluid communication with chamber 1014 through a channel 1029, an annular ring bolus port 1030 covered by a second septum 1032, and barium filled silicone o-ring 1033. Each of these elements will be discussed further below.

Referring to both FIGS. 1 and 2, where FIG. 2 is a cross sectional bottom view of locking portion 1024, the flow path of a medication fluid contained within chamber 1014 is shown. Upon the expansion of propellant contained within propellant chamber 1016 and the necessary displacement of membrane 1018, fluid contained in chamber 1014 is forced through an opening 1049 and into a cavity 1046, which will be further described below. As shown in FIG. 2, cavity 1046 extends in a circular fashion around pump 1010. Once in cavity 1046, the fluid may enter at any point along the length of a filter capillary 1072. Essentially, filter capillary 1072 is a well known type filter that allows for fluid to enter into its inner fluid path through permutation or the like. Thus, once a certain amount of fluid builds up within cavity 1046, it is capable of entering into filter 1072. This filter is preferably fixed and sealed in position by drops of glue or other adhesive located at 1070 and 1074. The fluid then travels through filter capillary 1072 until it exits into a resistor 1076. This resistor is preferably a long tube having a relatively small diameter, so as to dictate the maximum flow rate that may be achieved therethrough. In other words, the smaller the diameter of resistor 1076, the slower the flow rate of fluid traveling therethrough. Nevertheless, as more fully discussed below, resistor 1076 may be many different types of designs. The fluid within resistor 1076 then continues to an opening 1078 for a bridge 1080, which essentially allows resistor 1076 to cross over bolus port 1030. Thereafter, the fluid may continue through resistor 1076 and ultimately out catheter 1015. Epoxy or another suitable adhesive or sealant may be utilized to seal end 1070, end 1074 and opening 1078. Thus, fluid in cavity 1046 may only follow the path outlined above.

It is noted that FIG. 2 also depicts the flow path that fluid introduced through a bolus injection may take. Fluid may be injected into bolus port 1030 through the use of a device suitable for piercing septum 1032, such as a needle. Once in port 1030, which extends around pump 1010, fluid may enter a channel 1082. This channel extends at least partially around the above mentioned bridge 1080, and allows fluid injected into bolus port 1030 to ultimately exit catheter 1015 without passing through any portion of resistor 1076. As shown in FIG. 2, regardless of the path the fluid takes, it ultimately ends up in a passage 1084 just prior to catheter 1015. Thus, fluid coming from chamber 1014 may have one flow rate, while fluid directly injected into port 1030 may have a different flow rate, the latter preferably being greater.

Figure 3:
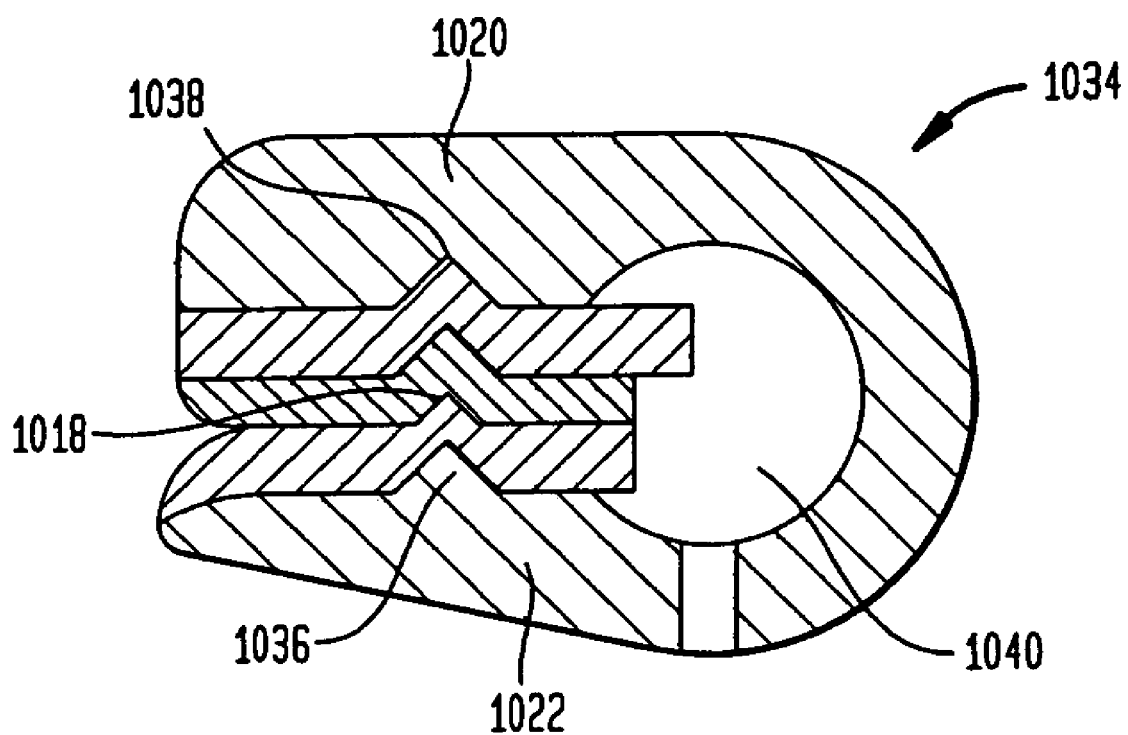
FIG. 3 is an enlarged view of an attachment area of the pump shown in FIG. 1.

The assembly of pump 1010 will now be discussed. It is noted that each of the individual elements/components of pump 1010 may be individually manufactured and thereafter assembled by hand or by another process, such as an automated process. As an initial step, top portion 1020 and bottom portion 1022 are placed or sandwiched together so as to capture membrane 1018 therebetween in an attachment area 1034 for fixably retaining same. As more clearly shown in the enlarged view of FIG. 3, attachment area 1034 comprises a projection 1036 located on bottom portion 1022, a depression 1038 located on top portion 1020, and a cavity 1040 formed through the cooperation of the two portions. In operation, the step of sandwiching together portions 1020 and 1022, with membrane 1018 disposed therebetween, causes projection 1036 to be forced into depression 1038. The portion of membrane 1018 disposed therebetween is thus also forced into depression 1038 by projection 1036. This causes a crimp-like connection, which fixably attaches and retains membrane 1018 within housing 1012. As shown in FIG. 3, membrane 1018 may consist of multiple layers, of which all are preferably "crimped" during the attachment process. Prior to pressing together portions 1020 and 1022, a layer of epoxy or other adhesive may be inserted into cavity 1040. In such embodiments that employ the use of an adhesive, the design may cause portions 1020 and 1022 to become fixably attached to one another upon the sandwiching of same. Further, the use of an adhesive within cavity 1040 may also aid in the fixation of membrane 1018 between the two portions. The epoxy or other adhesive may be placed into the cavity portion formed on either portion 1020 or portion 1022, prior to the sandwiching step.

Prior or subsequent to the assembly of top portion 1020 together with bottom portion 1022, o-ring 1033 or the like may be placed into a ring-shaped cavity formed in top portion 1022. In certain preferred embodiments, o-ring 1033 is a barium filled silicone o-ring, and is disposed around the area defining replenishment port 1026. Such an o-ring design allows for the area defining replenishment port 1026 to be illuminated under certain scanning processes, such as X-rays. As pump 1010 is implanted within the human body, locating port 1026, in order to refill the pump with medicament or the like, may be difficult. Providing a barium filled o-ring 1033, which essentially outlines the area of port 1026, allows for a doctor to easily locate the desired area under well known scanning processes. Other structures may be utilized, in which same also show up on different scans. The placement of o-ring 1033 is preferably accomplished by pressing the o-ring into an undersized channel that retains the o-ring, thereafter.

With o-ring 1033 preferably in place, locking portion 1024 is next attached to the other portions. It is noted that prior to attaching portion 1024, first septum 1028 should be inserted into locking portion 1024. Preferably, first septum 1028 is slid into a complimentary cavity formed in portion 1024, such that it remains within absent a force acting upon same. As first septum 1028 is designed to be captured between locking portion 1024 and top portion 1020, the septum should be placed prior to the attachment of locking portion 1024. In addition, as mentioned above, locking portion 1024 may include a second septum 1032 for covering bolus port 1030. In certain preferred embodiments, as shown in FIG. 1, second septum 1032 is ring shaped, and is pressed into locking portion 1024 in a similar fashion to that discussed above with relation to the placement of o-ring 1033. This may be done prior or subsequent to the attachment of locking portion 1024 to the other portions.

With regard to the attachment step, locking portion 1024 preferably includes a threaded area 1042 for cooperating with a threaded extension 1044. In operation, locking portion 1024 is merely screwed into engagement with bottom portion 1022. This necessarily causes top portion 1020, which is disposed between the two other portions, to be retained therebetween. In other words, the screw attachment of locking portion 1024 with bottom portion 1022 not only causes such portions to be fixably attached to one another, but also causes top portion 1020 to be fixably retained therebetween. It is noted that, depending upon how tight locking portion 1024 is screwed into 1022, portions 1020 and 1022 may be further pressed together, thereby increasing the fixation of membrane 1018 therebetween. Thus, pump 1010 is designed so that minimal connection steps are performed in order to cause all of the components thereof to be retained together. It is further noted that, in addition to the above discussed screw connection of portions 1022 and 1024, other attachment means may be utilized. For example, such portions may be snap fit together or fixed utilizing an adhesive. Finally, locking portion 1024 may be configured so as to form cavity 1046 between itself and top portion 1020. This cavity may be designed so as to allow for the injection of adhesive therein, thus increasing the level of fixation between the different portions of housing 1012. Additionally, cavity 1046 may house a flow resistor or the like, as will be more fully discussed below.

As set forth above, pump 1010 is configured and dimensioned to be relatively simplistic in both manufacture and assembly. However, pump 1010 is also configured and dimensioned so as to employ a significantly reduced overall size, while still providing for a useful amount of medicament and propellant to be housed therein. In the preferred embodiments depicted in the figures, top portion 1020 of pump 1010 includes an interior surface 1047 having an undulating or convoluted shape. More particularly, surface 1047 includes a convex central portion flanked by two concave portions. This configuration allows for the centrally located replenishment port 1026 and cooperating septum 1028 to be situated in a lower position with respect to the remainder of pump 1010. At the same time, the aforementioned flanking concave portions allow for the overall volume of chambers 1014 and 1016 to remain substantially the same as a pump employing an interior surface having one constant concave portion or the like. In other words, the flanking concave portions make up for the volume lost in situating port 1026 and cooperating septum 1028 in a lower position. Membrane 1018 is also preferably configured so as to have an initial undulating shape for cooperation with interior surface 1047. Thus, with no medicament or other fluid located within chamber 1014, membrane 1018 preferably rests against surface 1047. However, upon injection of fluid into chamber 1014, membrane 1018 adapts to the position shown in FIG. 1.

Figure 4:
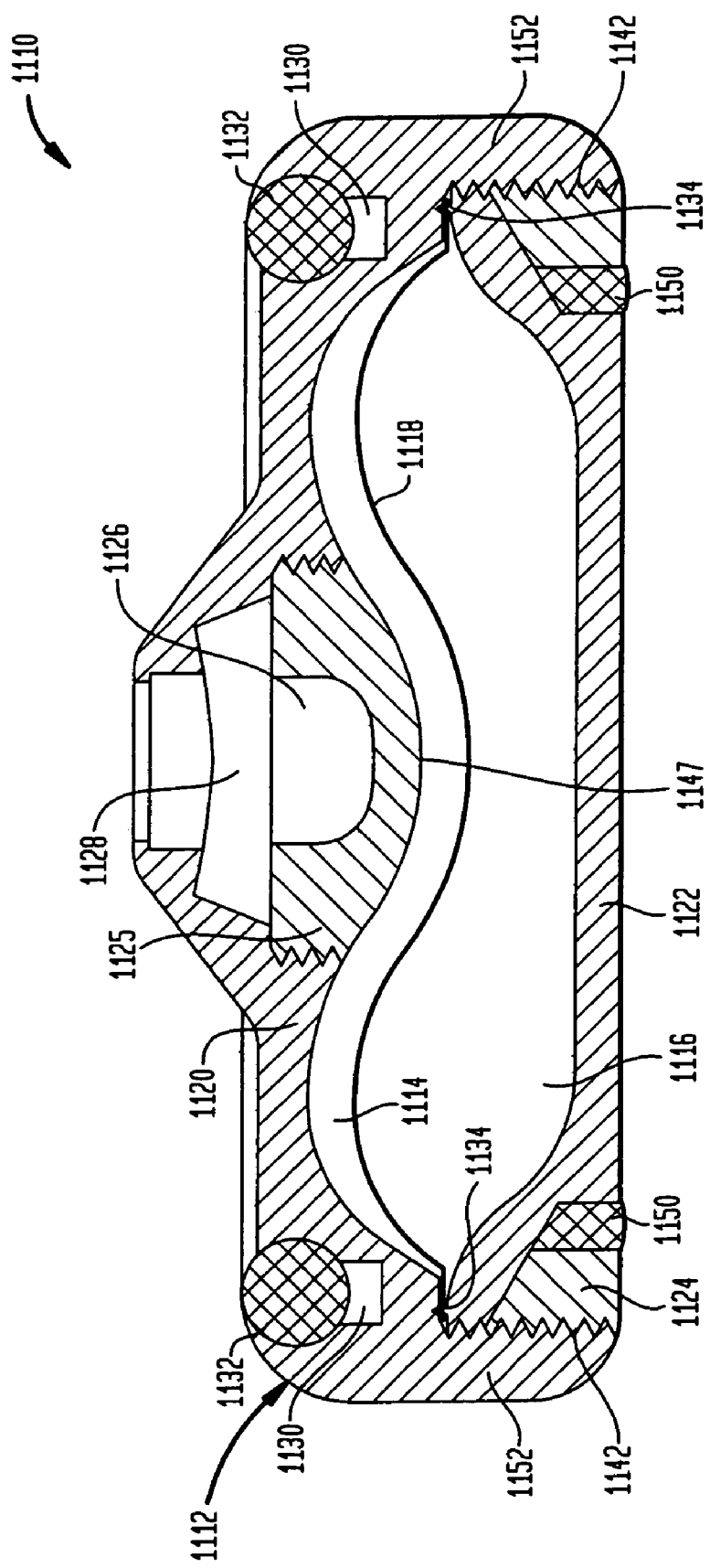
FIG. 4 is a cross section front view of a reduced size implantable pump in accordance with another embodiment of the present invention.

FIG. 4 depicts another reduced sized implantable pump designated by reference numeral 1110. As shown in the figure, pump 1110 includes several elements which are similar in structure and function to that of pump 1010. These elements are labeled with like references numerals within the 1100 series of numbers. For example, membrane 1118 is similar to the above described membrane 1018. In addition, pump 1110 operates in a similar fashion to that of pump 1010. Nevertheless, pump 1110 does include certain additional elements, as well as elements employing different constructions. Most notably, pump 1110 includes an additional component, namely septum retaining member 1125. This member is preferably adapted to be screwed into top portion 1120. Pump 1110 also includes a bottom o-ring 1150, but does not include a barium filled o-ring.

The assembly of pump 1110 also differs from that of pump 1010. As briefly mentioned above, initially, septum retaining member 1125 is first screwed into top portion 1120 in order to retain previously placed septum 1128 in place. Like the above described assembly of pump 1010, the assembly of pump 1110 then includes the step of sandwiching together portions 1120 and 1122, where membrane 1118 is likewise captured therebetween in attachment area 1134. However, in this embodiment, locking portion 1124 is adapted to engage top portion 1120, so that it is positioned on the bottom side of pump 1110. As shown in FIG. 4, top portion 1120 includes a threaded extension 1152 to cooperate and engage with threaded area 1142 of locking portion 1124. The screw connection between the two portions is similarly achieved. However, bottom o-ring 1150 is preferably situated between locking portion 1124 and bottom portion 1122. This o-ring both increases the force exerted on bottom portion 1122 by locking portion 1124, and also causes housing 1112 to retain a smooth exterior surface. The latter is important in implanting the pump within a patient, as rough or jagged surfaces may cause damage to tissue abutting the pump. Finally, it is noted that second septum 1132 may be pressed into top portion 1120, at any point during the assembly.

Figure 5:
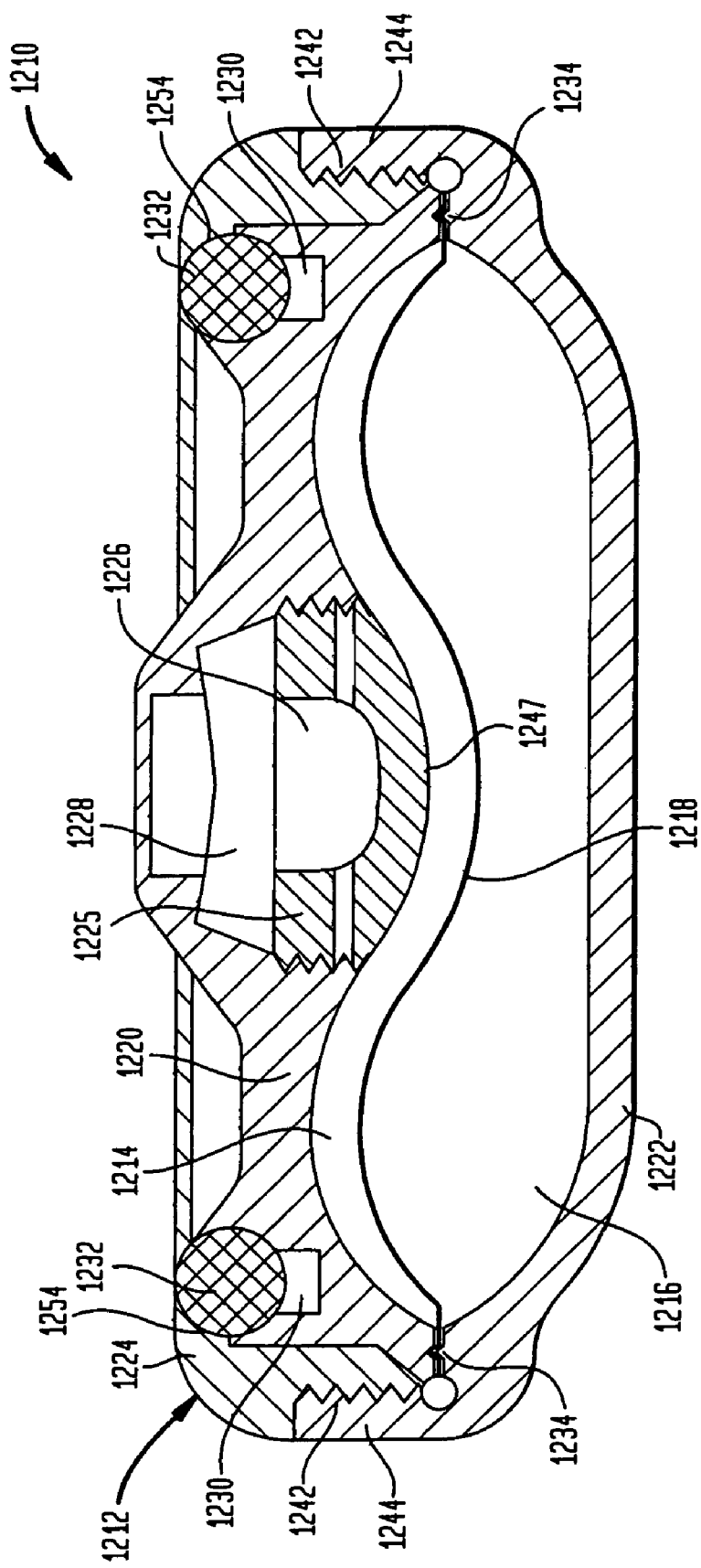
FIG. 5 is a cross section front view of a reduced size implantable pump in accordance with another embodiment of the present invention.

FIG. 5 depicts another reduced sized implantable pump designated by reference numeral 1210. As shown in that figure, pump 1210 includes several elements which are similar in structure and function to that of pumps 1010 and 1110. Once again, these elements are labeled with like reference numerals within the 1200 series of numbers. Nevertheless, pump 1210 does include certain additional elements, as well as elements employing different constructions. For example, like pump 1110, pump 1210 includes a septum retaining member 1225. Similarly, like pump 1010, pump 1210 utilizes a top mounting locking portion 1224, although it has a different construction.

The assembly of pump 1210 differs from that of the above discussed pumps 1010 and 1110. Like pump 1110, septum retaining member 1225 is first screwed into top portion 1220, in order to retain previously placed septum 1228 in place. Next, portions 1120 and 1222 are sandwiched together, thus capturing member 1218 within attachment 1234. Finally, locking portion 1224 is screwed into engagement with bottom portion 1222. Like the design of pump 1010, locking portion 1224 includes a threaded area 1242 which engages a threaded extension 1244 of bottom portion 1222. In addition to completing the assembly of pump 1210 by capturing bottom portion 1222 and forcing top portion 1220 towards bottom portion 1222, locking portion 1224 is configured and dimensioned in this embodiment to also capture second septum 1232. As shown in FIG. 5, locking portion 1224 includes a concave section 1254 for engaging septum 1232 upon the full engagement of portions 1222 and 1224.

Figure 6:
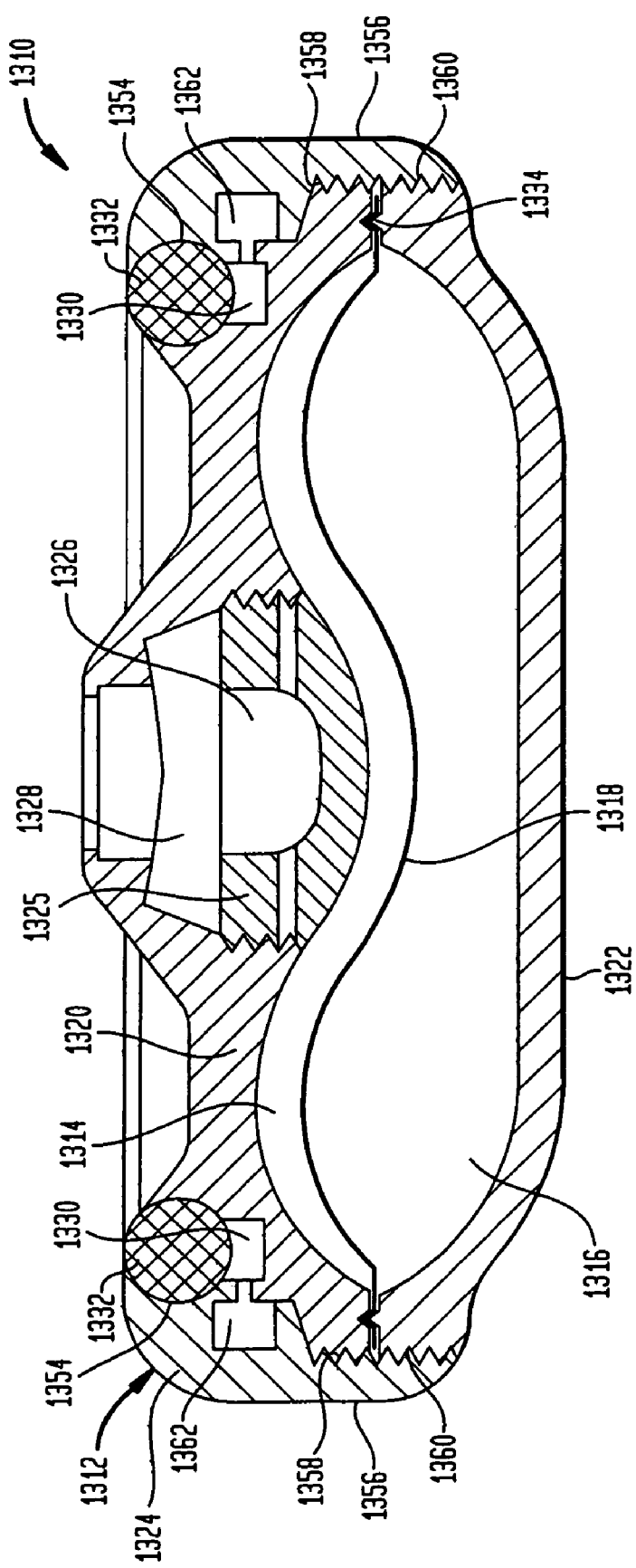
FIG. 6 is a cross section front view of a reduced size implantable pump in accordance with another embodiment of the present invention.

Yet another embodiment reduced sized pump 1310 is shown in FIG. 6. Like those pumps discussed above, pump 1310 preferably includes several elements which are similar in structure and function, and are thus labeled with like reference numerals within the 1300 series of numbers. Essentially, pump 1310 is akin to the configuration set forth in pump 1210. However, there are two main distinctions, namely, the cooperation of locking portion 1324 and portions 1320 and 1322, and the inclusion of a channel 1362 between locking portion 1324 and top portion 1320. In the embodiment depicted in FIG. 6, it is noted that locking portion 1324 includes a threaded extension 1356, which cooperate and engage threaded areas 1358 and 1360 of portions 1320 and 1322, respectively. Furthermore, locking portion 1324 preferably includes a channel 1362 formed therein. This channel may be adapted to cooperate with any of the chambers and/or ports discussed above. Additionally, channel 1362 may house other elements, such as a flow resistor or the like, which will be discussed more fully below.

Figure 7:
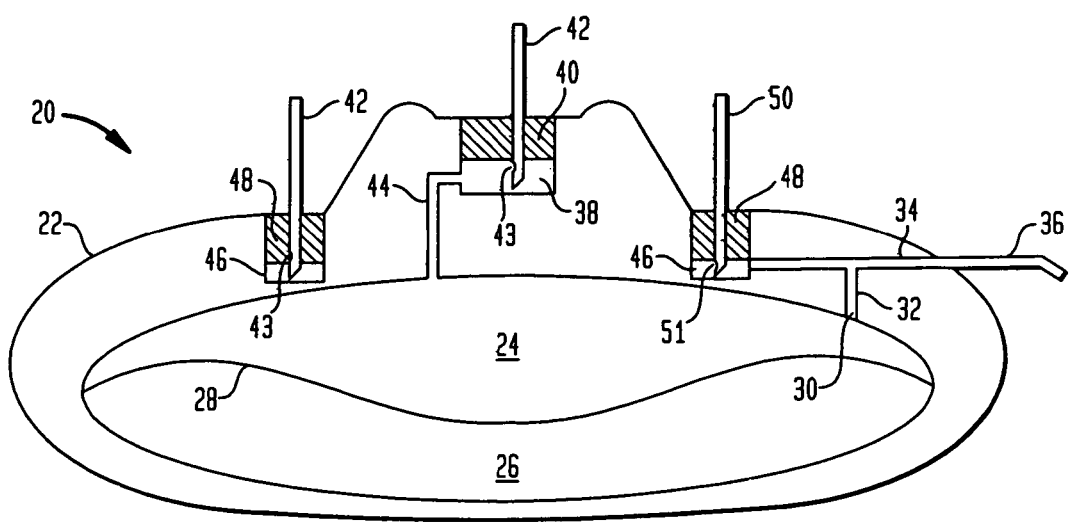
FIG. 7 is a cross sectional front view of an implantable constant flow pump for use in accordance with the present invention.

A second aspect of the present invention relates to providing a constant flow type implantable pump with infinitely variable flow capabilities. A mentioned above, such a construction may be beneficial to patients requiring more or less medication to be delivered by an implantable pump. While the different embodiments of this second aspect of the present invention may indeed be sized and configured to be utilized with any constant flow type implantable pump, preferred pumps will be described herein. In one preferred pump, as shown in FIG. 7 of the present application, the basic implantable pump design is designated as reference numeral 20. Pump 20 includes a housing 22 defining an interior having two chambers 24 and 26. Chambers 24 and 26 are separated by a flexible membrane 28. Chamber 24 is designed to receive and house the active substance such as a medication fluid for the relief of pain, treatment of spasticity and neuro-mechanical deficiencies and the administration of chemotherapy, while chamber 26 may contain a propellant that expands isobarically under body heat. This expansion displaces membrane 28 such that the medication fluid housed in chamber 24 is dispensed into the body of the patient through the path defined by an outlet opening 30, a resistor 32, an outlet duct 34 and ultimately an outlet catheter 36.

Resistor 32 provides a connection between chamber 24 and outlet duct 34. Thus, as mentioned above, a medication fluid flowing from chamber 24 to outlet catheter 36 must necessarily pass through resistor 32. This resistor allows for the control of the flow rate of the medication fluid, such that the flow rate is capable of being varied. Resistor 32 may be configured differently in many different embodiments, some of which are discussed below in the detailed description of the present invention. Essentially, resistor 32 defines a passageway for the flow of the medication fluid, where the passageway may be altered to thereby alter the flow rate of the medication fluid.

Implantable pump 20 also includes a replenishment port 38 covered by a first septum 40. Septum 40 can be pierced by an injection needle (such as needle 42 shown in FIG. 7) and, upon removal of such needle, is capable of automatically resealing itself. Septa of this type are well known to those of ordinary skill in the art. As implantable pump 20 is designed to medicate a patient over a limited period of time, replenishment port 38 is utilized for replenishing chamber 24 when empty or near empty. In operation, a physician or other medical professional inserts an injection needle 42 into an area of a patient's body where pump 20 is located, such that it may pierce septum 40. Thereafter, operation of the needle causes injection of the solution from the needle to pass into port 38, through passage 44, and into chamber 24. It is noted that the particular dimension and/or the patient's need may require such a process to be repeated at given intervals, for example, monthly, weekly, etc.

In addition to replenishment port 38, pump 20 also includes an annular ring bolus port 46 covered by a second septum 48. Essentially, this port allows for direct introduction of a solution into outlet catheter 36 and to the specific target area of the body. This port is particularly useful when a patient requires additional or stronger medication, such as a single bolus injection, and/or when it is desired to test the flow path of catheter 36. Such an injection is performed in a similar fashion to the above discussed injection into replenishment port 38. However, an injection into bolus port 46 bypasses passage 44, chamber 24 and resistor 32, and provides direct access to catheter 36. It is also contemplated to utilize bolus port 46 to withdraw fluid from the body. For example, where pump 20 is situated within the body such that catheter 36 extends to the vertebral portion of the spinal column, a needle with a syringe connected may be inserted into bolus portion 46 and operated to pull spinal fluid through catheter 36 and into the syringe.

In certain embodiments, septum 40 and septum 48 may be situated so that only specifically designed injection needles may be used to inject into the respective ports. For example, as is also shown in FIG. 7, septum 48 may be situated relatively close to the bottom of port 46 and septum 40 may be situated a greater distance away from the bottom of port 38. In this embodiment, injection needle 42 is provided with an injection eye 43, which is located above the tip of needle 42. Alternatively, injection needle 50 is provided with an injection eye 51 located at or near its tip. This arrangement prevents needle 42, which is typically utilized for replenishing chamber 24 with a long term supply of medication fluid, from being inadvertently used to inject its contents into bolus port 46. As is shown on the left side depiction of bolus port 46, needle 42 would have its eye 43 blocked by septum 48 if the needle is inadvertently inserted into this port. Needle 50, on the other hand, would be capable of injecting into port 46 because of the lower location of its eye 51. This is an important safety feature, as direct injection of a long term supply of medication fluid into port 46 could be dangerous. It is noted that needle 50 is also capable of injecting a solution into replenishment port 38, however, the same concerns (i.e.— over-medication) do not exist with respect to the filling of chamber 24, and as such medication housed in the chamber is slowly released. While this is one example of a possible safety feature with regard to the injection of materials into the pump, it is envisioned that other safety precautions may be utilized. For example, U.S. Pat. No. 5,575,770, the disclosure of which is hereby incorporated by reference herein, teaches a similar multiple injection needle system with additional valve protection. It is noted that such a safety needle system may be employed with regard to any of the various implantable pump embodiments disclosed herein. One of ordinary skill in the art would recognize the modifications required to utilize such a safety feature in the other discussed pump designs.

Figure 8:
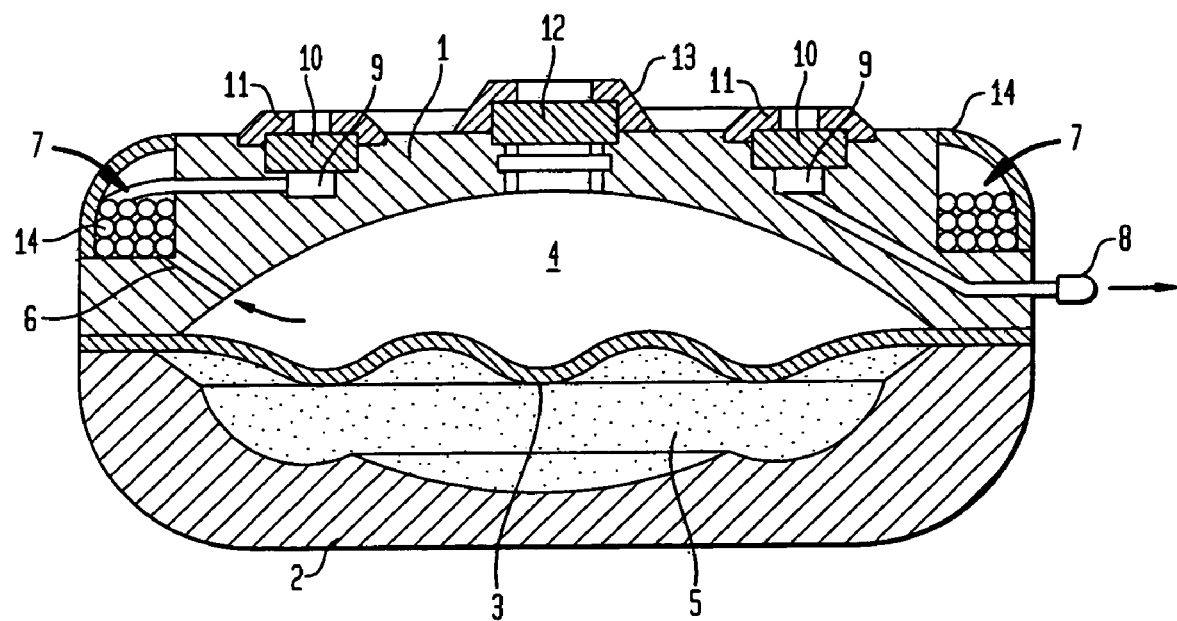
FIG. 8 is a cross sectional front view of another implantable constant flow pump for use in accordance with the present invention.

In other embodiments, the basic implantable pump design of the aforementioned '873 patent may also be utilized. As is discussed in its specification and shown in FIG. 8 of the present application, the '873 patent discloses a housing made up of two parts 1, 2 and an interior having two chambers 4, 5, which are separated by a flexible membrane 3. Chamber 4 is designed to receive and house the medication fluid, while chamber 5 may contain a propellant which, like that discussed in the above description of pump 20, expands isobarically under body heat. This expansion displaces membrane 3 such that the medication fluid housed in chamber 4 is dispensed into the body of the patient through the path defined by an outlet opening 6, an outlet reducing means 7 and ultimately an outlet catheter 8. It is noted that reducing means 7 is preferably a tube winding that wraps around part 1 of the housing. The resistor of the present invention, in certain embodiments, is preferably located at or near outlet opening 6. This will be discussed more fully below.

Prior to reaching outlet catheter 8, the medication fluid is introduced into a chamber 9 which is provided annularly on part 1 of the housing. Chamber 9 is sealed at its upper side by a ring or septum 10, which can be pierced by an injection needle and which automatically reseals upon withdrawal of the needle. This chamber is similar to the above discussed bolus port 46 of pump 20. In addition to allowing medication fluid from chamber 4 to pass into outlet catheter 8, chamber 9 also allows the direct injection of a solution into outlet catheter 8, the importance of which is discussed above. The aforementioned outlet reducing means 7 prevents a solution injected into the bolus port from flowing into chamber 4. In a similar fashion, when need be, chamber 4 may be replenished via a further septum 12. Once again an injection needle may be utilized for this purpose.

While two basic designs of implantable pumps are described above, it is noted that other designs may include different or additional elements. Similarly, while the above description teaches two implantable pumps that may be utilized in accordance with the present invention, other implantable pump designs are also capable of being utilized. For example, U.S. Pat. Nos. 5,085,656, 5,336,194, 5,722,957, 5,814,019, 5,766,150, 5,836,915 and 6,730,060, the disclosures of which are all hereby incorporated by reference herein, may be employed in accordance with the present invention. In addition, one specific embodiment will be discussed below.

As mentioned above, the capability of varying the flow rate of an implantable pump is desired. In the above discussed constant flow pumps, the flow rate of the medication fluid depends upon the pump pressure, the pressure at the end of the catheter and the hydraulic resistance of any of the capillaries or other passages that the medication fluid must travel through. With regard to the resistance of the capillaries, such resistance depends upon the geometry of the capillary itself, as well as the viscosity of the medication fluid. This viscosity, as well as the pump pressure, may both be influenced by body temperature. As such, one instance in which it is desired to control the flow rate of the pump exists if the patient develops a fever because the flow rate of the infusion device may be affected in an undesired way.

Another example of when the variable flow rate of the implantable pump is desired relates to the condition or active status of the patient. For example, especially in the case where painkillers are being administered, it may be advantageous to deliver less medication during the nighttime hours, when the patient is sleeping. Additionally, as discussed above, it may be desirable to be able to increase the dosage of such painkillers or the like when the patient's symptoms worsen. Increasing of the flow rate of the medication fluid may be necessary in order to diminish the patient's pain level. In accordance with the present invention, the aforementioned resistor 32 is useful for adjusting the flow rate in order to counteract undesirable flow rate changes due to body temperature changes, and to allow for desired adjustments of flow rate to treat heightened or worsened symptoms.

In a first embodiment this adjustment of flow rate is realized by adjusting the cross-sectional geometry of an article of the resistor. It is noted that the first embodiment will be discussed with respect to pump 20; however, it may be utilized in combination with any implantable pump. As shown in FIGS. 9-15, in accordance with this first embodiment, resistor 32 includes an elastic and resilient filament 52 situated in a resistor capillary 54, where resistor capillary 54 provides a connection between outlet opening 30 and outlet capillary 34. Capillary 54 may be situated so as to constitute substantially the entire outlet capillary 34, or may only be a portion thereof. Essentially, capillary 54 need only require the aforementioned medication fluid to pass therethrough, and thus, may be any length suitable for use in varying the flow rate.

Figure 9:
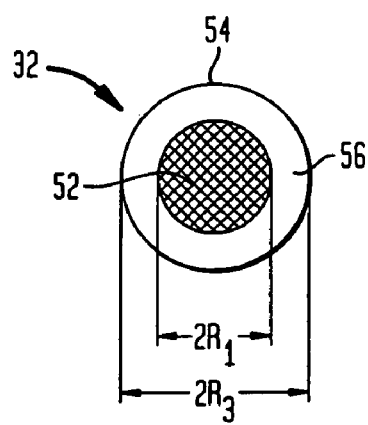
FIG. 9 is a cross sectional view of a variable flow resistor in accordance with a first embodiment of the present invention having a filament located concentrically in a capillary.

FIGS. 9, 10a and 10b show a first example of the first embodiment resistor 32, where elastic filament 52 is located concentrically in resistor capillary 54. This configuration forms a ring-shaped flow channel 56 through which fluid flows in a direction shown by arrow F. As is best shown in FIG. 10a, filament 52 includes a first end 58 attached to a stationary attachment 60, and a second end 62 attached to a movable attachment 64. Resistor 32 also has an effective length L extending between capillary entrance 66 to exit 68, and an initial diameter D1 (i.e.—2 times its radius R1). Additionally, capillary 54 has a diameter D3 (i.e.—2 times its radius R3). This will be similar throughout in the various other capillaries discussed herein.

In this example, movable attachment 64 is capable of moving in the opposite longitudinal directions shown by arrows A and B, while attachment 60 remains stationary. In operation, movement of attachment 64 in the direction of arrow B increases the distance between attachments 62 and 64 and also results in the decrease of the initial diameter Dl to a lesser diameter D2 (i.e.—2 times its lesser radius R2) This is best shown in FIG. 10b. The decrease of the diameter of filament 52 from D1 to D2 increases the size of channel 56 and thus necessarily decreases the hydraulic resistance in capillary 54. Oppositely, movement of attachment 64 in the direction of arrow A returns filament 52 to the position shown in FIG. 10a, and increases the hydraulic resistance in capillary 54. A filament of this type may be constructed of silicone rubber, or other suitable polymer materials for providing the required elasticity and resiliency so as to return to its original shape and size after being deformed by stretching. Similarly, although filament 52 is shown in the figures as having a substantially circular cross section, it is envisioned that filaments having other cross sections may be utilized, for example, polygonal, oval, square and the like.

As the inner diameter of capillary 54 is typically very small (on the order of several thousands of millimeters), it is often difficult to locate filament 52 directly in the center of the capillary. FIGS. 11a, 11b, 12a and 12b depict a second example where elastic filament 52 touches the inner wall of capillary 54 (i.e.—an eccentric position). This eccentrically placed filament 52 creates a sickle-shaped flow channel 56, as opposed to the ring-shaped flow channel of the first example. This second example also differs from the first example discussed above, in that both ends 58, 62 of filament 52 are attached to movable attachments 60, 64, respectively. This is useful, as in operation, one movable attachment (or the mechanism moving it) may fail. The two movable attachment design provides a failsafe, thereby allowing filament 52 to be stretched through the movement of the non-failing attachment. Attachment 64 is still capable of moving in the direction depicted by arrows A and B and attachment 60 is capable of moving in the direction depicted by arrows A' and B'.

In operation, movement of either of attachments 60, 64 in the directions B' and B, respectively, decreases the diameter D1 to a lesser diameter D2 (once again, these diameters refer to two times the radii R1 and R2, respectively). This position is best shown in FIG. 12b. Like that of the above discussed first example, this decrease in the diameter of filament 52 from D1 to D2 increases the size of channel 56 and thus necessarily decreases the hydraulic resistance in capillary 54. Oppositely, movement of either of attachments 60, 64 in the direction of arrows A' and A, respectively, returns filament 52 to the position shown in FIG. 12a, and increases the hydraulic resistance in capillary 54.

Attachment 64 in the first example, and attachments 60, 64 in the second example may be moved by any means known to those of ordinary skill in the art. For example, it is well known to utilize motors such as micro-motors, magnets, or other hydraulic, electrical or mechanical actuators. One example of a suitable motor assembly is sold under the designation X15G by Elliptec Resonant Actuator of Dortmund, Germany.

In accordance with the present invention, it is known to design a capillary with a circular lumen defined by a rigid wall. Essentially, this type of apparatus is a hollow tube having a flow therethrough (i.e.—the present design without filament 52). For such a design, the flow rate can be calculated using the well-known Hagen-Poisseuille Equation:

$$V = (\Delta p \pi R_2^4)/(8\eta L)$$

Where:
V=flow rate
Δp=pressure difference between entrance 66 and exit 68 of capillary 54.
η=viscosity of fluid.
L=effective length L of resistor 32.
$R_2$=radius of resistor capillary 54 (see in FIG. 9).

As shown in the above equation, small changes in the diameter of a capillary have a profound effect on the flow rate. However, the modification of the $R_2$ dimension is often technically very difficult to realize. Thus, as discussed above, the design of this first embodiment of the present invention includes implementing elastic filament 52 into resistor capillary 54, as discussed above. For the first example of the first embodiment (i.e.—concentrically located filament 52), the following equation may be utilized in determining the flow rate of this design:

$$V = [(\Delta p \pi)(R_2 - R_1)^3(R_2 + R_1)]/(8\eta L)$$

Where:
V=flow rate
Δp=pressure difference between entrance 66 and exit 68 of capillary 54.
η=viscosity of fluid.
L=effective length L of resistor 32.
$R_1$=radius of filament 52 (see in FIG. 9).
$R_2$=radius of resistor capillary 54 (see in FIG. 9).

Alternatively, for the second example of the first embodiment (i.e.—eccentrically located filament 52), the following equation may be utilized in determining the flow rate of this design:

$$V = [(\Delta p \pi)(R_2 - R_1)^3(R_2 + R_1)2.5]/(8\eta L)$$

Where:
V=flow rate
Δp=pressure difference between entrance 66 and exit 68 of capillary 54.
η=viscosity of fluid.
L=effective length L of resistor 32.
$R_1$=radius of filament 52 (see in FIG. 9).
$R_2$=radius of resistor capillary 54 (see in FIG. 9).

All three of the above equations are well known in the field of fluid dynamics. Further, while the effective length L of resistor 32, as best shown in FIGS. 10a and 12a, corresponds to the length of capillary 54, it is noted that the effective length more specifically relates to the length of capillary 54 in which filament 52 resides. Therefore, the effective length L, for use in the above equations, may be less than the length of capillary 54 if filament 52 has a length less than the length of capillary 54. It is noted that these equations apply to the use of capillaries and filaments having circular cross sections. Other embodiments may utilize differently shaped capillaries and filaments. For these embodiments, separate equations must be utilized.

Figure 11A:
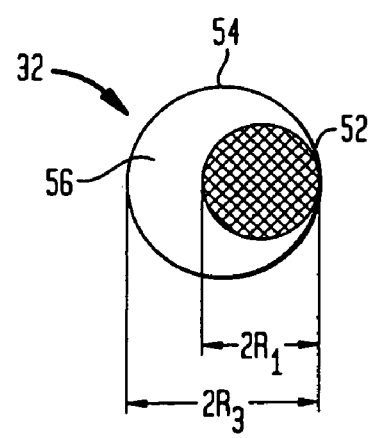
FIG. 11a is a cross sectional view of a variable flow resistor of the present invention having a filament located eccentrically in a capillary.
Figure 11B:
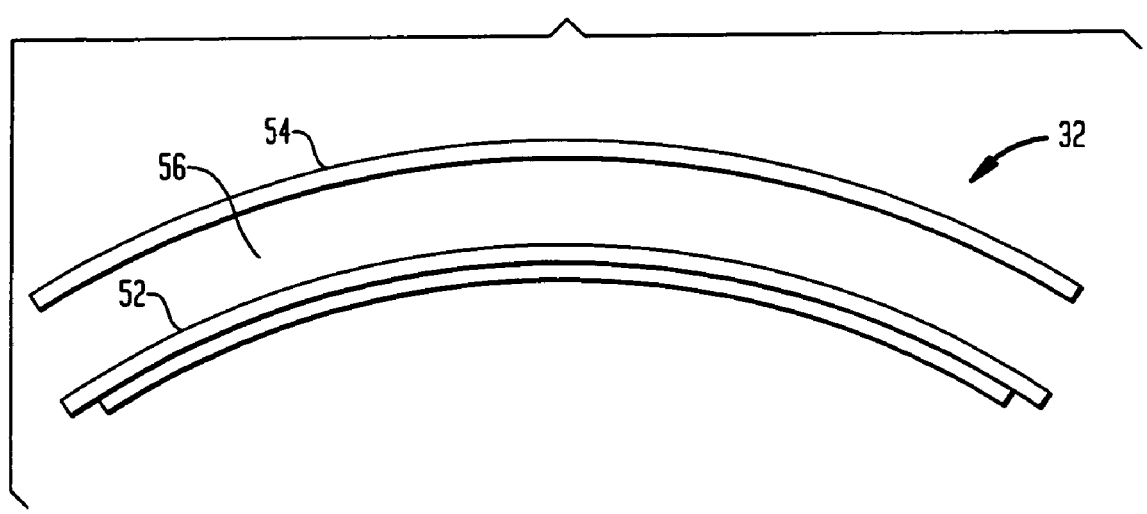
FIG. 11b is a longitudinal cross sectional view of the variable flow resistor of FIG. 11a, depicting the curvature of the capillary.

As is clearly shown by the second equation, situating filament 52 in the offset position with relation to the center of capillary 54 of, as shown in FIG. 11a, allows the flow rate to be changed by a factor of 2.5. Therefore, for applications where it is desired to vary the flow rate by such a ratio, it is possible to merely move filament 52 from a central position taught in the first example (as shown in FIG. 9) to the eccentric position taught in the second example (as shown in FIG. 11a). However, often times, it is typically desired to vary the flow rate by a factor of 25 or more. In order to achieve such a flow rate change, one may utilize an elastic filament 52 as discussed above, situated in an offset position. Typically, to ensure that filament 52 remains in the offset position, a curved capillary 54 is utilized. As shown in FIG. 11b, filament 52 remains eccentrically placed within capillary 54 because of the curvature of the capillary. As filament 52 is generally elastic and resilient, it easily conforms to any curvature of capillary 54.

A realistic range for the change in diameter of elastic filament 52 is approximately from its original size to about seventy percent of its original size (i.e.—a 1 to 0.7 ratio). Calculations have been carried out using the above equation relating to the eccentrically positioned filament 52. For example, with the initial radius R1 of filament 52 being approximately eighty percent (80%) of the radius R2 of capillary 54 (i.e.—a 0.8 to 1 ratio) and the maximal elongation of filament 52 giving a radius R3 that is approximately fifty six percent (56%) of the radius R2 of capillary 54 (i.e.—a 0.56 to 1 ratio), it was calculated the ratio of flow rate between the non-elongated state and the maximal elongated state is approximately 9.20 to 1. With the initial radius R1 of filament 52 being approximately eighty five percent (85%) of the radius R2 of capillary 54 (i.e.—a 0.85 to 1 ratio) and the maximal elongation of filament 52 giving a radius R3 that is approximately fifty nine point five percent (59.5%) of the radius R2 of capillary 54 (i.e.—a 0.595 to 1 ratio), it was calculated the ratio of flow rate between the non-elongated state and the maximal elongated state is approximately 17.00 to 1. Finally, with the initial radius R1 of filament 52 being approximately ninety percent (90%) of the radius R2 of capillary 54 (i.e.—a 0.9 to 1 ratio) and the maximal elongation of filament 52 giving a radius R3 that is approximately sixty three percent (63%) of the radius R2 of capillary 54 (i.e.—a 0.63 to 1 ratio), it was calculated the ratio of flow rate between the non-elongated state and the maximal elongated state is approximately 43.46 to 1. Thus, using a filament 52 having a radius R1 between approximately eighty five percent (85%) and ninety percent (90%) of the total radius R2 of capillary 54, would result in a flow rate variation of approximately 25. From the foregoing, one can calculate the desired flow rate variation based on the known geometry of the flow resistor.

A third example of the first embodiment of the present invention is shown in FIG. 13. This example includes a capillary 154 that is divided into two sectors by a center wall 155. Fluid is capable of flowing through capillary 154 by entering through entrance 166 and exiting through exit 168, as depicted by fluid flow arrow F. An elastic filament 152 is fixed at its ends by fixation points 160 and 164, and is wrapped around a magnetic element 170 at the approximate central portion of filament 152. Repulsive magnetic forces are transmitted to magnetic element 170 by a corresponding magnetic counterpart 172, having a similar polarity. Thus, movement of counterpart 172 results in the like movement of element 170. Counterpart 172 may be located in a hermetically sealed housing 174, or the like. Movement of the magnetic element in a direction indicated by arrow B will, as in the above discussed examples, cause the diameter of filament 152 to shrink, thereby allowing for the increase in flow rate. Similarly, movement of element 170 in the direction indicated by arrow A will decrease the flow rate. It is noted that this two sector design includes two capillary and filament relationships for use in varying the flow rate. As such, where both the capillary and the filament have circular cross sections, two separate calculations in accordance with the above discussed equations, must be conducted to determine the overall hydraulic resistance provided by the system.

Further, in accordance with this third example of the first embodiment, it is envisioned that magnetic element 170 and magnetic counterpart 172 may be oppositely polarized, such that they are attracted to one another. In this type of design, moving counterpart 172 in a direction closer to element 170 would cause the attraction between them to be greater. Thus, if counterpart 172 is located below element 170 (as opposed to that shown in FIG. 13), movement of counterpart 172 towards element 170 would increase the magnetic attractive force between the two components and necessarily cause the movement of element 170 in the direction indicated by arrow B. As discussed above, this lengthens filament 152, while at the same time decreasing its diameter. Thus, this would constitute one alternate design. Similarly, it is possible to provide a single magnetic component with a corresponding metallic component, rather than the above discussed two magnet configuration. Clearly, as is well understood, such components would be attracted to one another. Therefore, operation of this magnet/metal configuration would operate in a like manner to the above discussed opposite polarity magnetic configuration. However, it is to be understood that various configurations are envisioned depending upon the polarity of the magnetic components and/or the situation of the metallic element and its corresponding magnetic element. For example, filament 152 may be wrapped around a metallic element, with a magnetic component located in housing 174 or vice versa.

Figure 15:
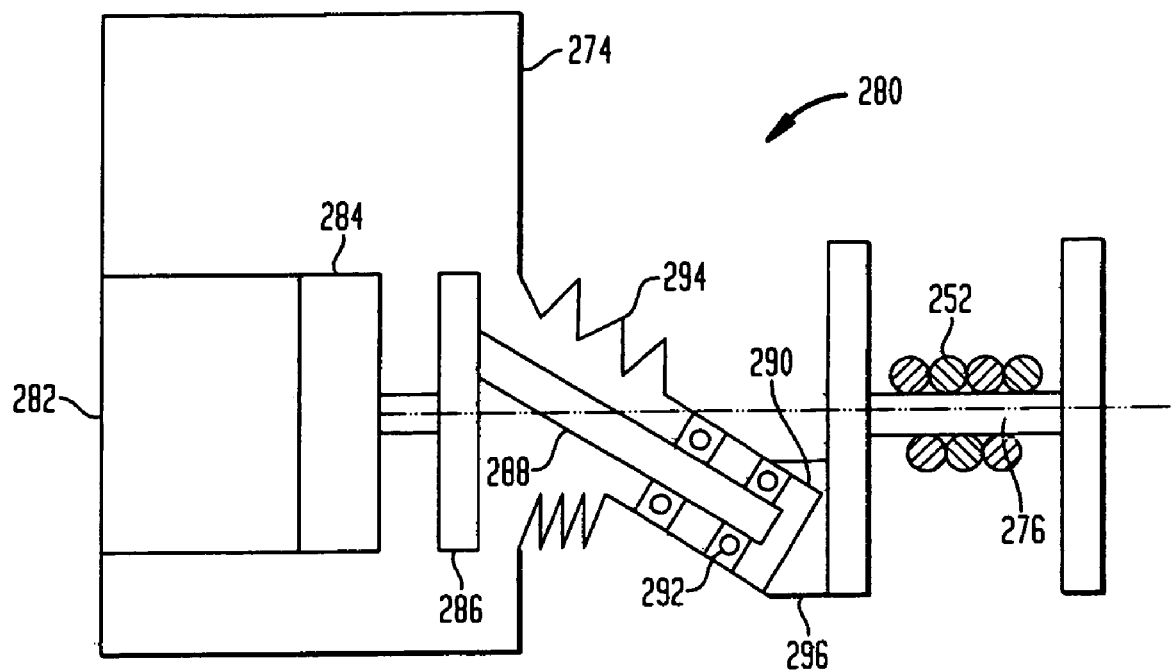
FIG. 15 is a cross sectional view of the driving assembly for use with the flow resistor of FIG. 14.

A fourth example of the first embodiment of the present invention is shown in FIG. 14. This example includes an elastic filament 252 that is fixed at one end by attachment 260 and wrapped around axle 276 on the other. Once again, fluid enters capillary 254 at entrance 266, and exits at exit 268. Fluid flow direction is once again indicated by arrow F. Rotation of axle 276, in a direction depicted by arrow W (i.e.— counter-clockwise), causes filament 252 to lengthen, while its diameter reduces. This, in turn, increases the possible flow rate through capillary 254. Alternatively, rotation of axle 276 in a clockwise direction causes the opposite effect. As previously mentioned, if filament 252 and filament 254 have circular cross sections, the above equations may be utilized in calculating the hydraulic resistance of the system. Axle 276 may be driven directly by a micro motor, via a reduction gear drive assembly 280 as shown in FIG. 15.

While other means may be utilized for driving axle 276, the following sets forth a discussion of the aforementioned reduction gear drive assembly 280. As shown in FIG. 15, assembly 280 presents a solution for the transfer of rotational motion from hermetic enclosure 274 to axle 276. Assembly 280 includes a motor 282 that is augmented by a gear drive 284 and transferred to disc 286. The disc includes a shaft 288 which is preferably positioned at an angle which is less than ninety degree relative to the plane of disc 286. Shaft 288 extends into cylindrical portion 290 of hermetic enclosure 274. Further, shaft 288 is supported via bearings 292 within cylindrical portion 290. Finally, cylindrical portion 290 is connected to enclosure 274 by an elastic connection 294 and is capable of transmitting forces via pusher plate 296 to rotate axle 276. Essentially, the offset nature of the connections between disc 286 and shaft 288, and portion 290 and plate 296, coupled with the elastic nature of the connection between enclosure 274 and portion 290 allows for the rotation of axle 276. It is noted that operation of the motor in different directions causes the rotation of the axle in the clockwise or counter-clockwise direction.

Gear drive assembly 280 is useful for allowing a relatively small or weak motor to drive axle 276. Providing a gear assembly to better utilize a motor is well known. However, any known gear assembly, suitable for use with the present invention, may be employed. Further, it is also contemplated that a suitable motor may be employed that may be capable of directly rotating axle 276. Essentially, in a design like this, axle 276 may be a continuation of the drive shaft of the motor.

Any of the examples set forth in the discussion relating to this first embodiment may include different, additional or fewer elements. Such revisions will be understood by those of ordinary skill in the art. For example, it is envisioned that the various elastic filaments, while shown in the figures having a substantially circular cross section, may include any shaped cross section. Similarly, although shown as substantially straight, the above may be utilized in conjunction with curved capillaries. Additionally, it is to be understood that the inventions set forth in the first embodiment may be utilized with any known implantable pump. The particular pump design may require the use of a resistor that is particularly configured and dimensioned to operate with the pump. Such design requirements are evident to those of ordinary skill in the art.

Figure 16:
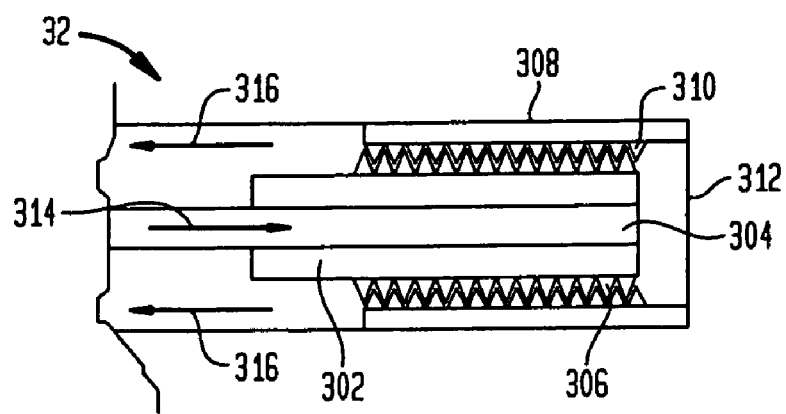
FIG. 16 is a cross sectional view of a variable flow resistor in accordance with a second embodiment of the present invention in a high resistance position.
Figure 17:
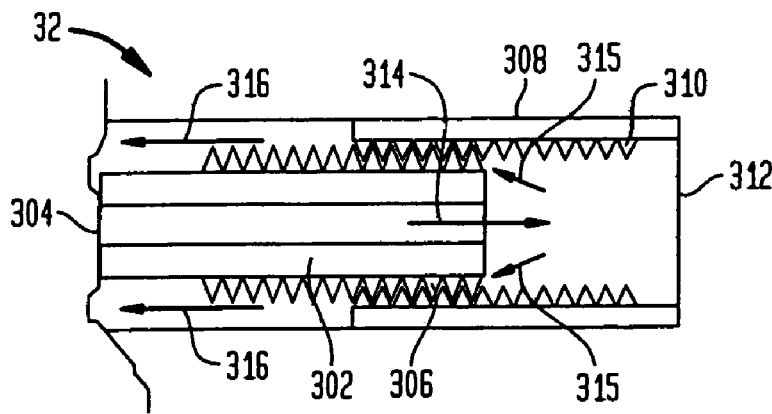
FIG. 17 is a cross sectional view of the variable flow resistor of FIG. 16 in a low resistance position.

In a second embodiment the adjustment of flow rate is realized by providing a pair of threaded matched cylinders for use as resistor 32. Once again, the second embodiment will be discussed with respect to pump 20; however, it may be utilized in combination with any implantable pump. As shown in FIGS. 16 and 17, in accordance with this second embodiment, resistor 32 includes a first threaded member 302 having a hollow interior 304 and a threaded exterior 306. First threaded member is disposed in second threaded member 308, which is an oppositely configured hollow member having a threaded interior surface 310 and a closed end 312. The threaded cooperation between first and second threaded members 302 and 308 allows for the first member to be disposed within the second member at varying levels, therefore, allowing for different overlaps of the two members. For example, FIG. 16 depicts the first member being substantially disposed within the second member, while FIG. 17 depicts the first member being only partially disposed within the second member.

In operation of this second embodiment, fluid is introduced into hollow interior 304 in the direction indicated by arrow 314. Upon the sufficient build up of pressure created by the flow of the fluid, the closed end 312 design of second member 308 forces the fluid to move in the direction indicated by arrow 315 (best shown in FIG. 17) and through the flow channel defined by the threaded configuration of the two members 320, 308. The degree of overlap of the two threaded geometries determines the hydraulic resistance, and thus the flow rate of the fluid. Therefore, the high overlap shown in FIG. 16 would result in a lesser flow rate than that of the low overlap depicted in FIG. 17. Nevertheless, the fluid ultimately emerges from the resistor design as illustrated by arrows 316. It is envisioned that in other examples in accordance with this embodiment of the present invention the shapes of the two members may vary, as can the particular thread design employed.

Figure 18:
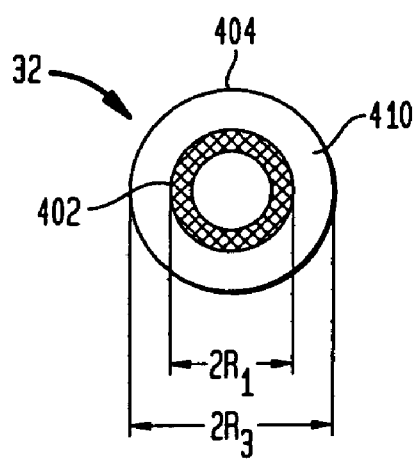
FIG. 18 is a cross sectional view of a variable flow resistor in accordance with a third embodiment of the present invention with an insert centrally located.
Figure 19:
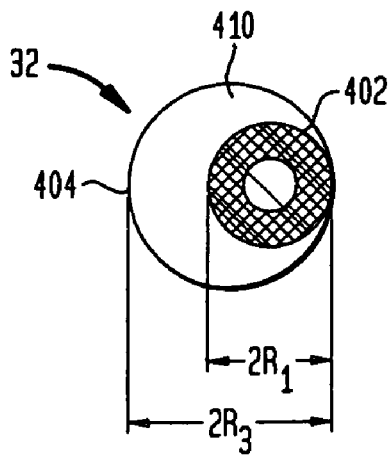
FIG. 19 is a cross sectional view of a variable flow resistor in accordance with a third embodiment of the present invention with an insert eccentrically located.
Figure 20:
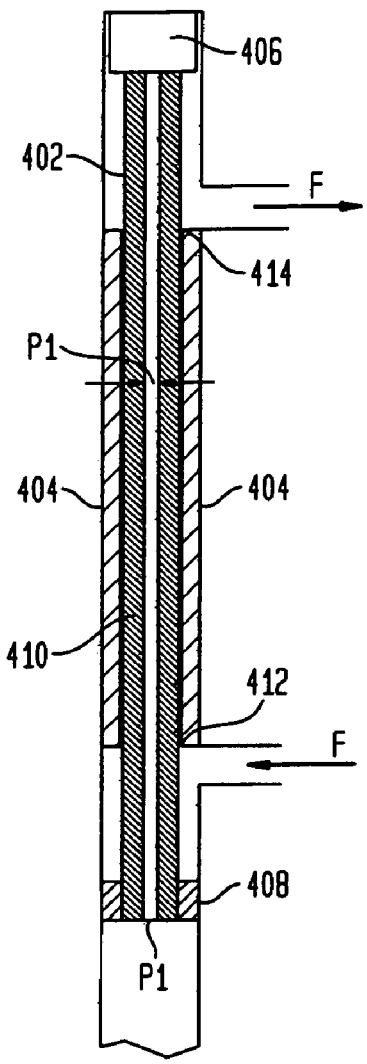
FIG. 20 is a longitudinal cross sectional view of the variable flow resistor of FIG. 18.

In a third embodiment the adjustment of flow rate is realized by adjusting the cross-sectional geometry of the resistor. However, unlike the above discussed first embodiment where the cross-sectional geometry is adjusted by lengthening filament 52 in order to decrease its diameter, this third embodiment varies the cross-sectional geometry of a tube 402 by changing its internal pressure. Once again, the third embodiment will be discussed with respect to pump 20; however, it may be utilized in combination with any implantable pump. As shown in FIGS. 18-20, in accordance with this third embodiment, resistor 32 includes an elastic tubular element 402 disposed in a capillary 404. As best shown in FIG. 20, the tubular element 402 extends through capillary 404 and is fixed at its ends by sealing elements 406 and 408. As shown in FIGS. 18 and 20, the tubular element 402 is situated so as to define a ring-shaped flow channel 410 through capillary 404. However, like the above discussed first embodiment, the tube may be positioned eccentrically, thereby forming a sickle-shaped flow channel 410, as shown in FIG. 19.

In operation, fluid flows in the direction indicated by arrows F, and is subjected to the flow channel from entrance 412 to exit 414. Once again, the effective length of the resistor extends along the portion where tube 402 and capillary 404 overlap. The diameter of tubular element 402 depends upon its internal pressure P1. Thus, the flow rate of the fluid can be affected by pressure being applied or reduced to the inside of tube 402. Rising the pressure will increase the outer diameter of the tubing and thus will have the effect of reducing the flow rate. Similarly, lowering the pressure will decrease the outer diameter of the tubing and increase the flow rate. It is noted that tubular element 402 will have a particular resting diameter (i.e.—with no pressure being applied). The design of this third embodiment will be subject to the flow rate calculations discussed above in relation to the first embodiment. Specifically, in the design shown in FIG. 19, adjusting the tubing between approximately eighty five percent (85%) to ninety percent (90%) of the overall inner diameter of capillary 404 will result in an approximate flow rate variation of 1 to 25, which is the desired ratio for an implantable pump. However, it is to be understood that the operation of this third embodiment will be substantially opposite to that of the first embodiment. Clearly, rather than decreasing the diameter of tube 402 from its resting diameter, this third embodiment aims to increase the diameter. Thus, operation of tube 402 will move the system from a state in which the flow rate is greater to a state where the flow rate is lesser. This is contrary to the first embodiment.

Any means suitable for rising and lowering the pressure to the inside of tubular element 402 can be utilized. For example, it is envisioned that a piston or bellows assembly may be utilized, or that a chemical reaction may be employed to achieve the pressure differential.

Figure 21:
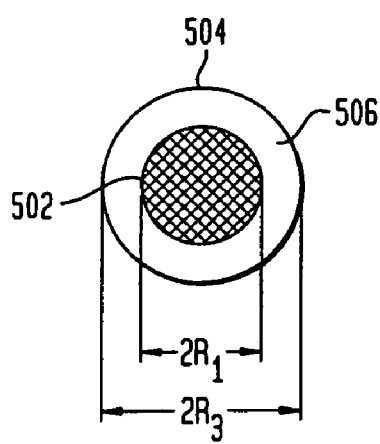
FIG. 21 is a cross sectional view of the larger end of a variable flow resistor in accordance with a fourth embodiment of the present invention with an insert centrally located.
Figure 22:
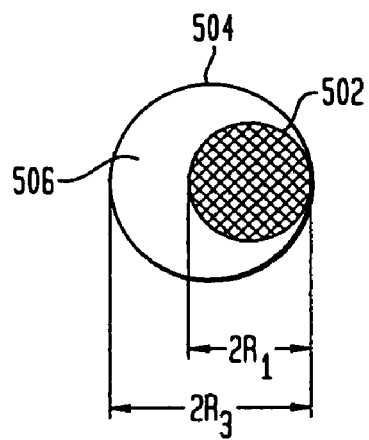
FIG. 22 is a cross sectional view of the larger end of a variable flow resistor in accordance with a fourth embodiment of the present invention with an insert eccentrically located.
Figure 23:
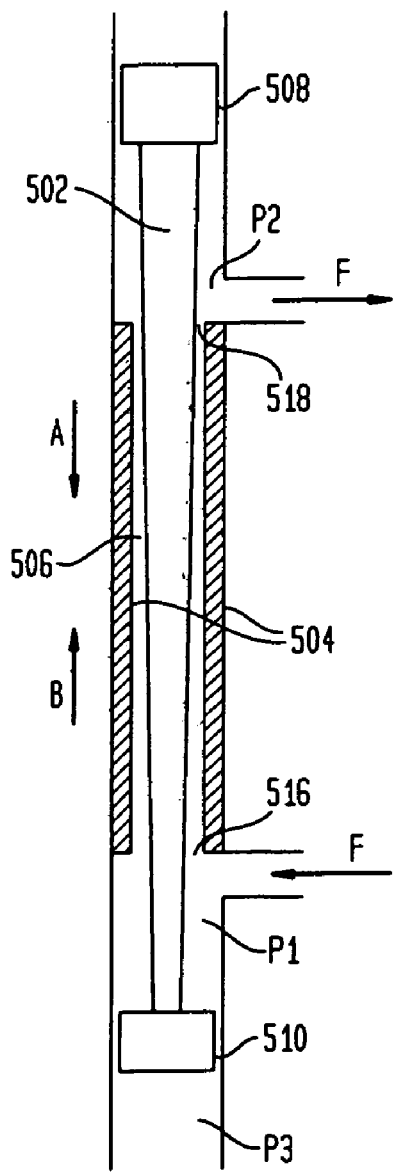
FIG. 23 is a longitudinal cross sectional view of the variable flow resistor of FIG. 21.
Figure 24:
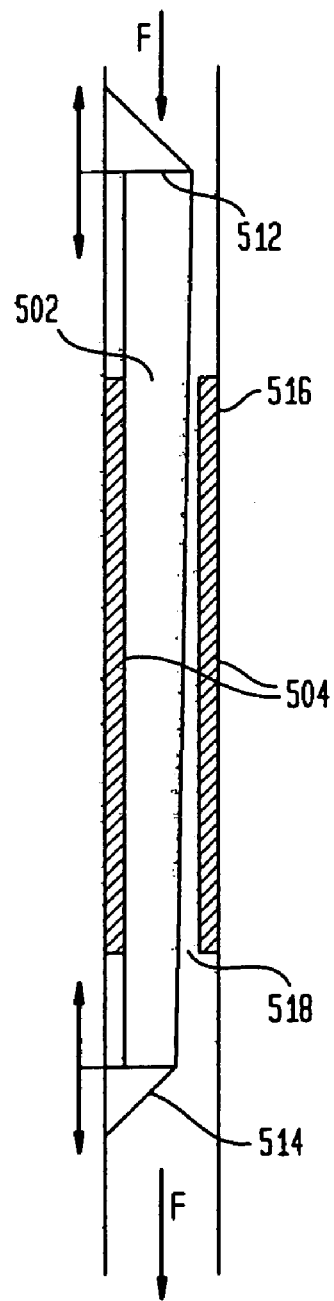
FIG. 24 is a longitudinal cross sectional view of the variable flow resistor of FIG. 22.

In a fourth embodiment the adjustment of flow rate is realized by providing an insert 502 having a longitudinally varying cross section. By moving the insert 504 along the longitudinal axis of a capillary 504, the hydraulic resistance of resistor 32 is changed. Once again, the fourth embodiment will be discussed with respect to pump 20; however, it may be utilized in combination with any implantable pump. As shown in FIGS. 21-24, in accordance with this fourth embodiment, resistor 32 includes the aforementioned insert 502 positioned within a capillary 504. In one example of this fourth embodiment, as is shown in FIGS. 21 and 23, insert 502 is depicted as having a conical shape, and is centrally located within capillary 504. Thus, the cross section of insert 502 varies across its longitudinal axis and the design forms a ring-shaped flow channel 506. This insert is fixed at its ends to two movable piston-like attachments 508, 510. However, another example is shown in FIGS. 23 and 24, in which insert 502 may be positioned eccentrically resulting in a sickle-shaped flow channel 506. In this example, insert 502 is fixed at its ends to two movable fixations 512, 514.

In operation of both examples, fluid flows in the direction indicated by arrows F, and is subjected to the flow channel from entrance 516 to exit 518 (i.e.—the aforementioned effective length). While the above-discussed equations relating to the flow rate do not necessarily apply to this embodiment, it is clear that the width of flow channel 506 may be varied by moving insert 502 in the direction of the axis of capillary 504. For example, as shown in FIG. 23, movement of insert 502 in the direction depicted by arrow A will cause a decrease in the width of flow channel 506, and thus a decrease in the flow rate of the fluid. Alternatively, movement of insert 502 in the direction depicted by arrow B will cause an increase in the width of flow channel 506, and thus an increase in the flow rate of the fluid.

It is noted that the movement of insert 502 may be achieved in different fashions depending upon the type of design utilized. For example, as shown in FIG. 23, piston-like attachments 508, 510 are preferably moved by providing a suitable pressure thereto. However, as shown in FIG. 24, movable fixations 512, 514 may also be utilized that are moved by providing a mechanical force thereto, from source such as a hydraulic, electrical or mechanical source or the like. Various means may be employed for providing movement to insert 502, including those discussed herein and others that would be well known to those skilled in the art. For example, once again, magnetic forces may be employed for moving insert 502. Finally, insert 502 may include a varying cross section that creates a substantially smooth longitudinal surface, as shown in the figures, or, insert 502 may be comprised of several non-congruent cross sectional portions. The latter configuration would provide an insert that has several different stepped sections. Thus, moving a first section into capillary 504 having a relatively large cross section would most likely reduce the flow rate, while moving a second section of lesser cross section would increase the flow rate.

Figure 25:
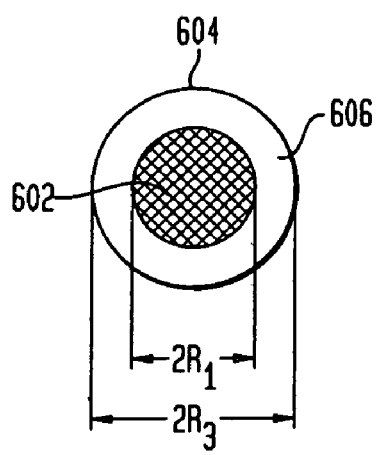
FIG. 25 is a cross sectional view of a variable flow resistor in accordance with a fifth embodiment of the present invention with an insert centrally located.
Figure 26:
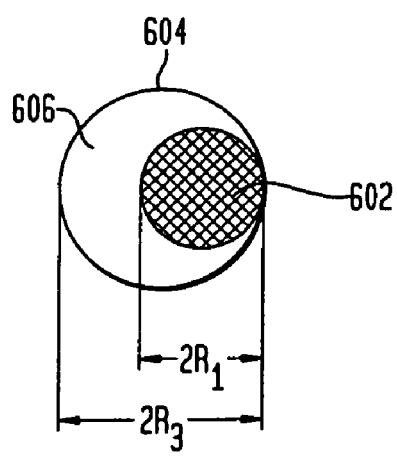
FIG. 26 is a cross sectional view of a variable flow resistor in accordance with a fifth embodiment of the present invention with an insert eccentrically located.
Figure 27:
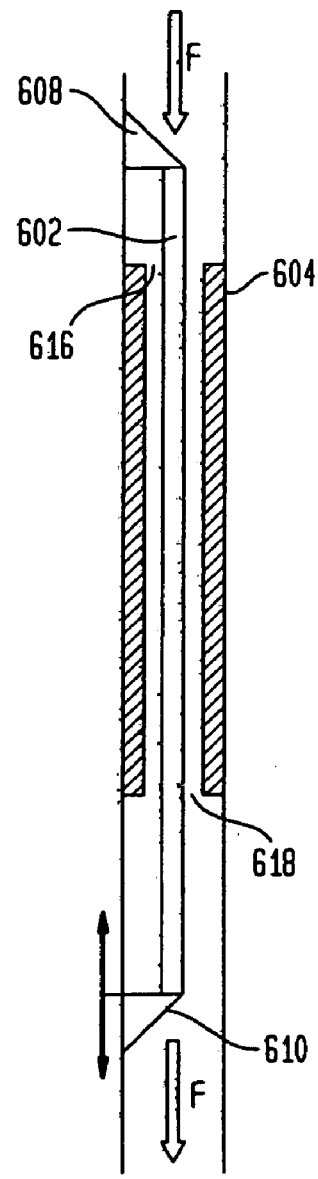
FIG. 27 is a longitudinal cross sectional view of the variable flow resistor of FIG. 25.
Figure 28:
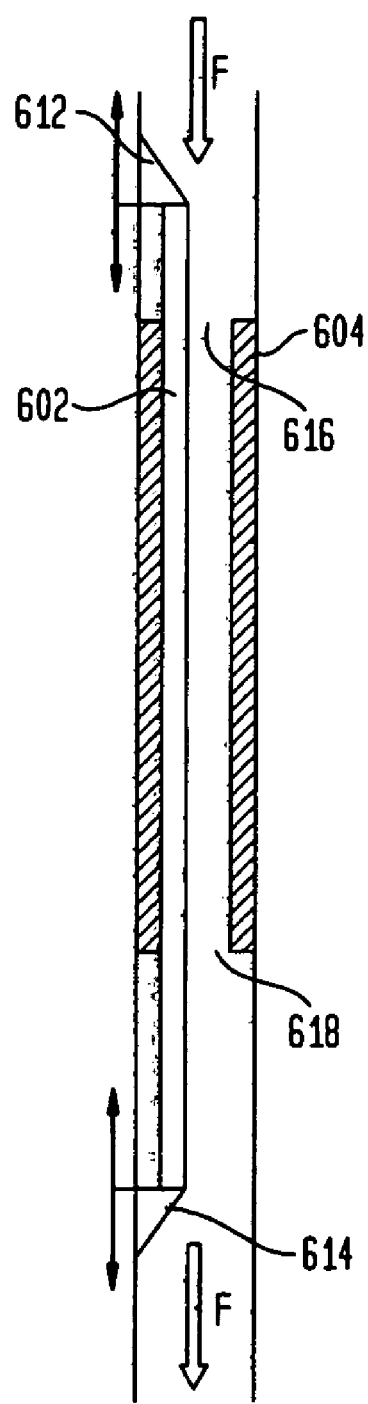
FIG. 28 is a longitudinal cross sectional view of the variable flow resistor of FIG. 25.

In a fifth embodiment the adjustment of flow rate is realized by adjusting the cross-sectional geometry of an insert being constructed of an electroactive polymer (EAP). For example, such an insert may be constructed of polyanilin, polypyrrol, or the like. This type of material is also known in the art as an artificial muscle. Essentially, the diameter of this EAP insert may be changed by applying an electric voltage thereto. In accordance with this fifth embodiment, the voltage applied to such an EAP insert may be between approximately zero (0) and two (2) volts, but may be as much as seven (7) volts. Once again, the fifth embodiment will be discussed with respect to pump 20; however, it may be utilized in combination with any implantable pump. As shown in FIGS. 25-28, in accordance with this fifth embodiment, resistor 32 includes an insert 602, which is constructed of EAP, positioned within capillary 604. FIGS. 25 and 27 show a first example where insert 602 is centrally located in capillary 604, while FIGS. 26 and 28 show a second example where insert 602 is eccentrically located in capillary 604. Further, the first example includes an insert 602 with one end fixed at a stationary attachment 608 and the other end fixed at movable attachment 610, while the second example includes an insert 602 with both ends fixed to movable fixations 612, 614.

In operation of both examples, fluid flows in the direction indicated by arrows F, and is subjected to the flow channel from entrance 616 to exit 618 (i.e.—the effective length). The width of flow channel 606 may be varied by varying the voltage between the ends of insert 602. Such application of voltage causes insert 602 to lengthen, which thereby reduces its diameter. Essentially, in accordance with this fifth embodiment, insert 602 would act as an electrode, while capillary 604 may act as a counterelectrode. As has been discussed several times above, the decrease in the diameter of an insert similar to insert 602 necessarily decreases the hydraulic resistance in capillary 604 and increases the fluid flow rate. It is noted that the calculations relating to the first embodiment above may be useful in determining the proper sized insert 602 for use in examples of this fifth embodiment that utilize an insert 602 and capillary 604 that each have circular cross sections.

The various embodiments of resistor 32, in accordance with the present invention, should be positioned such that fluid housed in the slow release chamber of an implantable pump is forced to pass through it. This configuration allows for the implantable pump to operate in its normal fashion, with resistor 32 controlling the fluid flow rate. However, preferred constructions would situate resistor 32 such that an injection into a bolus port or the like would not be forced to pass through the resistor. It is typically not required to control the flow rate of a bolus injection. Rather, such an injection is often intended to be a quick and direct application of a medication fluid. For example, as shown in FIG. 7, resistor 32 is situated so as to capture fluid flowing from chamber 24, but not fluid directly injected into bolus port 46. However, other constructions are envisioned. Furthermore, where the implantable pump is utilized to withdraw spinal fluid, it is also contemplated to not force such fluid through resistor 32. In the pump of FIG. 7, withdrawal of spinal fluid would occur through bolus port 46. As such, the fluid would not be required to pass through the resistor.

For each of the embodiments above, providing a controlling mechanism for selectively varying the flow rate of the medication fluid is envisioned. Many different such mechanisms are well known and widely utilized with implantable devices for implantation into a patient's body. For example, prior art devices have shown that it is possible to utilize dedicated hard wired controllers, infrared controllers, or the like, which controllers could be used in accordance with the present invention to control various elements, such as motor 282, to selectively vary the flow rate of the medication fluid. U.S. Pat. No. 6,589,205 ("the '205 patent"), the disclosure of which is hereby incorporated by reference herein, teaches the use of a wireless external control. As discussed in the '205 patent, such a wireless control signal may be provided through modulation of an RF power signal that is inductively linked with the pump. The '205 cites and incorporates by reference U.S. Pat. No. 5,876,425, the disclosure of which is also hereby incorporated by reference herein, to teach one such use of forward telemetry or the exchange of information and programming instructions that can be used with the present invention to control the pump and the various aforementioned elements that are varied in order to affect the flow rate. However, it is noted that similar external controllers may also be utilized. Such controllers can send control signals wirelessly (such as by IR, RF or other frequencies) or can be wired to leads that are near or on the surface of the patient's skin for sending control signals. Furthermore, a pump in accordance with the present invention may include safeguards to prevent the inadvertent signaling or improper programming of the pump. For example, the present invention could utilize a secure preamble code or encrypted signals that will be checked by software or hardware used for controlling the pump or even dedicated only for security purposes. This preamble code would prevent the inadvertent varying of the flow rate of the fluid from the pump, from being caused by outside unrelated remote control devices or signals and by other similar pump controllers. Other safety precautions may be used, such as passwords, hardware or software keys, encryption, multiple confirmation requests or sequences, etc. by the software or hardware used in the programming of the pump.

The electronics and control logic that can be used with the present invention for control of the motors and controllably displaceable elements used to vary the flow rate may include microprocessors, microcontrollers, integrated circuits, transducers, etc. that may be located internally with or in the implantable pump and/or externally with any external programmer device to transmit pump programming information to control the pump. For example, any external programmer device used to allowing programming of the pump. The electronics can also be used to perform various tests, checks of status, and even store information about the operation of the pump or other physiological information sensed by various transducers.

An external programmer device may also be avoided by incorporating the necessary logic and electronics in or near or in the implantable pump such that control can be accomplished, for example, via control buttons or switches or the like that can be disposed on or below the surface of the skin. Of course, necessary precautions (such as confirmation button pressing routines) would need to be taken so that inadvertent changing of programming is again avoided.

A specific implantable pump 700, which incorporates the above discussed reduced size designs, as well as the above discussed infinitely variable designs of the present invention will now be described. Essentially, pump 700 is an implantable pump having certain novel characteristics. These characteristics allow for both the relative miniaturization and easy construction of the pump. In addition, pump 700 incorporates one of the aforementioned resistor 32 designs into the specific embodiment. While pump 700 is indeed one preferred embodiment for use in accordance with the present invention, it should be clearly understood that the pump could be modified to incorporate each of the resistor 32 designs discussed above in many different configurations.

Figure 29:
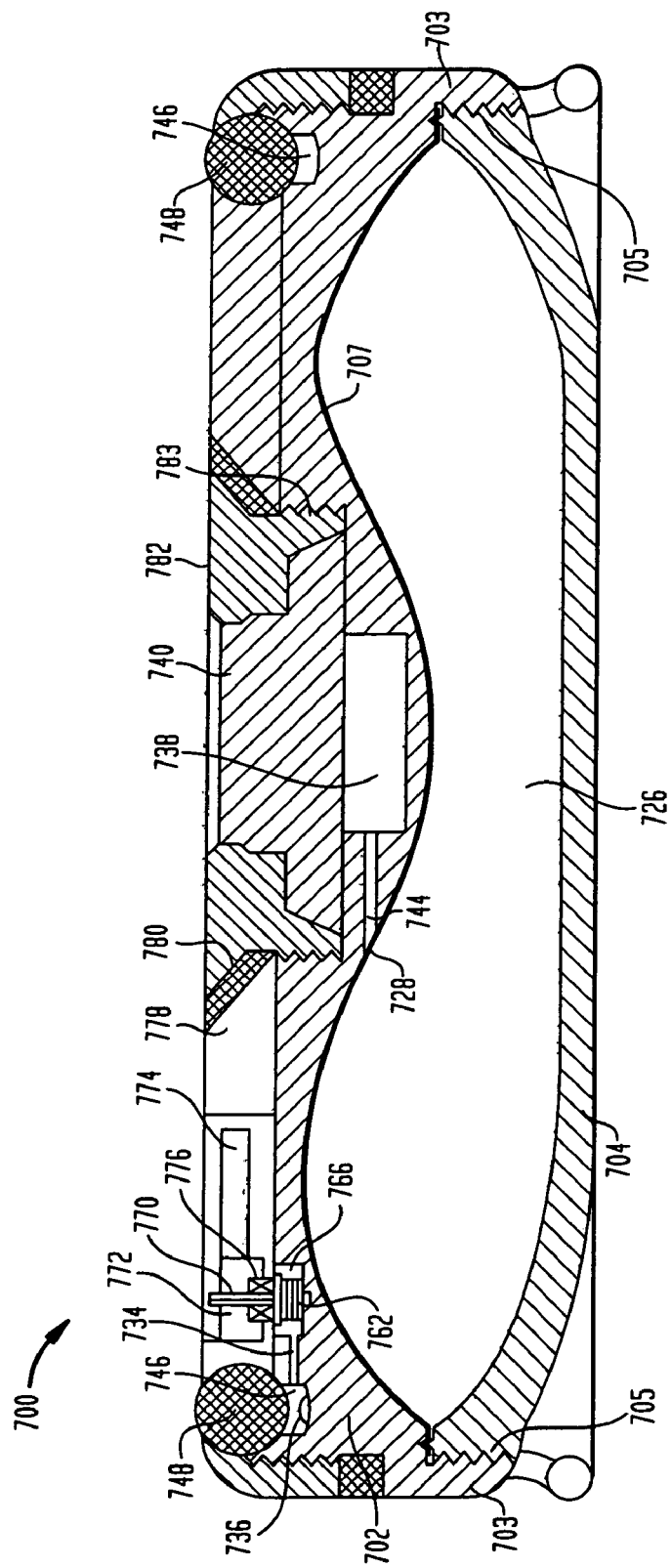
FIG. 29 is a cross sectional view of an implantable pump in accordance with another embodiment of the present invention.
Figure 30:
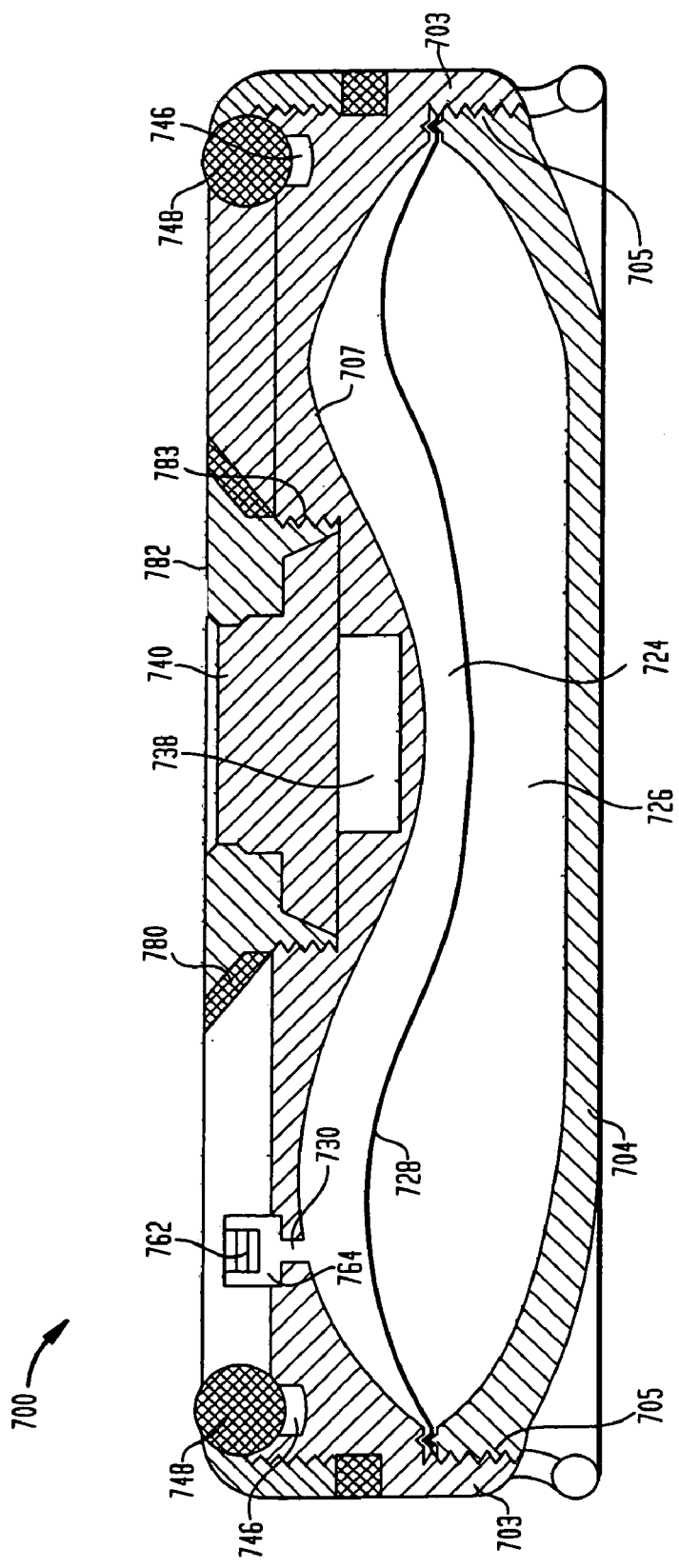
FIG. 30 is a cross sectional view of the implantable pump shown in FIG. 29, taken along a different portion thereof.

As shown in FIGS. 29 and 30, pump 700 includes a housing constructed of an upper portion 702 and a lower portion 704. The housing portions are preferably constructed of a strong polymeric material, such as polyetherehterketone, sold under the designation PEEK by Invibio of the United Kingdom. Other suitable biocompatible materials may also be employed. Nevertheless, the particular material should be chosen so as to be capable of forming a two part housing that can be safely assembled without the use of a complicated double clinch assembly, a welding process or the like. Clearly, safety is a very big concern in the construction of any apparatus inserted into the body especially one housing an overdose of medication solution. Heretofore, implantable pump housings have either been constructed of a metallic material, wherein a welding process is utilized for attaching the portions of the housing together, or a polymeric material, wherein a complicated clinching assembly is utilized for attaching the portions of the housing together. For example, a metallic pump is typically constructed by welding together two metallic halves of the pump housing. Similarly, as taught in commonly owned U.S. Pat. Nos. 5,814,019 and 5,836,915, a double clinching assembly has been previously proposed for safely attaching the housing halves of a polymeric pump.

In accordance with the present invention, it has been discovered that utilizing a material such as PEEK may allow for a polymeric pump housing to be constructed without the use of any of the complicated attachment procedures. The elimination of such extraneous elements allows for pump 700 to be smaller in size. For example, the elimination of the aforementioned double clinch safety feature allows for the overall width of pump 700 to be reduced. Further, in certain embodiments, this may also decrease the overall weight of the pump, as well as the level of complicity required in assembling same. As shown in FIG. 29, portions 702 and 704 of the housing of pump 700 are constructed of PEEK and designed so as to be capable of simply screwing together. More particularly, portion 702 includes an interiorly threaded extension 703 for receiving an exteriorly threaded surface 705 of portion 704. In certain embodiments, in addition to the threaded connection, a layer of glue or other adhesive may be applied to the connection between portions 702 and 704. Such an application may provide further assurance that the two portions do not inadvertently become detached. It is also contemplated that other less complicated attachment modes may be employed. For example, in addition to the threadable connection between portions 702 and 704, a single clinch connection may be utilized. In this type of attachment, the two portions may include elements that are designed so as to snap fit together, and thereafter fixably secure the portions together.

As with the aforementioned generic pump 20 design, implantable pump 700 further includes an interior having two chambers 724 and 726, each chamber being separated by a flexible membrane 728. Chamber 724 is designed to receive and house an active substance such as a medication fluid, while chamber 726 is designed to house a propellant that expands isobarically under constant body temperature. Similar to above discussed generic pump 20, the expansion of the propellant in pump 700 displaces membrane 728 such that the medication fluid housed in chamber 724 is dispensed into the body of the patient through the path defined by an outlet opening 730 (FIG. 30), a cylindrical recess 764, a resistor 732 (FIG. 31), a cylindrical recess 766 (FIG. 29), an outlet duct 734 and ultimately an outlet catheter 736. Also in accordance with pump 20, pump 700 further includes a replenishment port 738 covered by a first septum 740, and an annular ring bolus port 746 covered by a second ring shaped septum 748. The utility of each of these ports is substantially identical to those of pump 20. For example, a passage 744 allows fluid injected into replenishment port 738 to be introduced into chamber 724. In addition, like that of pump 20, it is envisioned that specifically designed injection needles and correspondingly situated septa may be employed to increase safety, as discussed above.

Contrary to the aforementioned pump 20, pump 700 includes an undulating membrane 728 which cooperates with a similarly undulating interior surface 707 of portion 702. As best shown in FIGS. 29 and 30, interior surface 707 of portion 702 has an undulating surface that serves as the top surface of chamber 724, while membrane 724 has a corresponding undulating surface that serves as the bottom surface of chamber 724. When chamber 724 is empty, membrane 724 fits flush against the similarly shaped interior surface 707. This is best shown in FIG. 29. However, upon introduction of a fluid into chamber 724, membrane 728 is capable of flexing and allowing for the expansion of chamber 724. This is best shown in FIG. 30. This undulating configuration of membrane 728 and interior surface 707 of portion 702 allows for replenishment port 738 and septum 740 to be situated at a lower position with respect to the height of the pump. Essentially, a center portion of both interior surface 707 and membrane 728 are a convex shape allowing for portion 738 and septum 740 to be set lower. At the same time, portions to the left and right of this center portion are enlarged, taking substantially concave shapes. This allows for the overall volume of chamber 724 to remain substantially similar in comparison to well-known implantable pumps. Operation of pump 700 also remains substantially similar to prior art implantable pumps being driven by a propellant. While the specific undulating design (i.e.—a convex or lower portion flanked by two concave or higher portions), shown in FIGS. 29 and 30, is one suitable embodiment, other embodiments are envisioned. For example, other pumps may include surfaces and membranes that have corresponding shapes having multiple concave and/or convex portions.

Figure 31:
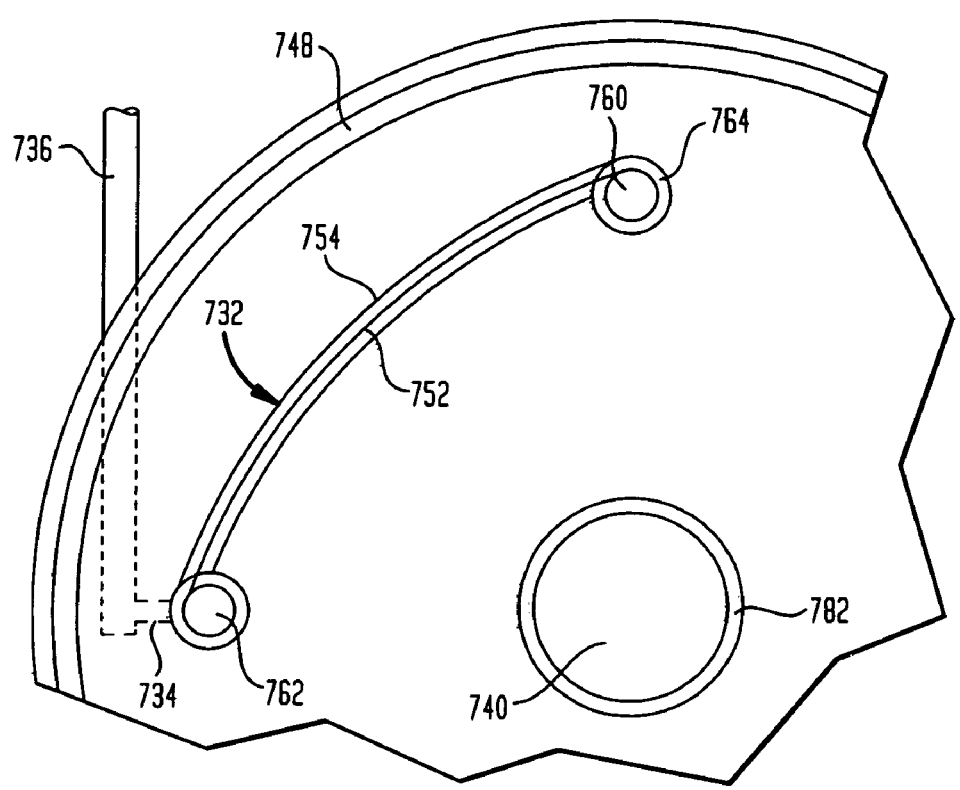
FIG. 31 is a partial top view of the implantable pump shown in FIG. 29.

The specific construction and cooperation of resistor 732 within pump 700 is shown in detail in FIGS. 29-31. The resistor shown in this specific embodiment is akin to the above described first embodiment resistor. As best shown in FIG. 31, resistor 732 includes an elastic and resilient filament 752 situated in a capillary 754. Filament 752 extends through capillary 754 and is attached on its ends to two spools 760 and 762. Spool 760 resides within cylindrical recess 764 in fluid communication with opening 730 in portion 702, while spool 762 resides within a cylindrical recess 766 in portion 702. Recess 764 is in fluid communication with outlet opening 730 and hence chamber 724 (best shown in FIG. 30). Similarly, recess 766 is in fluid communication with outlet duct 734, and hence outlet catheter 736 (best shown in FIG. 29). Thus, fluid will flow from chamber 724 through resistor 732, and out of catheter 736 to a target site within the body.

As best shown in FIG. 31, capillary 754 is preferably curved so as to force filament 752 to one side thereof. Spools 760 and 762 are adapted to wind filament 752 thereon and thus vary its cross section. As more specifically discussed above, this varying in cross section varies the flow rate of fluid through capillary 754. In the embodiment shown in FIGS. 29-31, spool 760 is adapted to remain in a fixed position, while spool 762 is adapted to be rotated. However, in other embodiments, both spools may be adapted to be rotated. As best shown in the cross sectional view of FIG. 29, spool 762 is mechanically coupled to several actuation components including being coupled via an axle 770 to a wheel 772. A motor 774, like that of the above mentioned X15G, is employed to provide rotation to wheel 772. A bearing 776 or the like may aid in the rotation of axle 770, by guiding and providing smooth motion to axle 770. In the embodiment shown in the figure, motor 774 receives electrical energy and control from an electronic unit 778, which, as discussed above, is controlled from either internally or externally of the body.

The aforementioned actuation components are held together and within pump 700 through a specific cooperation that is best shown in FIG. 29. Essentially, ring septum 748 and an elastic element 780 are designed to hold the actuation components to pump 700. The actuation elements are preferably housed so as to be a single module encompassing spool 762, axle 770, wheel 772, motor 774, bearing 776 and electronic unit 778. During assembly, this module is placed into a recess on pump 700 so that one side abuts ring septum 748. With the module in place, septum 740 is attached to portion 702 by screwing a holder 782, which holds septum 740, to portion 702 of pump 700, so as to form a threaded connection 783. Holder 782 is preferably constructed of PEEK material like portions 702 and 704. It is also contemplated that other modes of attachment may be employed, such as, by adhesive or a combination of adhesive and threads. Ring 780 of elastomeric material is preferably placed between holder 782 and electronic unit 778, and the cooperation thereof holds the aforementioned module between septum 748 and ring 780. Essentially, one side of the module is designed to cooperate with septum 748 (i.e.—curved cooperation), while the other side is designed to cooperate with ring 780 (i.e.—sloped cooperation). Thus, in the fully constructed state, the module of actuation components is essentially frictionally attached to pump 700.

The specific embodiment shown in FIGS. 29-31 also allows for an easy conversion from a variable flow rate pump to a fixed flow rate pump. In use, the manufacturer or user of the pump would simply remove the aforementioned module of actuation components. A spacer, insert or the like may inserted into any cavity formed in the housing of pump 700, after the removal of the module. Filament 752 is also removed from capillary 754 and replaced with a small tube (not shown), constructed of a material such as glass. The tube preferably has an outer diameter slightly smaller than the inside diameter of capillary 754, so as to allow a snug fit therein. Further, the tube may have any suitable inner diameter, it being noted that the particular inner diameter size dictates the flow rate of fluid through capillary 754. Thus, depending upon the desired fixed flow rate, a particular tube having a suitable inner diameter should be selected. Finally, the tube should be capable of conforming to the preferable curved shape of capillary 754. With these simple modifications to pump 700, a relatively inexpensive fixed flow rate pump may be produced. This simple conversion allows for the use of the majority of the components of pump 700 without requiring the modification of any. This is beneficial, because new molds or the like would not be needed to change between pump designs.

Figure 32:
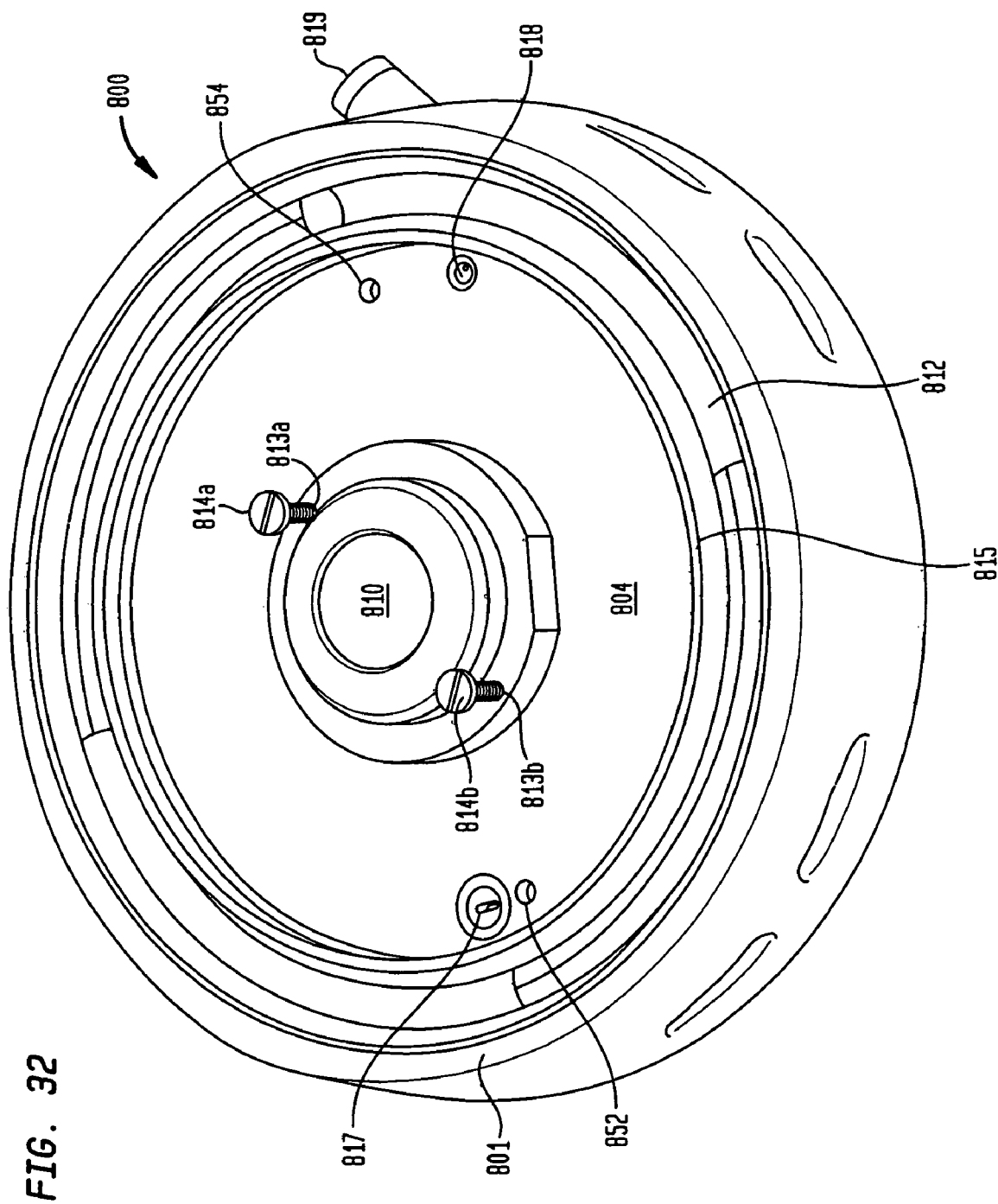
FIG. 32 is a top perspective view of another embodiment implantable pump of the present invention.
Figure 33:
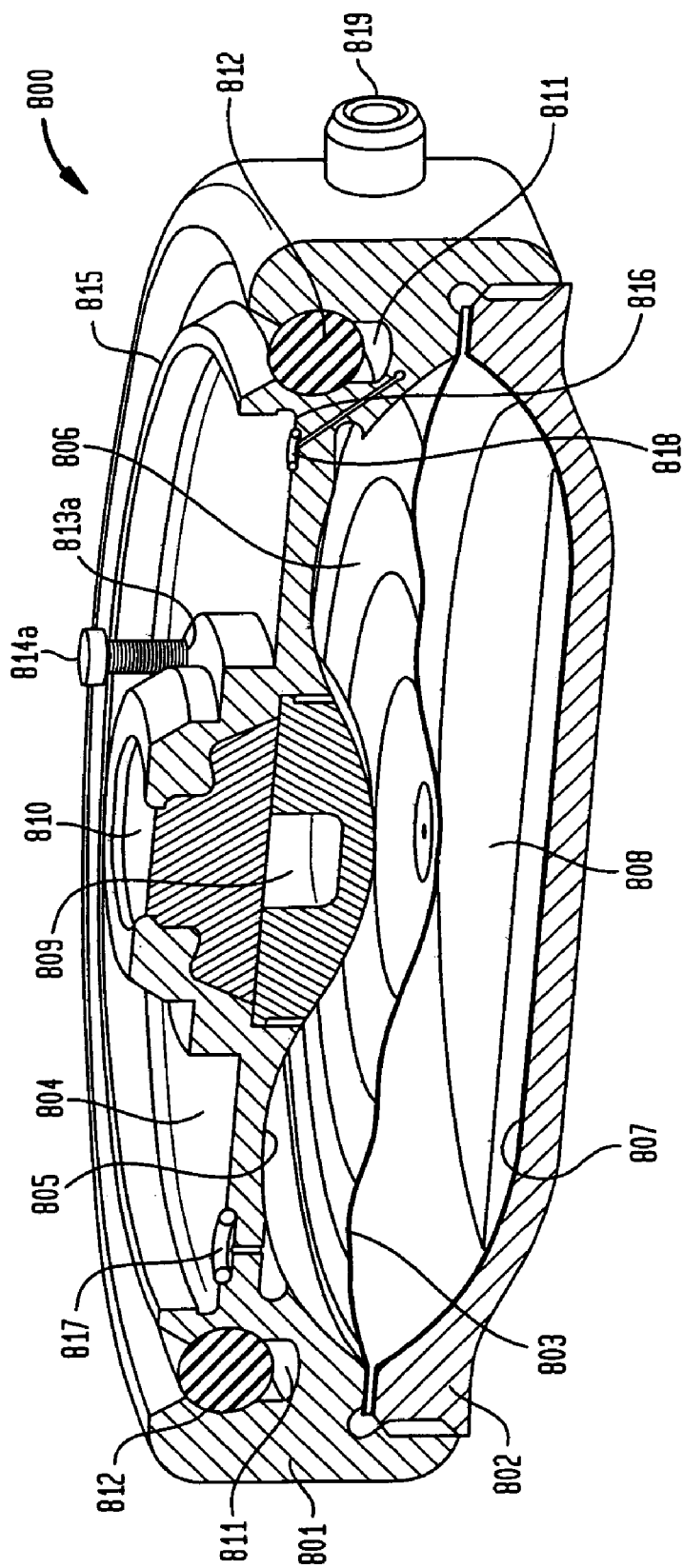
FIG. 33 is a cross sectional view of the pump depicted in FIG. 32.
Figure 34:
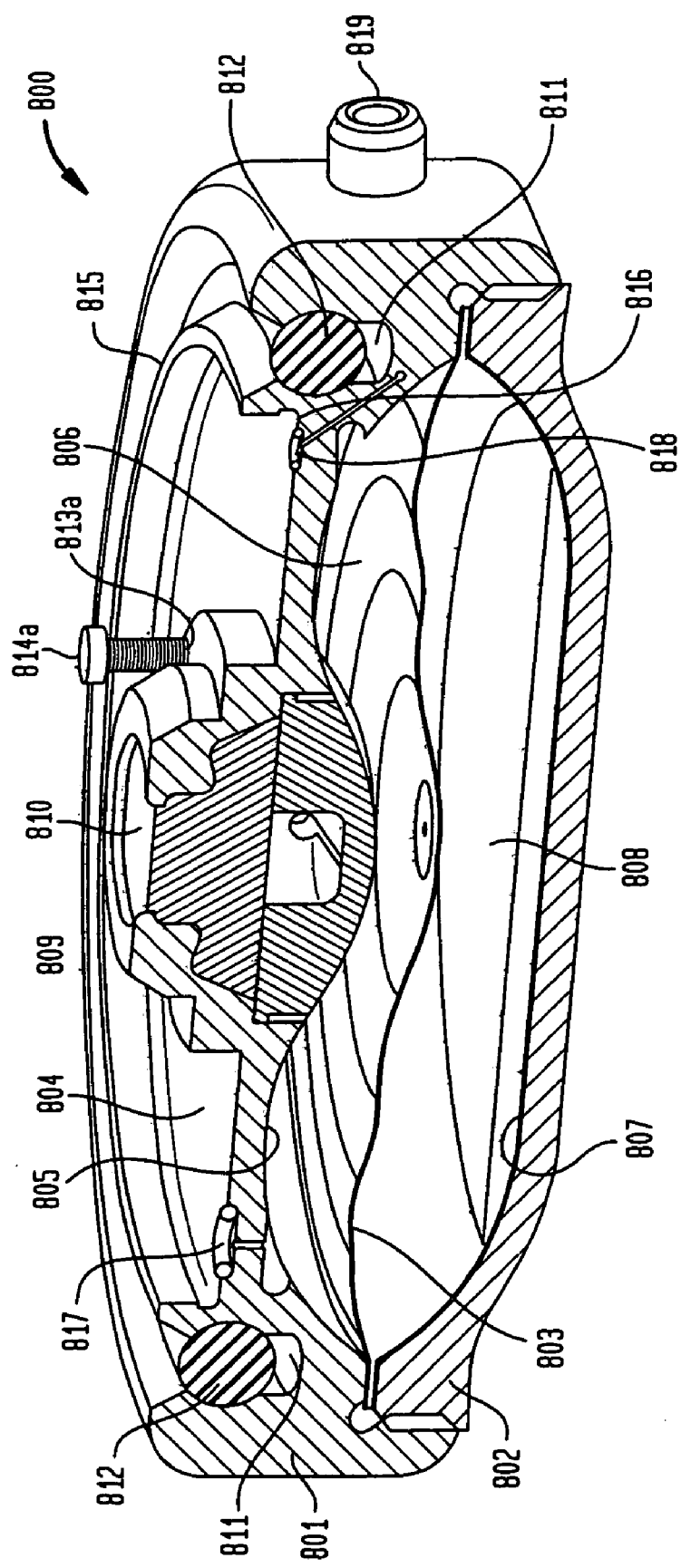
FIG. 34 is another cross sectional view of the pump depicted in FIG. 32.

A further preferred embodiment implantable pump is depicted in FIGS. 32-34, and is designated with reference numeral 800. Pump 800 is similar in nature to the above-described implantable pumps, and is designed to employ a resistor or restrictor module that operates to vary the flow rate of medicament from the pump. The restrictor modules for use with pump 800 will be discussed more fully below. Pump 800, in and of itself, operates in similar fashion to the previously described pump 700, although it does utilize some different structure and certain additional and/or different components. Because of several differences and/or addition of elements between pump 700 and pump 800, similar components and/or structure of pump 800 are not labeled with like reference numerals to that of pump 700.

As is shown in FIGS. 32-34, pump 800 includes an upper portion 801 forming an upper portion of a housing and a lower portion 802 which is preferably designed to screw into portion 801, thereby capturing a membrane 803 therebetween, in a similar fashion to other embodiments discussed above. However, in pump 800, a second membrane 803a (best shown in FIG. 41), is provided and preferably forms a pocket or balloon with membrane 803. In other words, membrane 803 forms and upper barrier of the pocket, while membrane 803a forms a lower barrier that essentially conforms to lower portion 802. Upper portion 801 includes an upper surface 804 for receiving a restrictor module and a lower surface 805 that defines an upper part of an upper or medicament chamber 806 (best shown in the cross sectional views of FIGS. 33 and 34). Lower portion 802 includes an upper surface 807 that defines a lower part of a lower or propellant chamber 808 (or allows the pocket formed by membrane 803 to remain adjacent thereto). In addition, pump 800 also includes certain of the other elements included in, for example, the above-discussed pump 700, such as, a replenishment port 809 covered by a first septum 810 and ring bolus port 811 covered by a second ring septum 812. Upper surface 804 of upper portion 801 further includes two apertures 813a and 813b for receiving screws 814a and 814b respectively, an upstanding circular ring extension 815 that forms a shoulder 816, an exit opening 817 from medicament chamber 806, and an entrance opening 818 for medicament to enter back into pump 800 and ultimately dispensed to an outlet duct 819 for ultimate travel to the patient in a manner to be discussed below.

It is noted that pump 800 utilizes a similar chamber and/or membrane design as that of pump 700, and the other reduced size implantable pumps discussed above, with a modified variable flow rate assembly that will be discussed below. The chamber and/or membrane design of pump 800 may not only be similar in design and functionality to that of the other embodiments pumps discussed herein, but may also include any of the variants of the chamber and/or membrane designs contemplated with regard to the other implantable pump designs discussed herein.

Pump 800 is preferably designed so as to operate in conjunction with one or more restrictor modules to form an implantable infusion pump system. FIGS. 35-45 depict pump 800 in conjunction with a first restrictor module 820. Restrictor module 820 is preferably removably coupled to upper portion 801 (with screws 814a and 814b) and includes several elements utilized to vary the flow rate of an active substance dispensed from pump 800. More particularly, restrictor module 820 is a stand alone component having several elements encased or encapsulated in a solid material, such as a polymeric material like the above-discussed PEEK material. In this regard, it is noted that each of upper portion 801, lower portion 802 and module 820 may be constructed of like materials, or certain of those components may be different materials. The module is preferably designed with a central aperture which allows access of septum 810 and with an overall diameter that allows is to sit within the confines of the area defined by septum 812. Module 820 preferably monitors and varies the flow rate of a medicament or active substance dispelled from pump 800 in order to provide a patient with a particular prescribed flow rate of same. For example, module 820 may vary the flow rate of the medicament in response to a signal received from an outside source (e.g., handheld device), or in response to a condition placed upon the patient (e.g., change in pressure or temperature).

Figure 35:
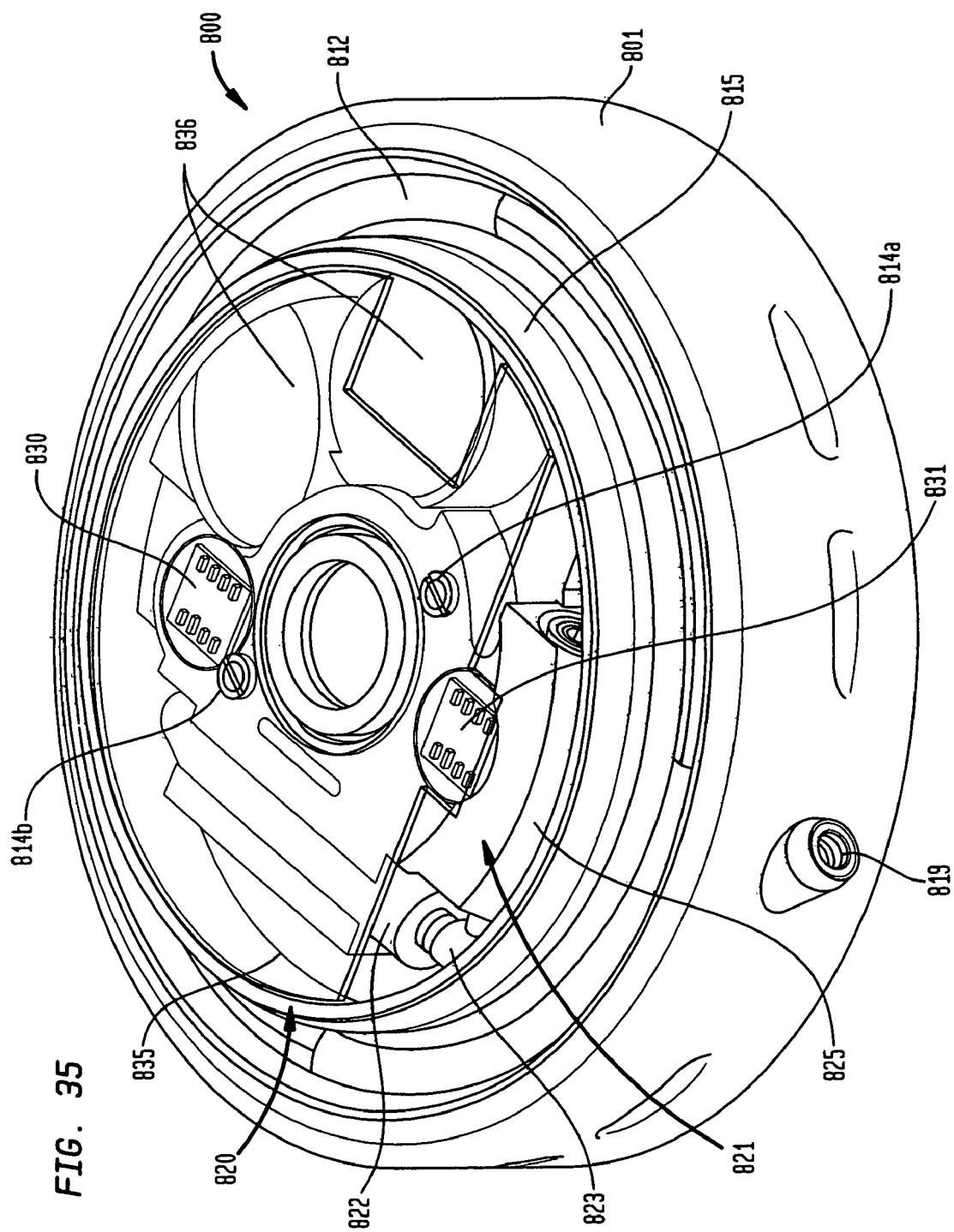
FIG. 35 is top perspective view of the pump depicted in FIG. 32, with a first embodiment variable flow module attached thereto.
Figure 36:
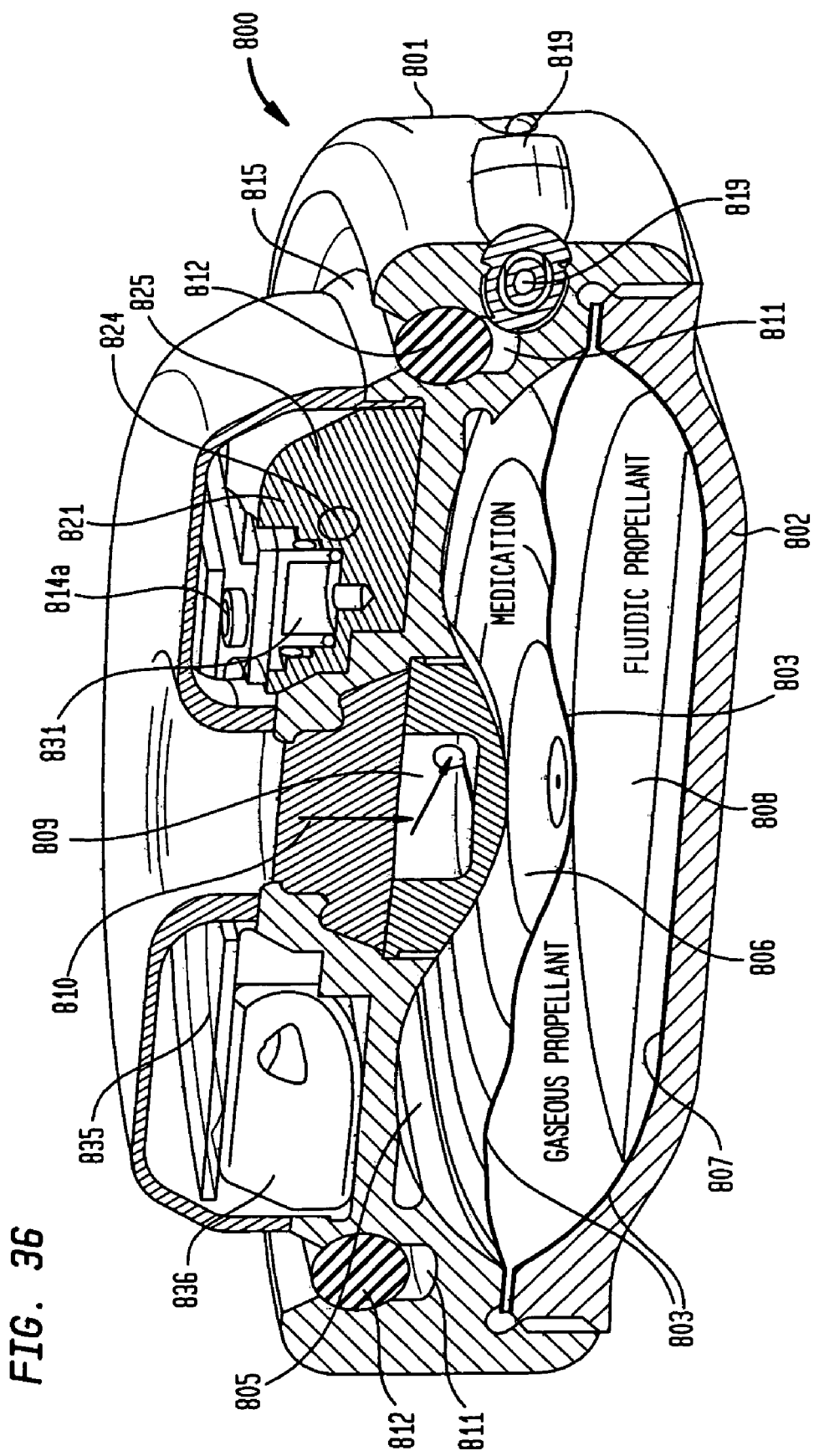
FIG. 36 is a cross sectional view of the pump and module depicted in FIG. 35.
Figure 37:
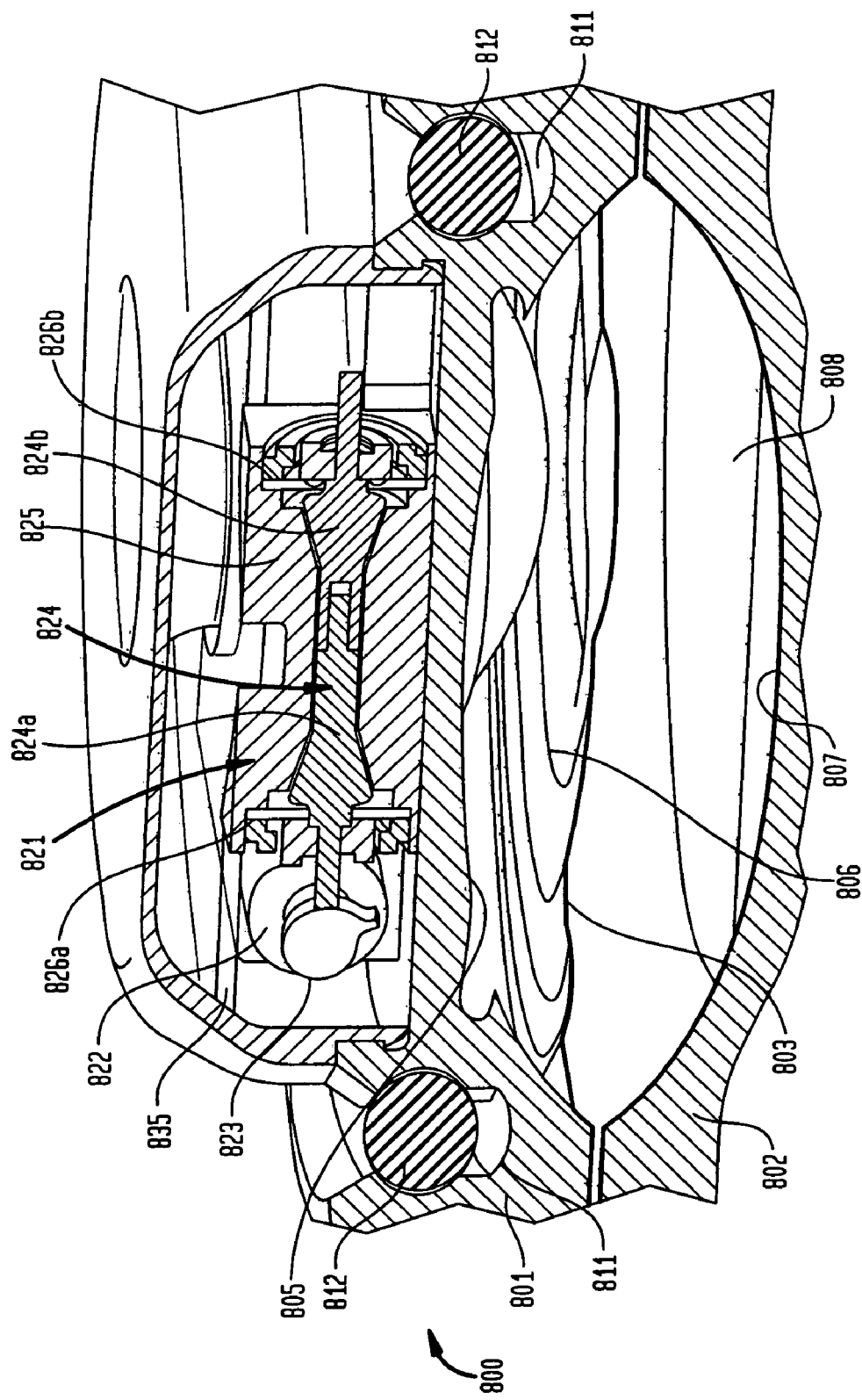
FIG. 37 is another cross sectional view of the pump and module depicted in FIG. 35.

FIG. 35 shows pump 800 with a fully constructed restrictor module 820 being mounted on surface 804 of upper portion 801, while FIGS. 36-38 show different partial cutaways of pump 800 so that certain portions of the pump itself and module 820 are hidden or removed in order to depict the various elements of pump 800 and those which are housed by module 820.

Figure 38A:
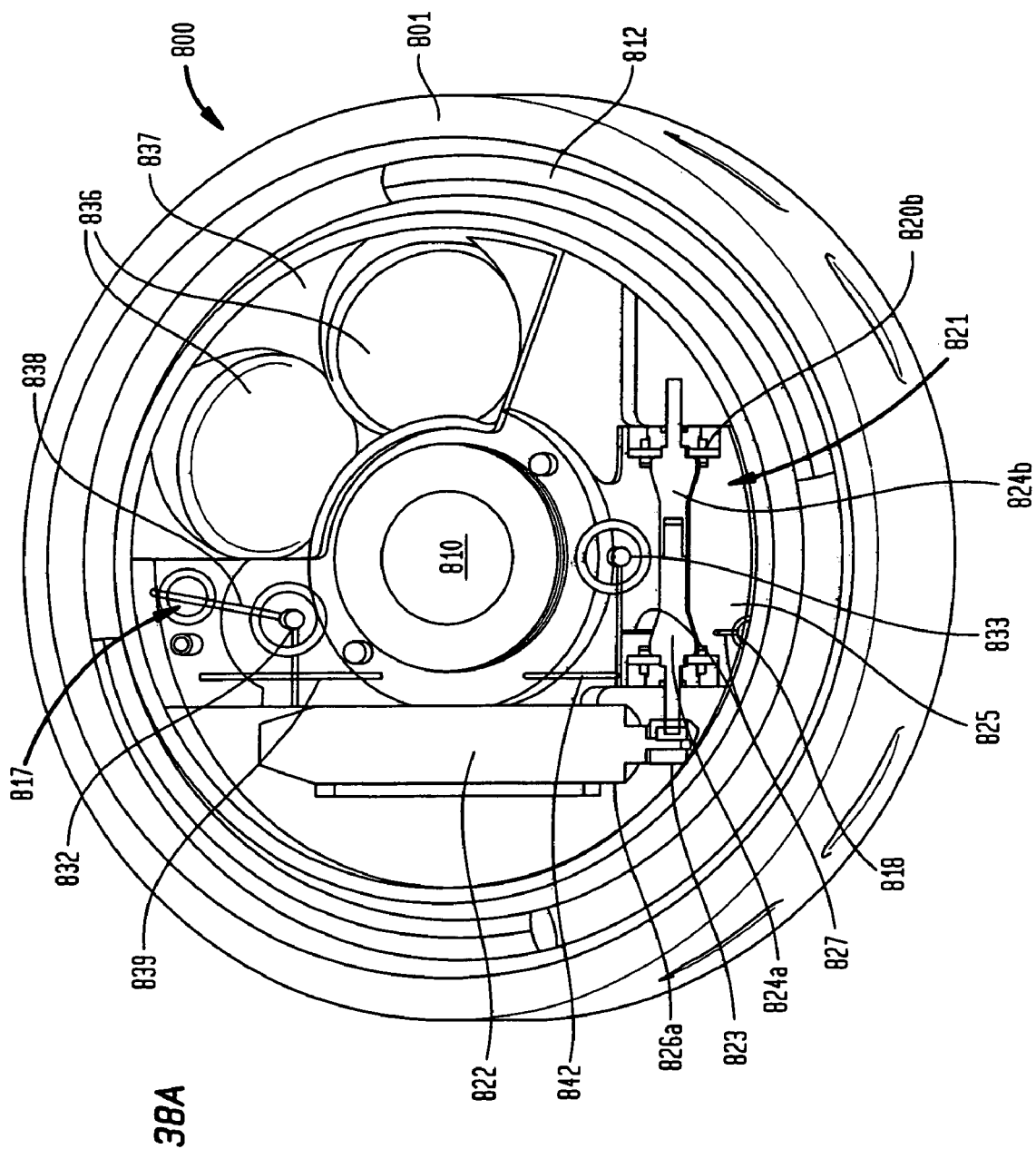
FIG. 38A is a top cross sectional view of the pump and module depicted in FIG. 35.

As is best shown in the top cut away view of FIG. 38A, module 820 includes a valve 821, a motor 822, and an offset cam or extension 823 for imparting movement to valve 821. It is noted that motor 822 can be any suitable motor capable of inclusion within module 820. Thus, such motor must fit within the constraints formed by the overall small size and particular configuration of pump 800 and module 820. One suitable motor 822 includes a gearbox ratio of 64:1 and is sold under the part number ADM 0620-2R-V6-05 by Dr. Fritz Faulhaber GmbH & CO KG of Schoneich, Germany. Cam 823 is designed as an offset cam, such that one rotation of the cam by motor 822 may cause translation of valve 821. Many different configurations may be utilized, as those of ordinary skill in the art would readily recognize. Whatever particular design for each of the elements is utilized, each of these elements preferably cooperates so that operation of motor 822 causes movement of cam 823 in order to actuate valve 821, which in turn causes variations in the flow rate of an active substance from pump 800 to a patient. The preferred cam shown is simply oblong in shape, such that a rotation of same subjects valve 821 to contact with thinner to thicker sections of the cam, which causes the needed translation.

Figure 38B:
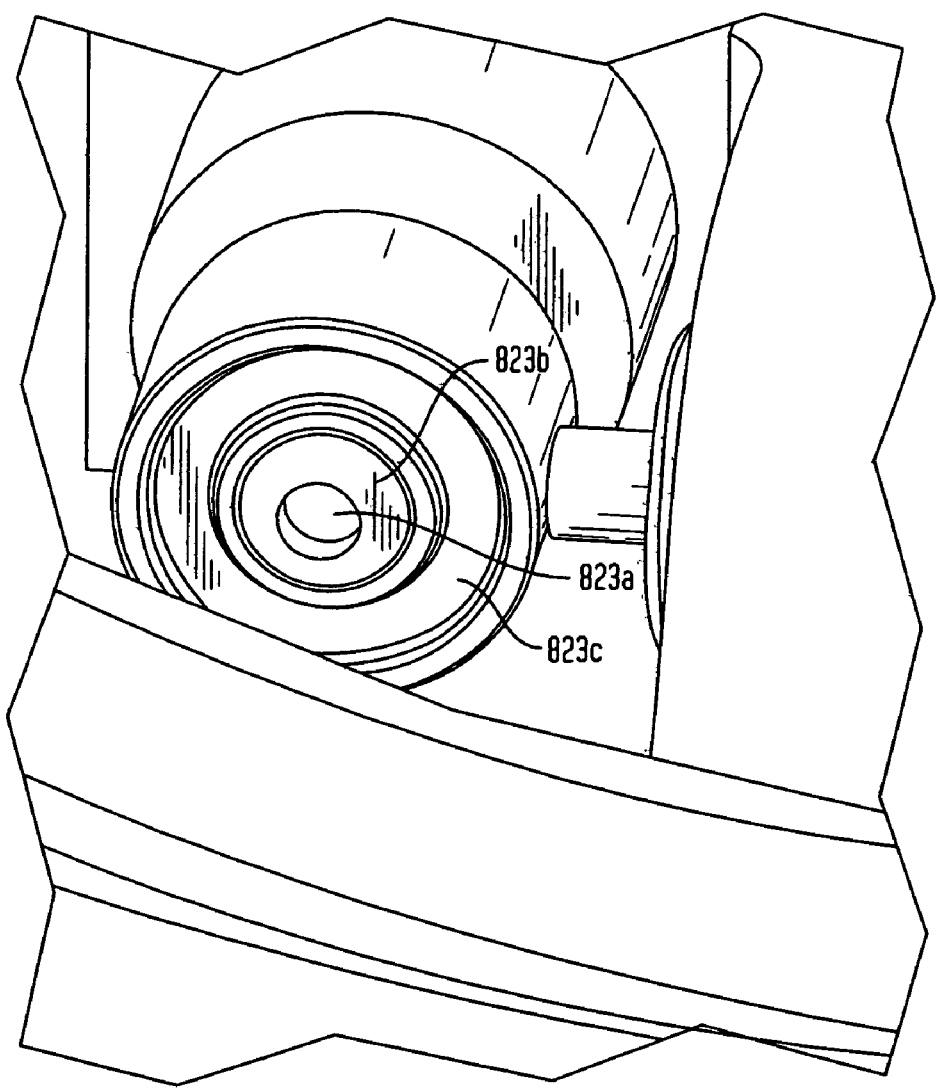
FIG. 38B is an enlarged top view of a differently configured offset cam or extension for imparting movement to a valve.

One example of a variation in the elements utilized in module 820 is shown in FIG. 38B. Specifically, that figure depicts an alternative construction for cam 823, which includes an axle 823a connected to motor 822. Axle 823a drives an eccentric cam body 823b, which in turn rotates a bearing 823c. As with most bearings, bearing 823c includes an interior rotating portion, and an exterior portion which generally does not rotate. Certain portions of valve 821 are abutted against the exterior portion of bearing 823c, and these portions are caused to actuate in a similar fashion as will be fully discussed below. In short, the rotation of axle 823a by motor 822 causes the rotation of eccentric cam body 823b and the interior portion of bearing 823c. Because of the eccentric nature of cam body 823b, bearing 823c is caused to translate upon the rotation of the eccentric body. It is noted that this particular construction may allow for translation of valve 821 without a rotating portion contacting any portion of the valve. Rather, the exterior portion of bearing 823c simply translates and contacts valve 821, without rotation.

Figure 39A:
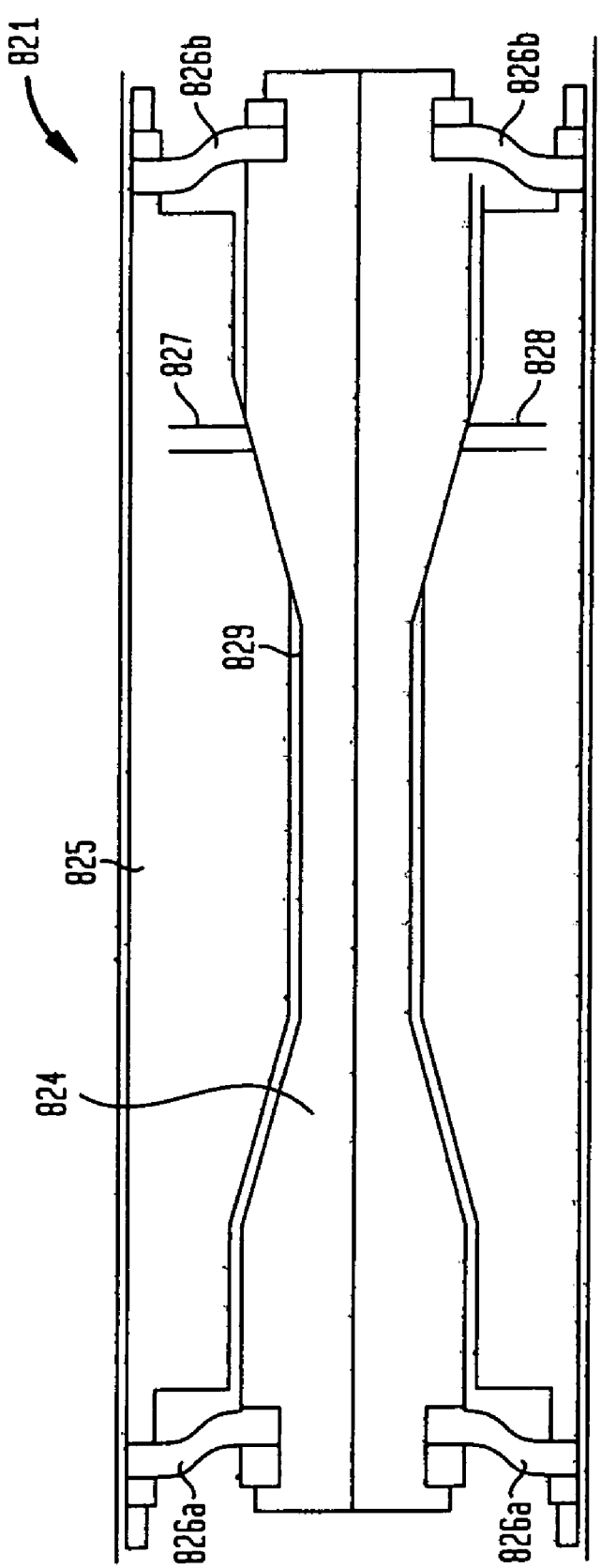
FIGS. 39a and 39b are cross sectional views of a valve utilized in the module of FIG. 35.
Figure 39B:
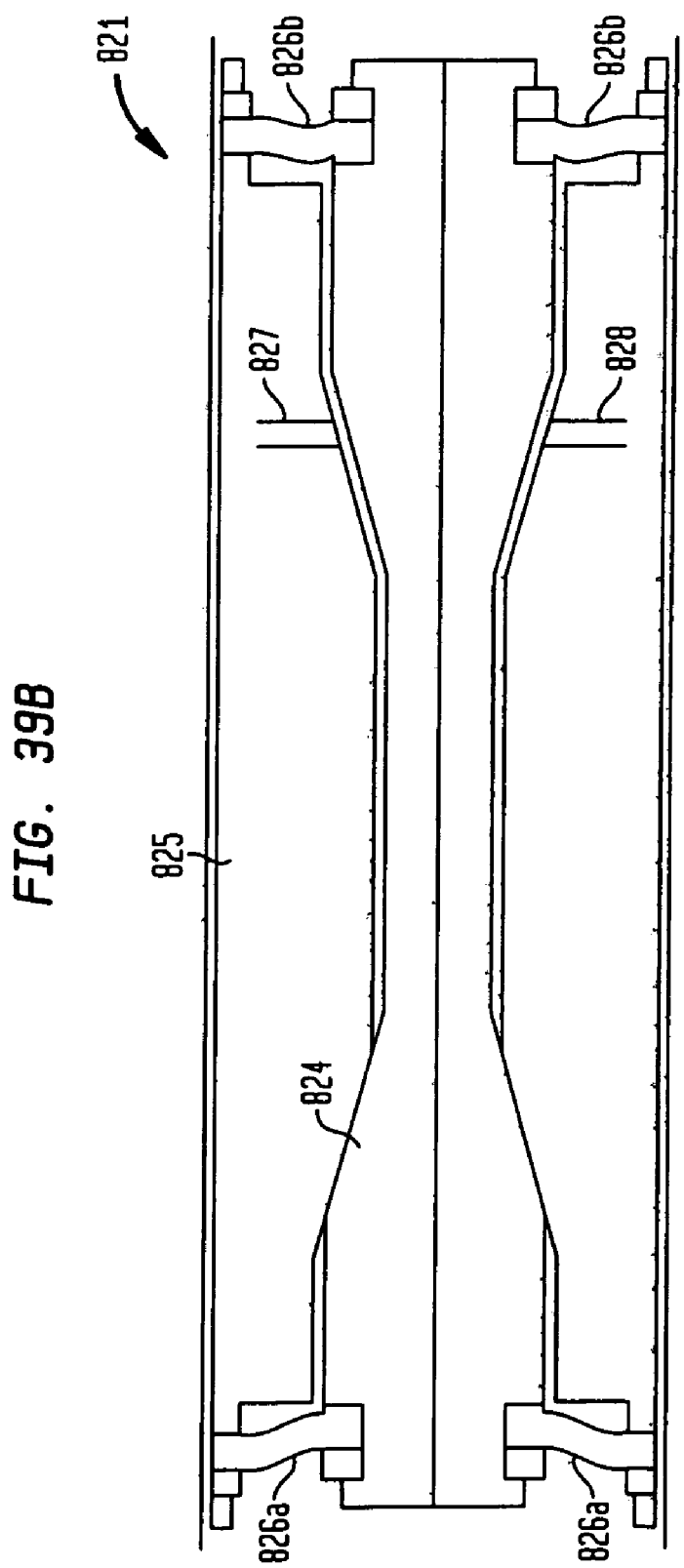

As is shown in FIGS. 37-39B, valve 821 includes a double sided needle portion 824 disposed within a valve body 825 as the mechanism allowing for the varying flow rate of an active substance being dispensed from pump 800. FIG. 37 shows portion 824 as consisting of two pieces 824a and 824b. In certain embodiments, one of the pieces (for example, piece 824b) may include a coating of a flexible material, such as rubber or silicon. This coating may allow for cooperation within valve body 825 (for example, during blockage of passages) without requiring very precise tolerances to be met. In other words, such flexible material may conform to the interior of valve body 825. Although the multi-piece format is preferred for assembly purposes, a portion 824 consisting of a single piece may also be employed. Valve body 825 consists of a hollow core formed in the material encompassing the various components of module 820. Needle portion 824 is preferably mounted within the hollow core of valve body 825 by mounting members 826a and 826b. More particularly, valve body 825 is molded into or milled out of the material (e.g., PEEK) forming the main body of module 820. Its cooperation with needle portion 824 creates a situation similar in nature to that of well known needle valve assemblies, which have been utilized in many different mechanical assemblies for some time. For example, as shown in the view of FIG. 39A, movement of portion 824 to the left side of body 825 blocks all fluid flow through a passage 827 to a passage 828. These passages are routes that fluid flowing from pump 800 must take, and will be discussed more fully below in relation to the path of fluid from pump 800. Alternatively, as is depicted in FIG. 39B, movement of portion 824 to the right side of body 825 allows fluid flow from passage 827 to passage 828. Clearly, as those of ordinary skill in the art would recognize, intermediate positions of portion 824 with respect to body 825 may vary fluid flow accordingly. In this regard, it is to be understood that movement of portion 824 within valve body 825 is generally transverse to that of fluid flow through valve body 825.

In addition, the nature of valve 821 smoothes out the flow of fluid to a patient upon actuation of double sided portion 824. This is best illustrated in the view of FIG. 39A where movement of portion 824 to a closed position simultaneously creates a space to the left of passages 827 and 828, denoted by reference numeral 829. This space 829 receives the excess fluid which has gathered around passages 827 and 828 upon movement of portion 853 to a closed position, rather than the fluid being pushed into the body of the patient when the valve is closing. In the case of a two piece 824a and 824b needle portion 824, during assembly, one piece may be inserted into each side of the core formed in body 825. Thereafter the pieces 824a and 824b may be assembled together through a snap connection or the like.

As is mentioned above, motor 822 and offset cam 823 are designed to move portion 824 of valve 821 to the open position depicted in FIG. 39B upon actuation of the motor. The general offset nature of cam 823 essentially pushes portion 824 upon its rotation in one direction, while rotation in the other direction allows portion 824 to return to its original closed position under the influence of members 826a and 826b. In this regard, members 826a and 826b connecting needle portion 824 to body 825 allow the left and right movement depicted in FIGS. 39A and 39B without the loss of fluid from valve 821. These members may be constructed of a pliable material, such as rubber or silicone, and are preferably biased in a single direction. For example, mounting members 826a and 826b may be designed so as to return portion 824 to the closed position shown in FIG. 39A. Alternatively, a secondary mechanism may also be provided to cause portion 853 to move back to the closed or open position. Suitable structures may include leaf springs, additional motor mechanisms, or the like. It is also noted that members 826a and 826b could be constructed of other materials, such as titanium, or could include both a metal and a polymeric material. Finally, members 826a and 826b could include a central cavity including an oil (e.g., silicone oil) which may further aid in preventing the loss of fluid from valve 821.

Restrictor module 820 also preferably houses two pressure sensors 830 and 831 (best shown in FIG. 35) that sit in sensor seats 832 and 833 (best shown in FIGS. 40 and 41) respectively, a fixed flow resistor or restrictor 834 (best shown in FIG. 40), an electronic board 835 having various electrical components mounted thereon, and one or more batteries 836. Pressure sensors 830 and 831 are preferably positioned and utilized to measure the pressure of fluid flowing on either side of fixed restrictor 834. For example, sensor 830 is shown positioned so as to take an initial pressure reading of a medicament or other active substance being dispelled from chamber 806, and sensor 831 is shown positioned so as to take a pressure reading when the substance has passed through fixed restrictor 834. This provides readings of the pressure of the fluid being dispelled from pump 800, and also of the pressure just prior to the fluid entering valve 821. Clearly, the more closed valve 821 is, the higher the pressure, and vice versa. These pressure readings are preferably processed by certain of the various electrical components disposed on board 835 in order to determine the flow rate of the active substance being provided by pump 800. Of course, there are many different fashions in which this may be done, and those of ordinary skill in the art would readily recognize that the methods of calculating the flow rate, as well as the electrical architecture employed to do so, may vary accordingly. One preferred embodiment pump 800 utilizes sensors 830 and 831 that are manufactured by Intersema Sensoric SA of Bevaix, Switzerland and sold under the part number MS 5401. The battery or batteries 836 are preferably utilized to power the various elements of module 820 which require power. For example, batteries 836 may provide power to motor 822, any sensors 830 and 831 being employed and the various electrical components, among other elements. In the embodiment depicted in FIG. 35, batteries 836 are preferably designed so as to fit within a cut out 837 formed in module 820, and the two batteries are designed to power different elements.

In use, pump 800's operation (with module 820 attached thereto) is not unlike that of pump 700. An active substance or other fluid is preferably dispelled from upper chamber 806 of pump 800 through exit opening 817 in upper portion 801. This opening is similar to that of opening 730 of pump 700, and is preferably designed to cooperate with a corresponding entrance opening 817' (best shown in FIG. 45) on the underside of restrictor module 820. Likewise, an exit opening 818' (also best shown in FIG. 45) on the underside of restrictor module 820 is preferably designed to cooperate with entrance opening 818 in upper portion 801. This leads to fluid being sent through outlet duct 819 and ultimately through a catheter (not shown) to a portion of the patient's body. In order to ensure proper alignment of these openings, apertures 813a' and 813b' (best shown in FIGS. 44 and 45) formed in module 820 are designed to align with apertures 813a and 813b in upper portion 801 of pump 800, respectively. In addition, pump 800 includes openings 852 and 854 (best shown in FIG. 32) located near protrusions 817 and 818, respectively. These openings are designed to receive protrusions 856 and 858 (best shown in FIG. 45). Thus, the design essentially includes four elements which ensure alignment of module 820 on pump 800. Although many different attachment mechanisms may be utilized in connecting module 820 to pump 800, screws 814a and 814b are shown in the drawings. The major difference between the flow of a fluid dispelled by pump 800 and fluid dispelled by pump 700 is the route taken through module 820, which will now be discussed.

Figure 41:
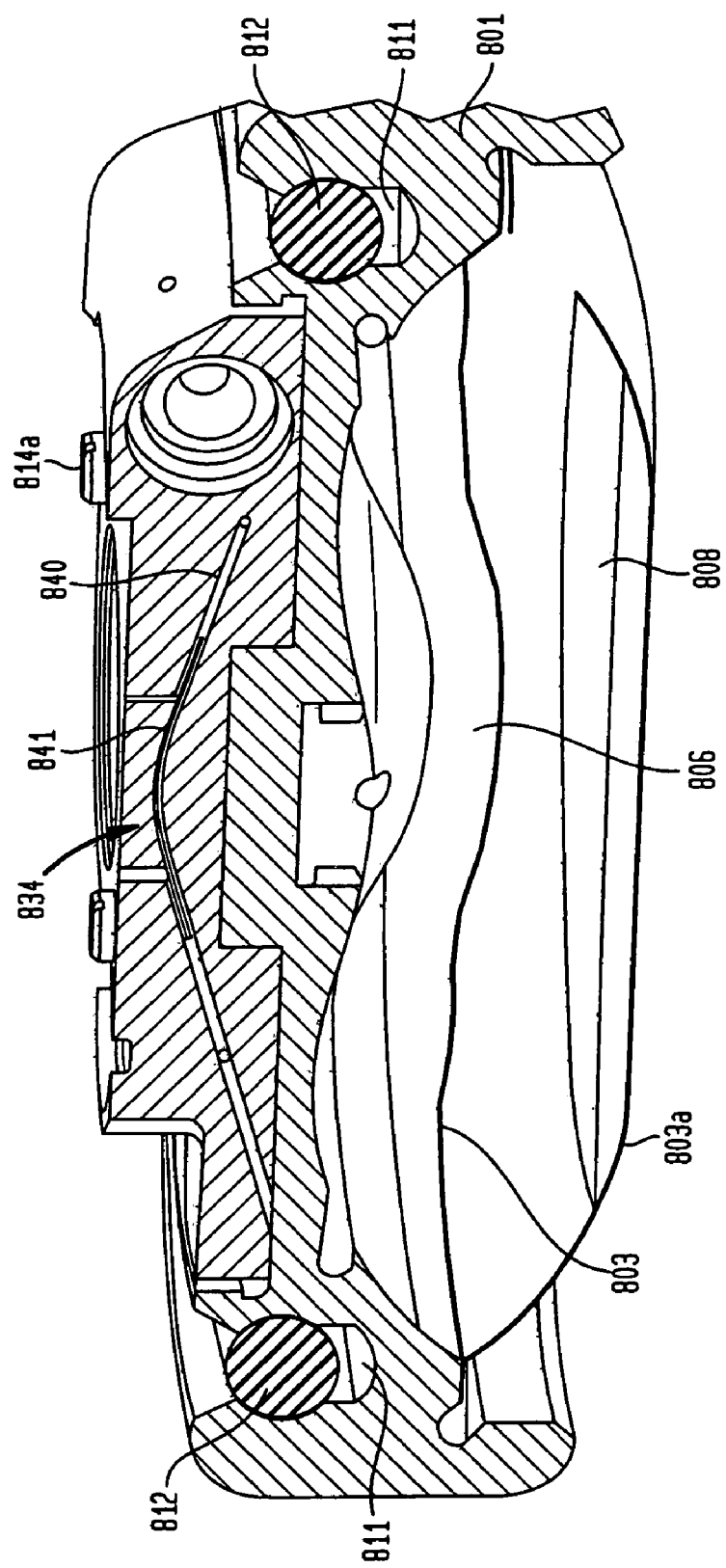
FIG. 41 is a side perspective view of the pump and module of FIG. 35, with certain portion of the module being removed for illustrative purposes.

FIGS. 38-43 depict the various passages for fluid flow through module 820. Referring to FIG. 40, once fluid is allowed to pass into module 820, it is preferably first fed through a first passage 838 to the first pressure sensor 830 where an initial pressure reading is taken. Alternatively, a separate opening and passage may be provided for taking an initial pressure reading with first sensor 830, although this may require a separate opening to be formed in portion 801 of pump 800. Subsequent to the initial pressure being taken, the fluid may pass through a second passage 839 and into fixed restrictor 834. As is best shown in FIGS. 40-41, fixed restrictor 834 includes a glass capillary 840 or the like, in which is disposed a filament 841. Capillary 840 is curved and filament 841 is pushed to one side thereof. As is discussed more fully above, this construction lends itself well to reducing the flow of a fluid flowing therethrough. Instead of a capillary, a curved passage could be formed in the material of module 820 and filament 841 could be disposed within same.

Once through fixed restrictor 834, the fluid preferably flows into a passage 842. This passage branches off to second sensor 831 (where a second pressure reading is taken) and to passage 827 leading to the needle valve 821. In addition, at least passage 839 includes a section which leads away from normal fluid flow. In this regard, it is to be understood that some fluid may flow in this direction, but upon the build up of fluid, the closed section will cause fluid to run in the contemplated direction. These ancillary passages may be provided during the manufacture of module 820, as will be discussed more fully below. Once delivered to valve 821, the position of portion 824 within body 825 determines the flow rate to the patient. It is noted that absent some outside forces (e.g., valve 821 reducing the flow rate), the maximum flow rate of the fluid will always be its initial flow rate from chamber 806 reduced by the fixed flow restrictor 834.

Figure 42:
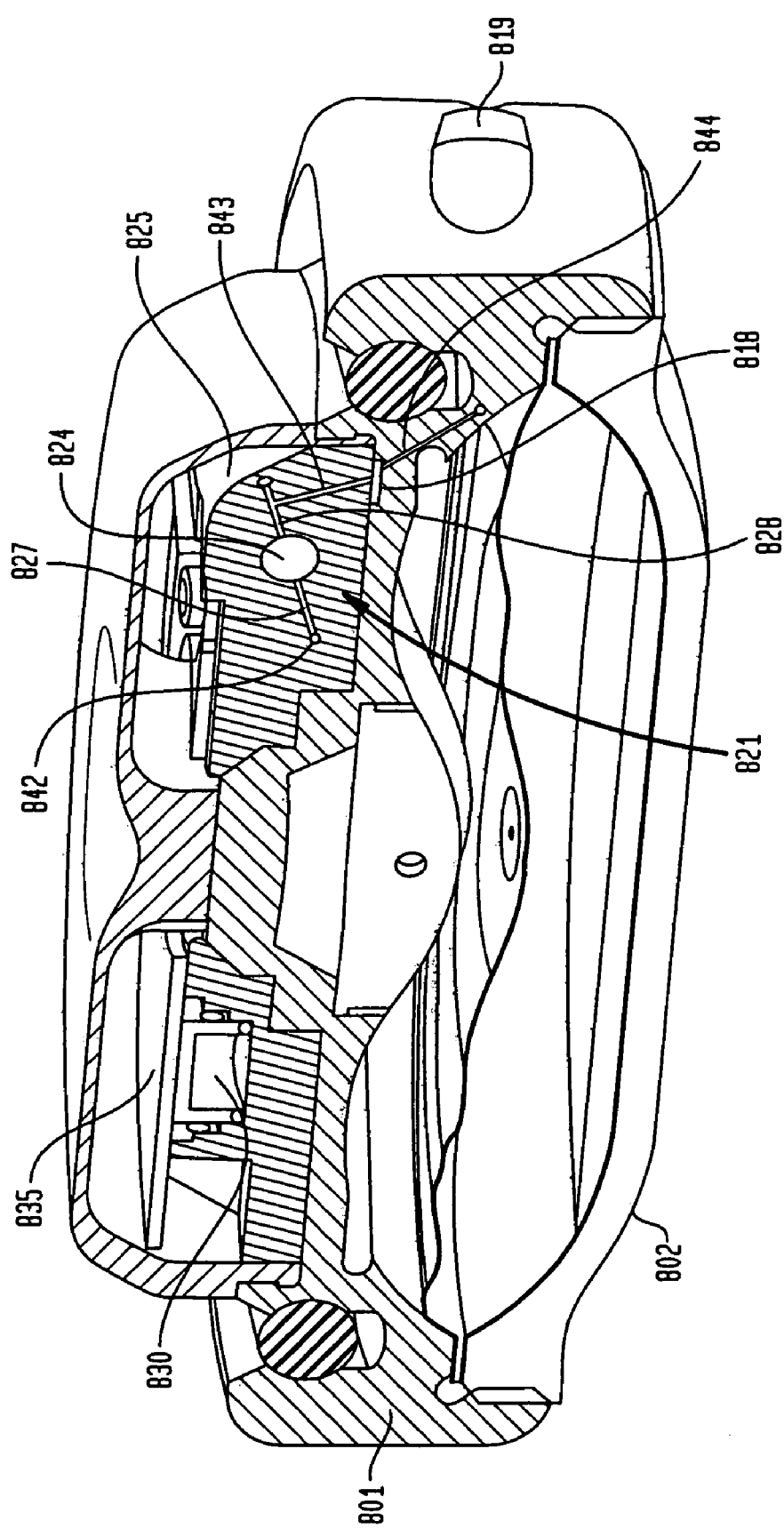
FIG. 42 another cross sectional view of the pump and module of FIG. 35.
Figure 43:
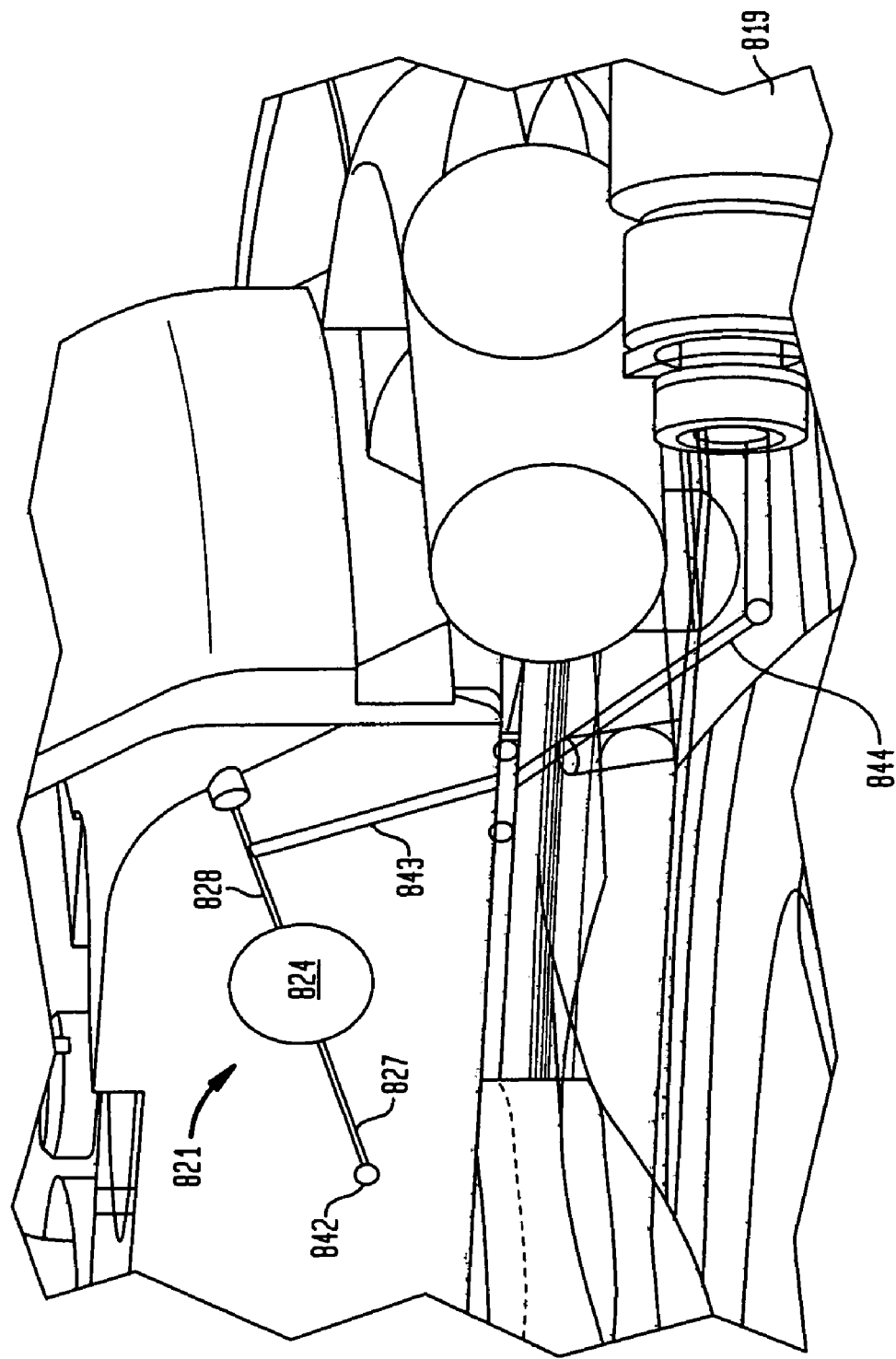
FIG. 43 is an enlarged version of FIG. 42, with certain portions shown as transparent for illustrative purposes.

FIGS. 42 and 43 further illustrate the path taken by fluid exiting valve 821. More particularly, fluid exiting valve 821 enters passage 828, and then passes into a passage 843 which leads the fluid out of module 820. Thereafter, the fluid is allowed to pass into passage 844 of pump 800 and through outlet duct 819. This ultimately leads to the fluid being delivered through a catheter (not shown) to a patient site. It is to be understood that any catheter may be employed, including, but not limited to, one or two-piece catheters. In addition, a specific connection mechanism between such catheter and outlet duct 819 of pump 800 may be employed. For example, U.S. Pat. No. 5,423,776 to Haindl, the disclosure of which is hereby incorporated by reference hererin, teaches a flexible coupling for coupling a flexible catheter to a port that may be utilized in conjunction with the present invention.

Figure 46:
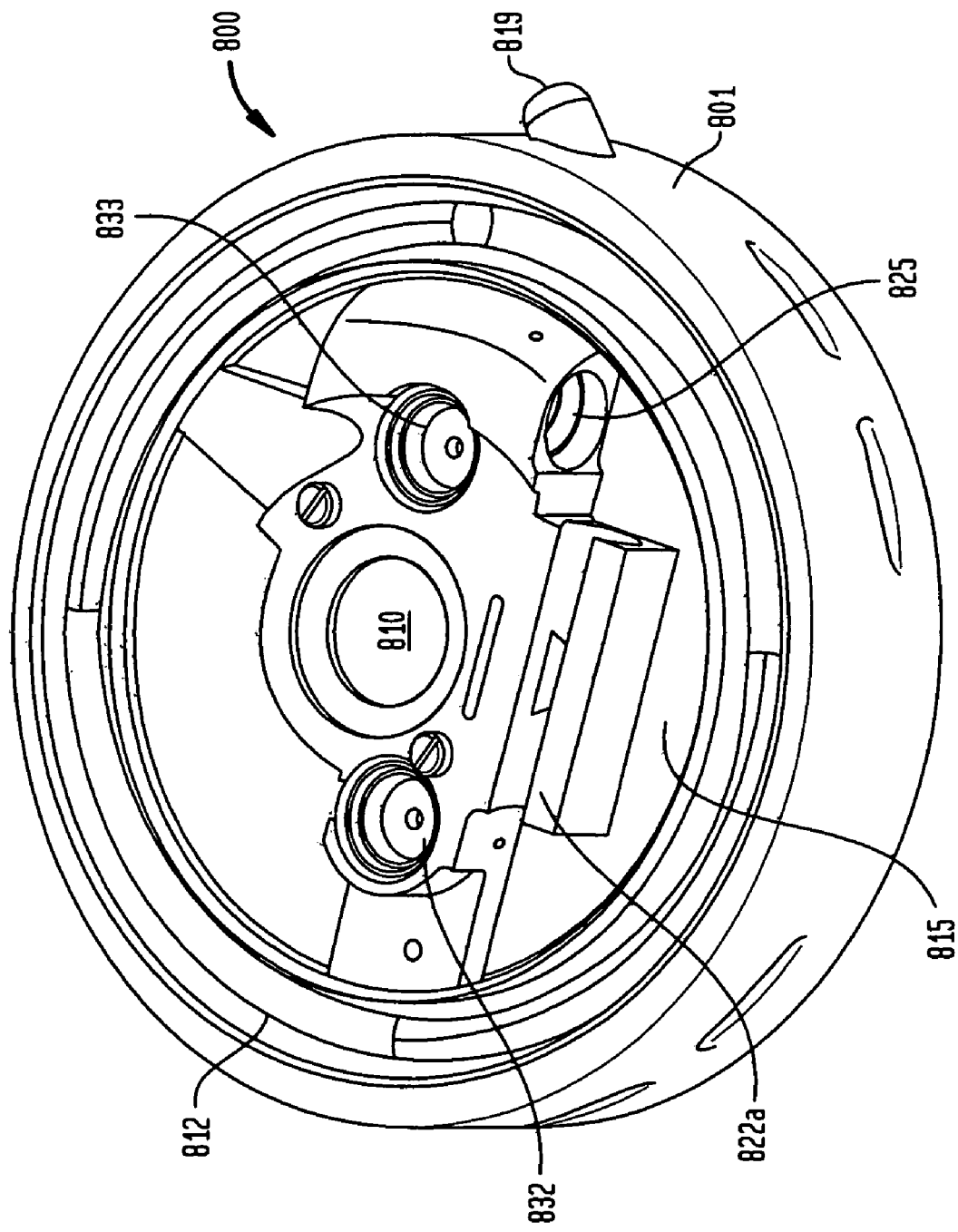
FIG. 46 is a top perspective view of the pump and module of FIG. 46 with certain portions of the module being removed for illustrative purposes.

Manufacture of pump 800 and restrictor module 820, may be accomplished in many different fashions. For example, the various elements of module 820 may positioned in the configuration depicted in the figures, and thereafter injection molded with a material such as the above-discussed PEEK material. Other suitable materials may also be utilized. Alternatively, a mold may be utilized to form a shell of material, in which the various elements are disposed. This shell of material is shown in FIG. 46. Subsequent to either of the above molding steps, the necessary passages for allowing the normal flow of fluid through module 820 may be drilled in the material. Because of the relatively small nature of module 820, this drilling process preferably includes drilling from the exterior of and into the material forming module 820. This is preferably done multiple times, from different angles, in order to form the necessary connected passages forming the flow path. Once the necessary passages are created and a suitable flow path is embedded in module 820, certain of the remaining and unnecessary exterior openings created by the drilling processes are closed up with epoxy or some other suitable material. This method of manufacturing module 820 is evidenced in the aforementioned passage 839 which includes the passage extending away from the fluid flow path. Of course, certain openings remain, such as the openings 817' and 818' which allow fluid to flow from chamber 806 and into module 820 and fluid to flow from module 820, respectively. In addition, as is alluded to above, valve body 825 is preferably either molded or milled into the material of module 820. Thus, restrictor module 820 is a single stand alone component capable of cooperation with pump 800.

Figure 44:
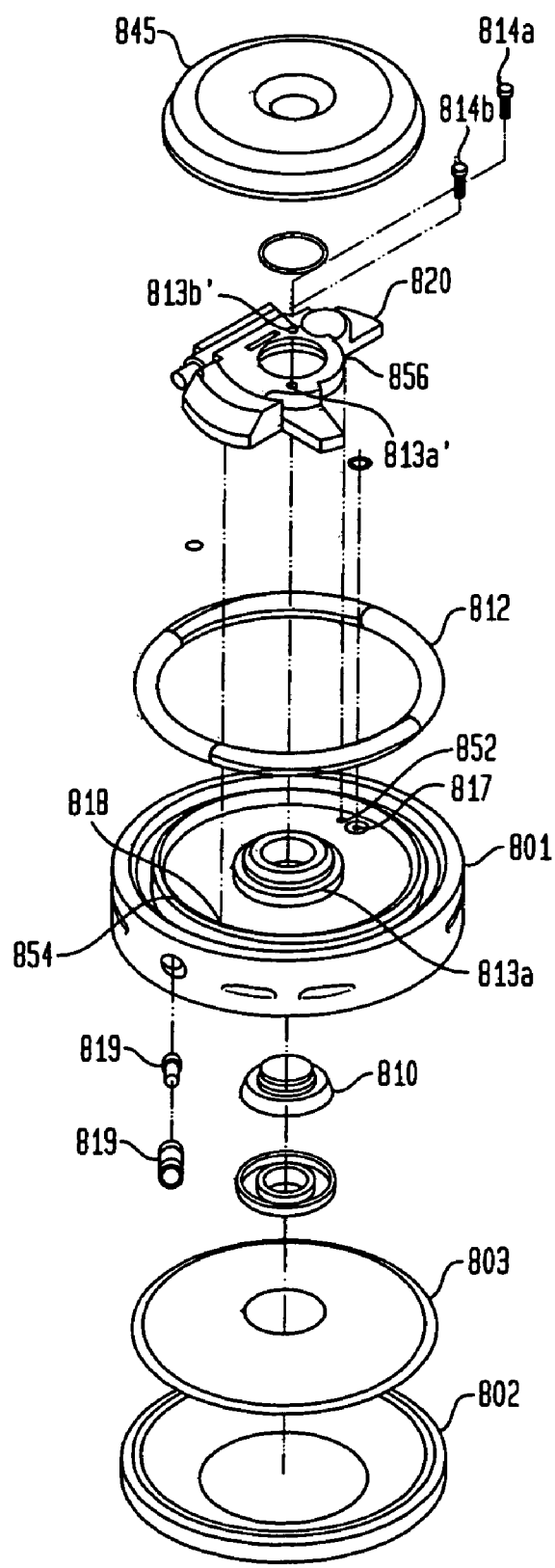
FIG. 44 is a top perspective exploded view of the pump and module of FIG. 35.
Figure 45:
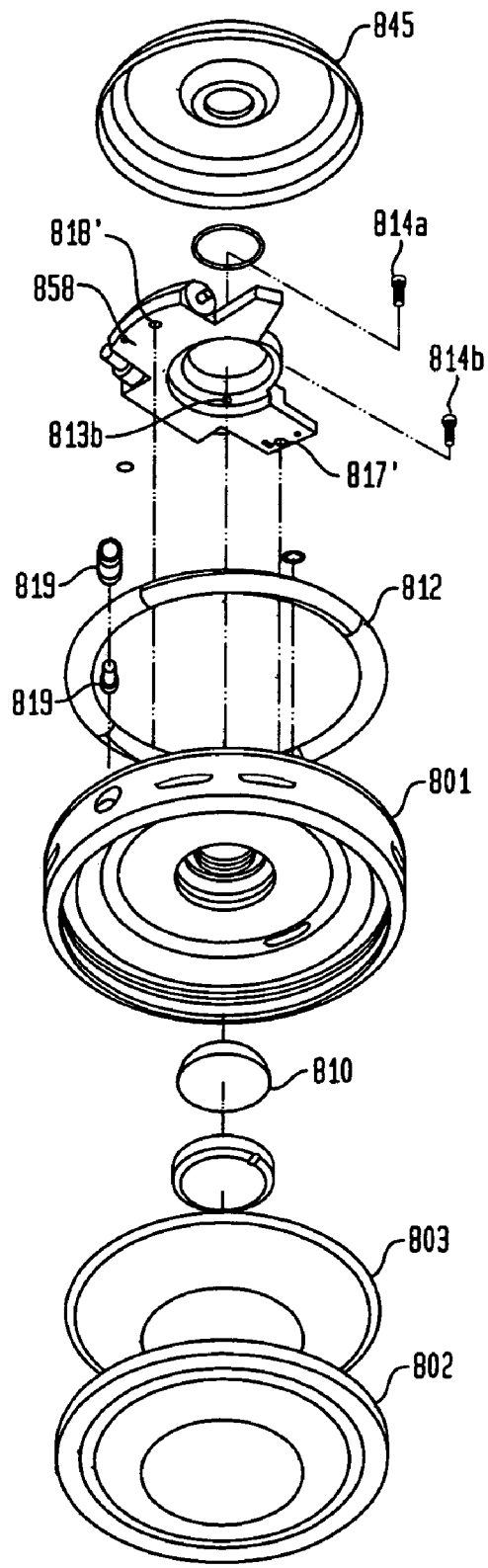
FIG. 45 is a bottom perspective exploded view of the pump and module of FIG. 35.

FIGS. 44 and 45 depict exploded views of the cooperation of pump 800 and module 820. The affixation of module 820 to pump 800 is preferably done so that the components cannot become dislodged at any point during use. As is shown, screws are utilized to fixably connect the two components, with the screws not only attaching module 820 to pump 800, but also clamping circuit board 835 to module 820 (as best seen in FIGS. 35 and 36), and thereby holding sensor 830 in seat 832 and sensor 831 in seat 833, as well as motor 822 in its seat 822a in module 820 (see FIG. 46). Alternatively, such sensors may be affixed in their respective seat absent force provided by the circuit board. Whatever the attachment of module 820 to pump 800, such is preferably designed so that the needed cooperating passages of pump 800 and module 820 (i.e., 817/817' and 818/818') not only line up, but create relatively tight interfaces that do not allow inadvertent fluid leakage. O-rings may be provided not only at these connections, but also in the connections between the sensors and the seats.

As is shown in FIGS. 36, 37, and 42-45, pump 800 may include a cap 845 which snaps into shoulder 816 of upper surface 804. This cap preferably provides a cover for module 820 from the environment of the human body. In addition, it is to be understood that certain or all elements of module 820 (e.g., batteries 836, motor 822, sensors 830 and 831, circuit board 835, etc.) may be packaged in a hermetically sealed package or packages (schematically illustrated as element 844*b* in FIGS. 49A and 49B), which are conventionally employed in implantable medical devices. Those of ordinary skill in the art would recognize the many different types of hermetically sealed packages that can be employed in the present invention. Nonetheless, as will be discussed more fully below, certain elements (e.g., an antenna 844*c*) may need to breach the barrier created by such packaging (but remain under cap 845) in order to allow pump 800 and module 820 to operate properly.

Figure 47:
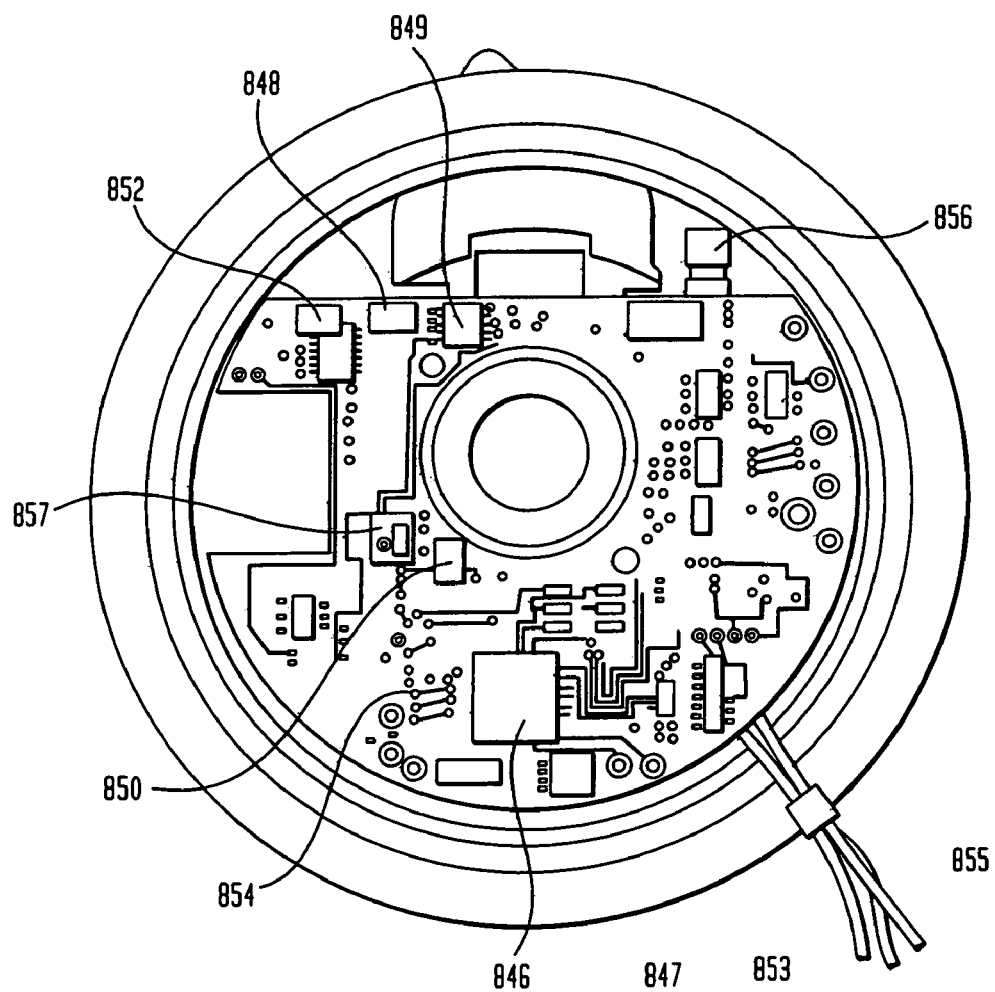
FIG. 47 is a top view of the pump and module of FIG. 46 with attention to an electronic board of the module.
Figure 48:
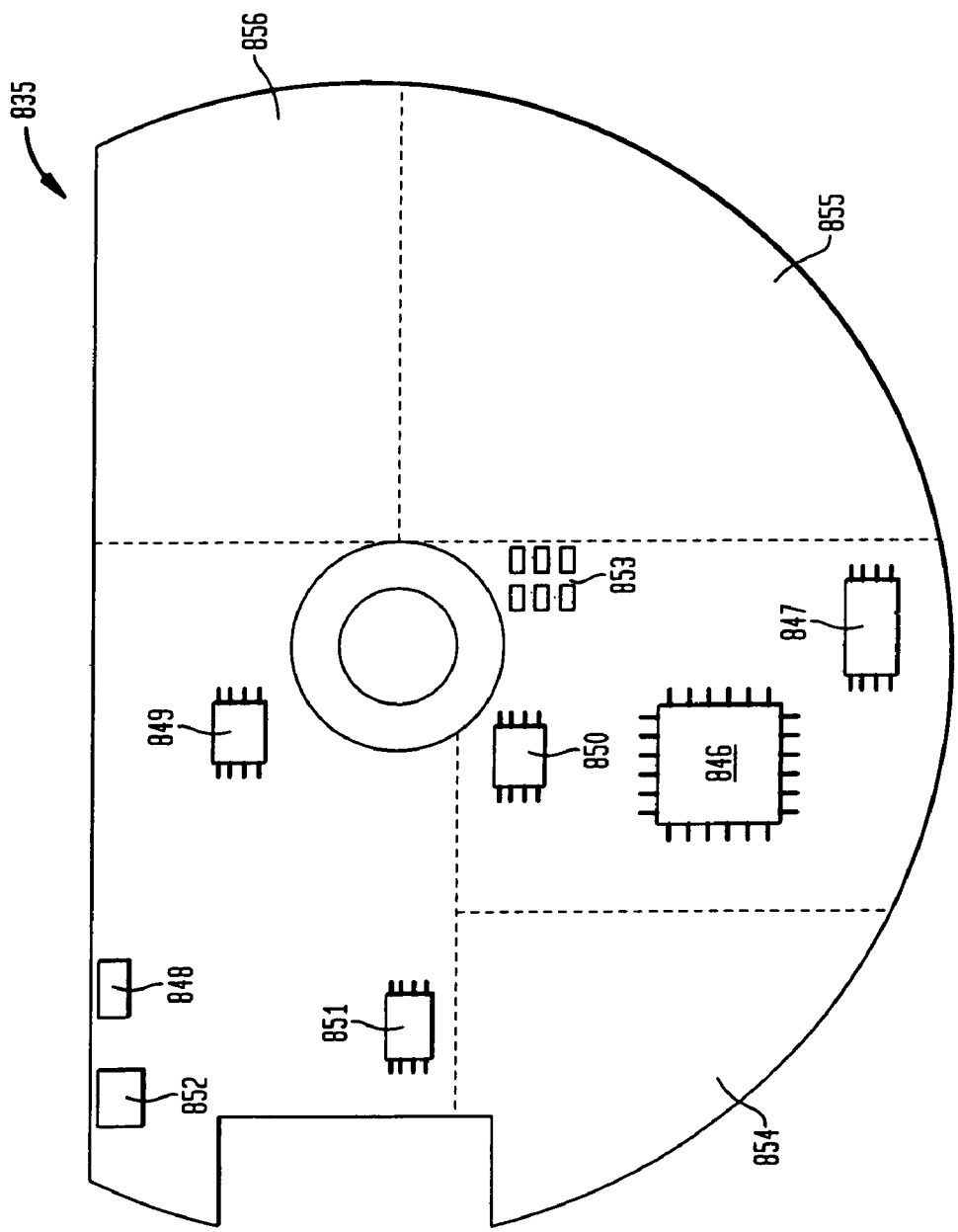
FIG. 48 is an illustration of the electronic board of FIG. 46.

FIGS. 47 and 48 more specifically depicts one suitable circuit board 835 for use with module 820 and pump 800. As mentioned above, this board includes several electronic components including a processor chip 846, a memory 847 for storing a program to be run by chip 846, a capacitor 848 for storing energy from batteries 836, a first amplifier 849 for boosting the signal of sensor 830, a second amplifier 850 for boosting the signal of sensor 831, a dual channel analog to digital converter 851 for converting analog signals received from sensors 830 and 831 to digital signals, input pads 853 useful in loading a desired program to memory 847, a power section 854, a motor driver section 855 and a radio receiver/transmitter section 856. Sensors 830 and 831 include pads which electrically connect with traces provided on the underside of board 835. While FIGS. 47 and 48 depict an actual illustration of a working embodiment board 835 (with conventional circuit traces, resistors, contact points, etc . . . ) those of ordinary skill in the electrical arts would recognize the many different types of connections and circuit elements that may be employed to effectuate the desired functionality of the pump as shown in FIGS. 49A and 49B.

Figure 49A:
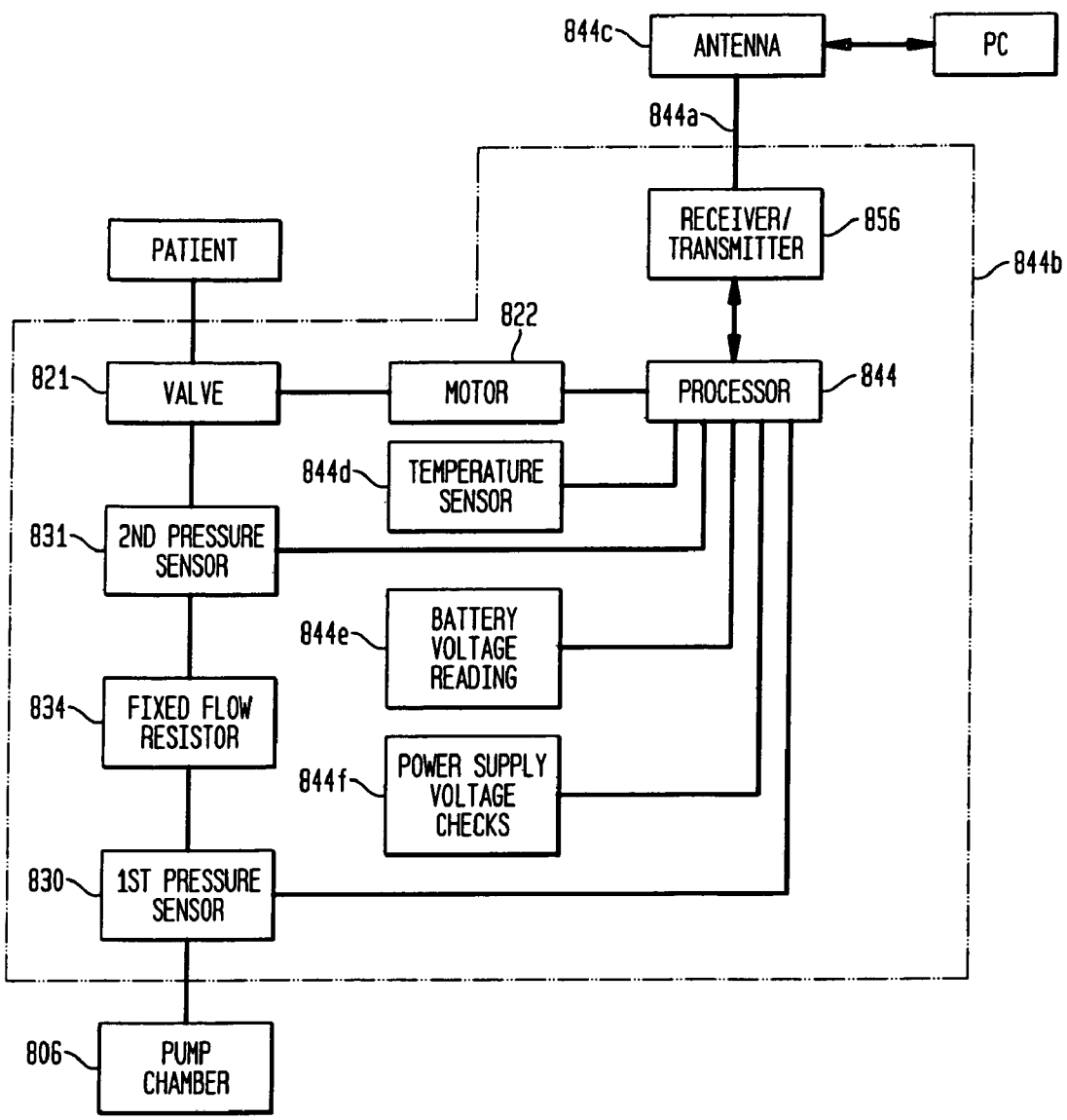
FIG. 49A is a block diagram illustrating the general operation of the pump and module of FIG. 35 in conjunction with a PC.
Figure 49B:
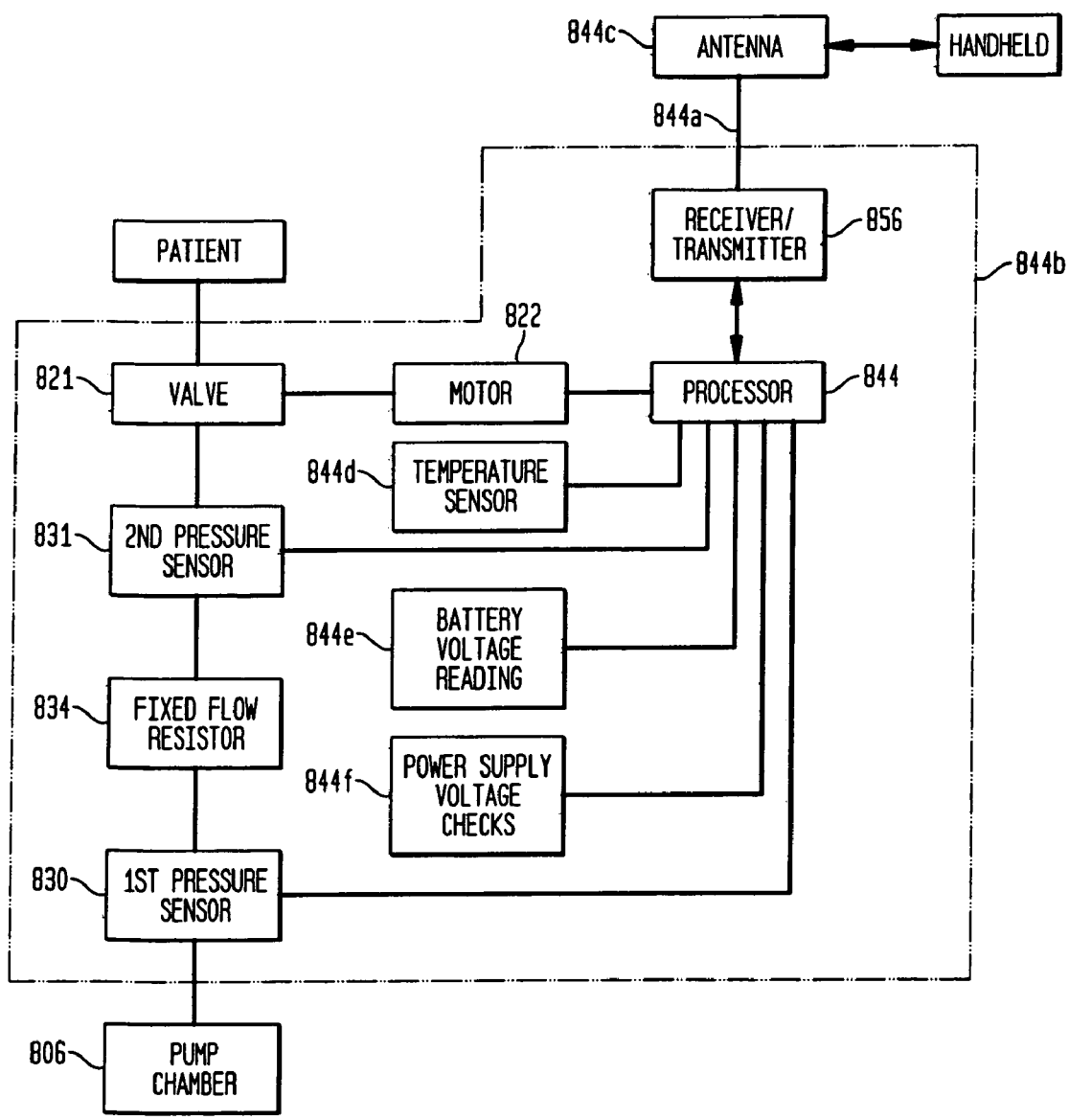
FIG. 49B is another block diagram illustrating the general operation of the pump and module of FIG. 35 in conjunction with a handheld device.

FIGS. 49A and 49B depict a block diagram illustrating the general operation of module 820 and pump 800. As is clearly shown in those figures, processor chip 846 is provided with the information garnered by sensors 830 and 831 so as to provide an instantaneous indication of flow rate through the fixed flow restrictor 834. The flow rate desired for the patient is fed to the processor by line 844*a* and compared in the processor to the rate detected across the fixed flow restrictor. If the desired rate is different from the current rate flowing through the fixed flow restrictor (as detected by sensors 830 and 831), motor 822 is actuated to move portion 824 of valve 821 and thusly effectuate a change in the flow rate. Motor 822 varies portion 824 of valve 821 until the sensed flow rate across the fixed restrictor equals the desired rate, at which point motor 822 stops until there is a new flow rate desired, at which time the above process repeats. Although many different types of processor chips may be utilized in module 820, such must conform to the size and shape restraints of pump 800. For example, chip 846 depicted in the pictures is designed to fit onto the upper portion board 835 between the board and cap 845. The particular chip shown is manufactured by Microchip Technologies of Chandler, AZ and sold under part no. PIC18LF2580.

The above-noted operation of module 820 may be designed so as to be an intermittent process, rather than a continuous process. For example, in one embodiment, module 820 is designed to take pressure readings with sensors 830 and 831 once every fifteen (15) minutes. Likewise, in the same embodiment, module 820 is designed to actuate valve 821 once per hour. This type of operation would facilitate an average desired flow rate of medication, rather than a real time monitoring and correcting of same. Operation in such a fashion may dramatically improve battery life and the overall working life of the various components of module 820. However, it is to be understood that module 820 may be configured so as to operate at any time interval, including in real time. As is shown in FIGS. 49A and 49B, module 820 preferably also allows for the monitoring of system temperature, battery voltage, and power supply voltage. The sensors utilized in monitoring these conditions are labeled with reference numerals 844*d*, 844*e*, and 844*f* for clarity purposes in FIGS. 49A and 49B. Any suitable sensors may be employed for these purposes, and readings may be taken at any time interval. For example, one embodiment takes such readings every one (1) second to ensure the health of the system. In addition, it is contemplated to turn the radio/receiver components on and off every so often (e.g., every 15 secs.).

It is also to be understood that often times sensors 830 and 831 will include an offset in the electrical signals dispelled by each sensor. For example, in the above-noted preferred embodiment sensors, the offset can be as high as plus or minus 40 milivolts. Thus, in order to garner an accurate pressure reading, and thusly, an accurate flow rate reading, this offset must be periodically determined and corrected. One method for doing so includes closing valve 821 so that no fluid flow from pump 800 to the patient occurs. This results in a build up of pressure in module 820, which, when equalized, results in identical pressures at sensors 830 and 831 respectively, and should result in identical readings from each sensor. However, because of the aforementioned offset, the readings will often be different. Thus, the respective readings of sensors 830 and 831 are taken at this point, and fed to processor chip 846. The difference in the readings (if any) is registered and then accounted for in further flow rate calculations. As such, the offset is periodically reset in order to ensure accurate measurements of the pressures and flow rates. This offset correction process may be undertaken at any period or at any given interval. For example, in one embodiment, such offset correction process is undertaken once a day.

One major benefit provided by pump 800 and module 820 is the fact that total drug delivery may be monitored by a doctor or patient. This is contrary to well-known implantable pumps which require a painful and invasive procedure to be performed in order to detect the amount of medicament dispensed to a patient. As is discussed above, the particular flow rate being dispensed to the patient is at least periodically monitored by module 820. In some cases, this flow rate is kept at an average flow rate for a particular time period. A controller (like those discussed below) may be designed to keep a running tab of the amount of medicament dispensed, based on the flow rate readings or average flow rate. Thus, the patient or doctor may be provided with a gauge (possibly built into the controller) which gives a real time or periodic measurement of medicament dispensed or medicament remaining within pump 800. The latter would most likely be based upon the initial amount provided in pump 800. This is a very important benefit provided by pump 800 and its cooperation with module 820.

The amount of medicament dispensed is therefore determined by multiplying the average flow rate (or real time flow rate) by the time at which the flow rate from pump 800 was such. All of the different time periods are accounted for and the overall amount is determined by adding each of these individual amounts together. As is discussed above, readings by sensors 830 and 831 may be taken at any interval, for example, every fifteen minutes. In order to maintain an average flow rate, these readings are taken and a correction of valve 821 position is only done when the flow rate deviates from the desired flow rate by a certain amount. For instance, is certain embodiments, a correction of the flow rate is made when the flow rate deviates by 10% of the overall flow rate. Thus, if the pump is operating at 10% less of a flow rate than that which is desired, a correction is made so as to level out the average flow. In that case, valve 821 would be actuated so as to allow for a flow which is slightly higher than the desired flow. This preferably equalizes the average flow over the particular time. Of course, if the average flow is 10% or more higher than the desired flow, valve 821 would be actuated to allow for a lower flow rate. Minor deviations in flow rate caused by wear of the components and the like can also be dealt with through this method of monitoring and varying the flow. Once again, operation in this fashion prevents the constant use of the particular power source of pump 800, thereby extending its useful life.

As noted previously, restrictor module 820 may be remotely controlled to properly dispense a predetermined amount of an active substance to a patient. Such external controllers, for example, which transmit RF, magnetic or electric field, or other signals, are well known in the art and may be designed so as to be easily operable by a doctor, other medical professional, or even the patient having pump 800 implanted in their respective body. For example, FIG. 49A depicts pump 800 being utilized in conjunction with a PC, while FIG. 49B depicts pump 800 being utilized in conjunction with a handheld device. It is noted that the handheld device may be any suitable device, such as a stand-alone device or one which incorporates other useful features. For instance, a controller for use in connection with the present invention may be incorporated into a blackberry, PDA or other handheld device. An antenna 844c may be disposed between board 835 and cap 845, and associated with radio receiver/transmitter section 856 of board 835. Preferably, this antenna extends through any hermetically sealed package that may be employed, so that clear transmission is ensured. Operation of pump 800, and in particular restrictor module 820, may involve the implementation of different algorithms or programs in order to produce the desired flow rate from pump 800. Such are also well known in the art, and may also be programmed externally or hardwired into module 820. The aforementioned input pads 853 may be useful in loading different programs into memory 847.

It is noted that other designs for restrictor module 820 may be employed, as can many different manufacturing processes. For example, it is envisioned to include more or less elements within module 820. In addition, it is noted that the depiction of module 820 shown in FIGS. 35-46 is merely but one embodiment of a suitable module, and others are envisioned which employ different shapes and/or sizes, as well as different configurations of the elements disposed therein. It is also to be understood that, while described above, as being constructed of PEEK material or the like, pump 800 and/or module 820 may be of any biocompatible material or combination thereof. For instance, upper portion 801 and the other portions of the main housing of pump 800 may be a PEEK material, while restrictor module 820 is constructed of or the various components of module 820 are encapsulated with a metallic material. Likewise, the attachment of module 820 to pump 800 may be accomplished in many different fashions.

Figure 50:
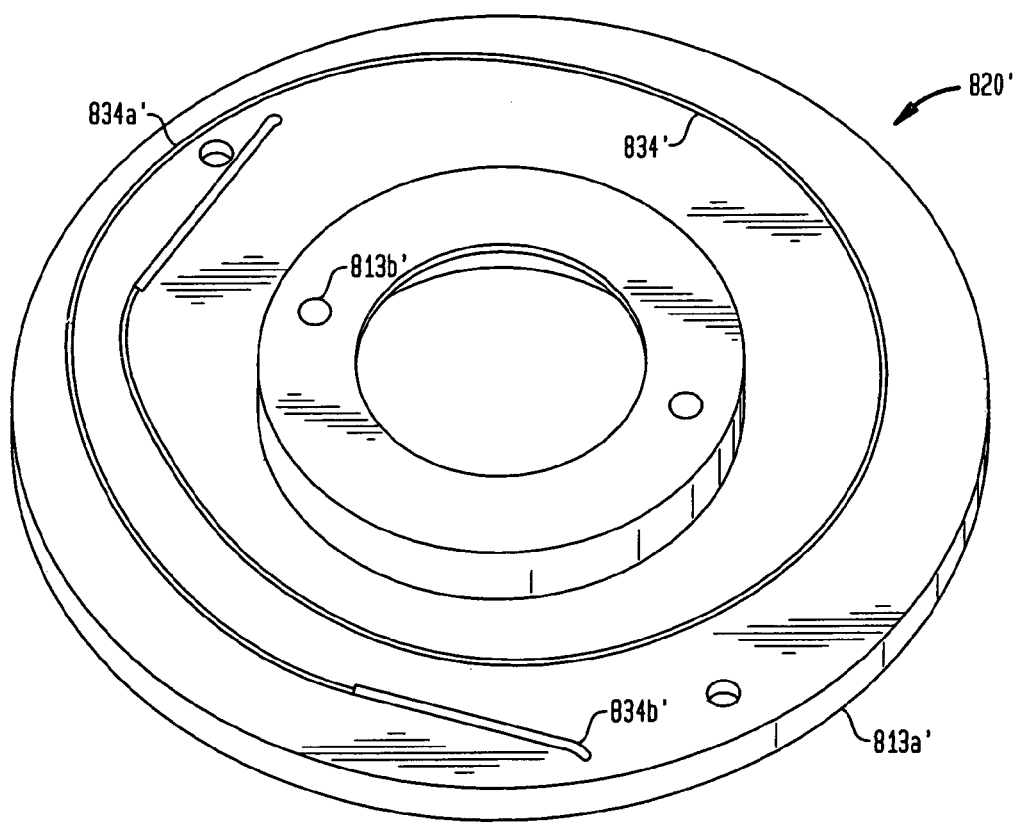
FIG. 50 is a perspective view of a constant flow module for use with an implantable pump.
Figure 51:
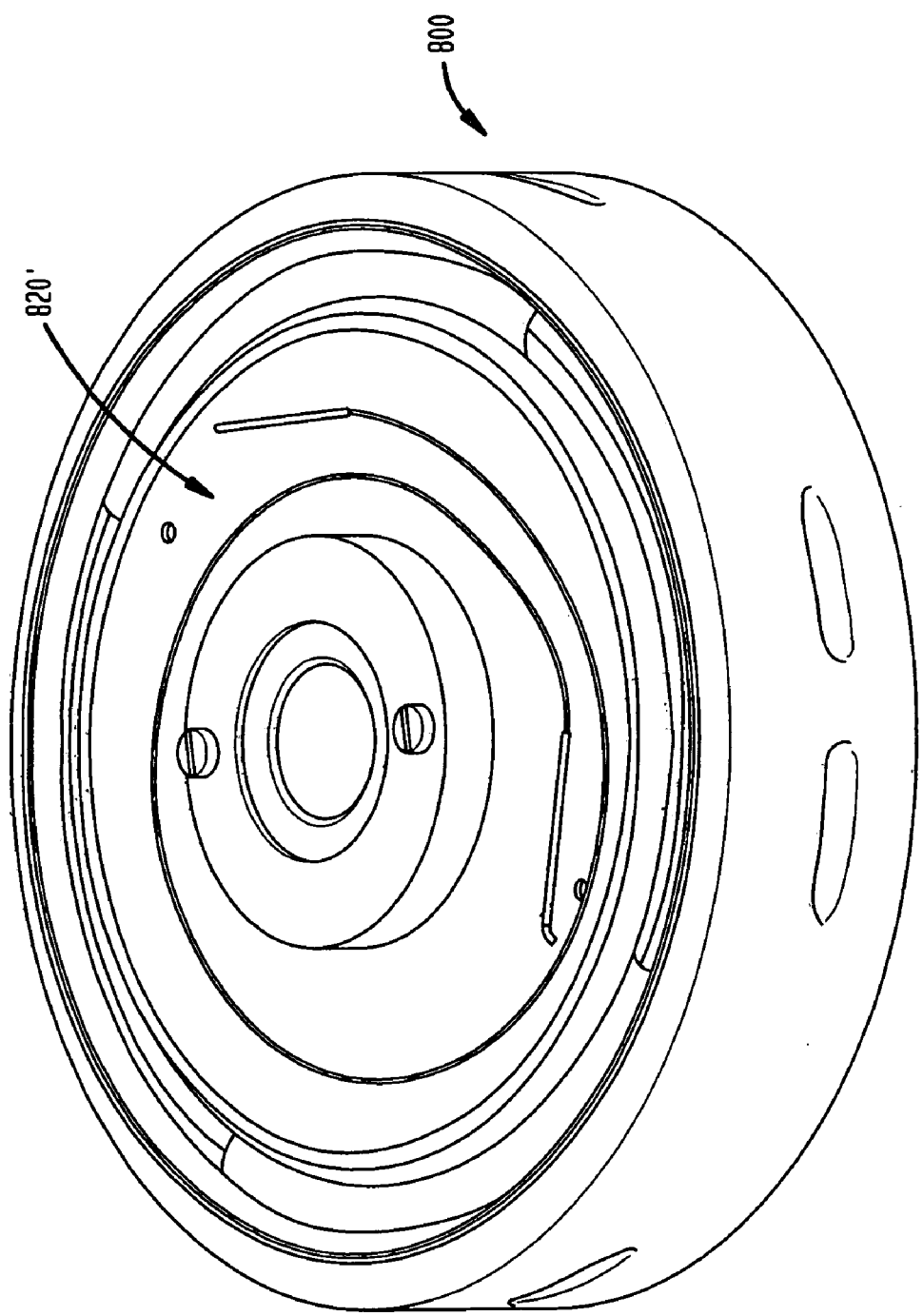
FIG. 51 is a perspective view of the constant flow module of FIG. 50 connected to the pump of FIG. 32.

Finally, it is envisioned to provide a constant flow restrictor module capable of cooperating with a pump like pump 800. As is shown in FIG. 50, module 820' is capable of cooperating with pump 800. Essentially, this constant flow module 820' employs a similar attachment configuration for attaching to pump 800, as that of module 820 (e.g., apertures 813$a'$ and 813$b'$ which cooperate with screws 814$a$ and 814$b$ discussed above), but does not include the various elements useful in varying the flow rate of fluid dispelled from the pump. Rather, as is shown in FIG. 50, module 820' employs a similar overall size and shape, but only includes a single fixed flow restrictor 834', which includes a first side 834$a'$ for receiving a fluid from chamber 806 and a second side 834$b'$ for dispelling fluid for ultimate delivery through outlet duct 819 of pump 800. Thus, in use, fluid dispelled from chamber 806 of pump 800 is fed through restrictor 834'. It is specifically contemplated to provide a module 820' which only allows for a specific flow rate, and such flow rate may be deliberately designed to be less than that capable of being produce from chamber 806 of pump 800. Essentially, the flow rate of fluid through module 820' is dictated by the diameter of restrictor 834', with larger diameters allowing faster flow rates and smaller diameters allowing for slower flow rates. It is to be understood that, like fixed flow restrictor 834, restrictor 834' may employ a filament to further reduce the flow rate of fluid passing therethrough. FIG. 51 depicts pump 800 with module 820' attached thereto, and it is to be understood that cap 845 may further be connected to pump 800 in a fully constructed and ready to implant pump system.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An implantable infusion pump for dispensing an active substance at varying flow rates to a patient comprising:

a constant flow pump having a housing, said housing defining: an upper surface, an active substance chamber, a propellant chamber separated from the active substance chamber by a first flexible membrane, an outlet duct having a catheter attached thereto, an exit opening in fluid communication with the active substance chamber and a entrance opening in fluid communication with the outlet duct; and a removable module, said removable module including: a bottom surface contacting the upper surface of the constant flow pump, an entry formed in the bottom surface in fluid communication with the exit opening of the housing, an exit in fluid communication with the entrance opening of the housing, a needle valve portion having a longitudinally varying cross section along its length disposed within a valve body, means for longitudinally moving the needle portion within the valve body, a fixed flow restrictor in fluid communication between the entry of the removable module and the valve body of the removable module, and first and second pressure sensors for sensing pressure on either side of the fixed flow restrictor;

wherein during operation of the pump system, a fluid dispelled from the active substance chamber by a force from the propellant chamber passes through the exit opening of the housing, through the entry of the removable module, into contact with the first pressure sensor, through the fixed flow restrictor, into contact with the second pressure sensor, through the valve body of the removable module, through the exit of the removable module, through the entrance opening of the housing, through the outlet duct, and through the catheter.

2. The implantable infusion pump according to claim 1, wherein the housing further includes a second flexible membrane enclosing the propellant chamber with the first flexible membrane.

3. The implantable infusion pump according to claim 1, wherein the housing further includes an upper portion and a lower portion.

4. The implantable infusion pump according to claim 3, wherein the upper and lower portions are designed to be screwed together and capture the first and second flexible membranes therebetween.

5. The implantable infusion pump according to claim 4, wherein the upper portion includes a first opening allowing for replenishment of the active substance chamber and a second opening allowing for direct injection of a fluid to the outlet duct.

6. The implantable infusion pump according to claim 5, wherein the first and second openings are covered with septa.

7. The implantable infusion pump according to claim 1, wherein the upper surface of the housing includes an upstanding extension forming a shoulder.

8. The implantable infusion pump according to claim 7, further comprising a cap connected with the shoulder and covering the removable module.

9. The implantable infusion pump according to claim 1, wherein the needle valve portion includes a central point with cross sections on either side of the central point being mirror images.

10. The implantable infusion pump according to claim 1, wherein the means for longitudinally moving the needle valve portion within the valve body include a motor and an offset cam.

11. The implantable infusion pump according to claim 1, wherein the means for longitudinally moving the needle portion within the valve body include a motor, an axle, an eccentric cam body and a bearing, the bearing having an interior rotating portion connected to the eccentric cam body and an exterior portion abutting the needle portion.

12. The implantable infusion pump system according to claim 1, wherein longitudinal movement of the needle valve portion within the valve body is generally transverse to the flow of a fluid from the active substance chamber through the valve body.

13. The implantable infusion pump according to claim 1, wherein the fixed flow restrictor includes a capillary and a filament disposed within the capillary.

14. The implantable infusion pump according to claim 1, wherein the first and second pressure sensors are disposed within seats formed in a solid material portion of the removable module.

15. The implantable infusion pump according to claim 12, wherein the solid material portion is constructed of PEEK.

16. The implantable infusion pump according to claim 1, wherein the removable module further includes a processor chip capable of processing pressure information from the first and second pressure sensors to generate information representative of flow rate through the fixed flow restrictor.

17. The implantable infusion pump according to claim 16, wherein the removable module further includes an electronic circuit board, the processor chip being mounted on the electronic circuit board.

18. The implantable infusion pump according to claim 17, wherein the removable module further includes a power source.

19. The implantable infusion pump according to claim 18, wherein the power source comprises at least one battery.

20. The implantable infusion pump according to claim 16, further comprising an antenna for receiving information representative of a desired flow rate from an outside source.

21. The implantable infusion pump according to claim 20, wherein the outside source is a handheld device.

22. The implantable infusion pump according to claim 20, wherein the outside source is a network.

23. The implantable infusion pump according to claim 1, wherein the removable module is connected to the upper surface of the housing by a fastening means.

24. The implantable infusion pump according to claim 23, wherein the fastening means comprises at least one screw.

25. The implantable infusion pump according to claim 24, wherein the screw passes through apertures formed in the removable module and the housing.

26. The implantable infusion pump according to claim 25, wherein the screw acts to clamp the removable module to the housing.

27. The implantable infusion pump according to claim 26, wherein the removable module further includes an electronic circuit board, the at least one screw passing through an aperture formed in the electronic circuit board.

28. The implantable infusion pump according to claim 27, wherein the first and second sensors are held within seats formed in a solid material portion of the removable module by the electronic circuit board.

* * * * *

UNITED STATES PATENT AND TRADEMARK OFFICE
CERTIFICATE OF CORRECTION

| | | |
|---|---|---|
| PATENT NO. | : 7,637,892 B2 | |
| APPLICATION NO. | : 11/601586 | |
| DATED | : December 29, 2009 | |
| INVENTOR(S) | : Bernd Steinbach et al. | |

It is certified that error appears in the above-identified patent and that said Letters Patent is hereby corrected as shown below:

Column 37, line 12, "claim 4" should read --claim 1--.
Column 37, line 13, "portion" should read --surface--.
Column 38, line 5, "claim 12" should read --claim 14--.

Signed and Sealed this
Twenty-second Day of February, 2011

David J. Kappos
*Director of the United States Patent and Trademark Office*